(12) United States Patent  
Curtiss, III et al.

(10) Patent No.: US 8,889,121 B2  
(45) Date of Patent: Nov. 18, 2014

(54) BACTERIUM COMPRISING A REGULATED RFAH NUCLEIC ACID

(75) Inventors: Roy Curtiss, III, Paradise Valley, AZ (US); Qingke Kong, Tempe, AZ (US)

(73) Assignee: The Arizona Board of Regents for an on Behalf of Arizona State University, Tempe, AZ (US)

( * ) Notice: Subject to any disclaimer, the term of this patent is extended or adjusted under 35 U.S.C. 154(b) by 0 days.

(21) Appl. No.: 13/574,718

(22) PCT Filed: Jan. 21, 2011

(86) PCT No.: PCT/US2011/022110  
§ 371 (c)(1),  
(2), (4) Date: Aug. 28, 2012

(87) PCT Pub. No.: WO2011/091291  
PCT Pub. Date: Jul. 28, 2011

(65) Prior Publication Data  
US 2013/0004537 A1   Jan. 3, 2013

Related U.S. Application Data

(60) Provisional application No. 61/297,315, filed on Jan. 22, 2010.

(51) Int. Cl.
| | |
|---|---|
| *A01N 63/00* | (2006.01) |
| *A61K 39/00* | (2006.01) |
| *A61K 39/02* | (2006.01) |
| *A61K 39/112* | (2006.01) |
| *C07K 14/315* | (2006.01) |
| *C07K 14/255* | (2006.01) |
| *C12N 9/10* | (2006.01) |
| *C12N 1/36* | (2006.01) |
| *A61K 39/09* | (2006.01) |

(52) U.S. Cl.  
CPC ......... *C07K 14/3156* (2013.01); *A61K 39/0275* (2013.01); *A61K 2039/522* (2013.01); *C07K 14/255* (2013.01); *C12N 9/1048* (2013.01); *C12N 1/36* (2013.01); *A61K 2039/523* (2013.01); *A61K 39/092* (2013.01)  
USPC ..... 424/93.48; 424/93.1; 424/93.2; 424/93.4; 424/184.1; 424/200.1; 424/234.1; 424/235.1; 424/278.1; 424/282.1; 514/2.8

(58) Field of Classification Search  
None  
See application file for complete search history.

(56) References Cited

U.S. PATENT DOCUMENTS

| | | |
|---|---|---|
| 4,190,495 A | 2/1980 | Curtiss, III |
| 4,888,170 A | 12/1989 | Curtiss, III |

(Continued)

FOREIGN PATENT DOCUMENTS

| | | |
|---|---|---|
| EP | 0315682 B1 | 12/1993 |
| EP | 0381706 B1 | 4/1995 |

(Continued)

OTHER PUBLICATIONS

Kong et al., (Infect and Immun. Published Oct. 5, 2009. vol. 77(12):5572-5582).*

(Continued)

*Primary Examiner* — Ja'na Hines  
(74) *Attorney, Agent, or Firm* — Polsinelli PC

(57) ABSTRACT

The present invention encompasses a recombinant bacterium comprising a regulated rfaH nucleic acid, as well as a vaccine comprising said recombinant bacterium. Other embodiments of the present invention encompass a recombinant bacterium comprising a regulated rfaH nucleic acid and a regulated rfc nucleic acid, while additional embodiments encompass a recombinant bacterium comprising a regulated rfaH nucleic acid and at least one nucleic acid encoding at least one exogenous antigen.

10 Claims, 20 Drawing Sheets

(56) References Cited

U.S. PATENT DOCUMENTS

| | | | |
|---|---|---|---|
| 4,968,619 | A | 11/1990 | Curtiss, III |
| 5,210,035 | A | 5/1993 | Stocker |
| 5,294,441 | A | 3/1994 | Curtiss, III |
| 5,387,744 | A | 2/1995 | Curtiss |
| 5,389,368 | A | 2/1995 | Curtiss, III |
| 5,424,065 | A | 6/1995 | Curtiss, III |
| 5,468,485 | A | 11/1995 | Curtiss, III |
| 5,654,184 | A | 8/1997 | Curtiss, III |
| 5,656,488 | A | 8/1997 | Curtiss, III |
| 5,672,345 | A | 9/1997 | Curtiss, III |
| 5,679,880 | A | 10/1997 | Curtiss, III |
| 5,686,079 | A | 11/1997 | Curtiss, III |
| 5,817,317 | A | 10/1998 | Titball |
| 5,827,705 | A | 10/1998 | Dean |
| 5,840,483 | A | 11/1998 | Curtiss, III |
| 5,855,879 | A | 1/1999 | Curtiss, III |
| 5,855,880 | A | 1/1999 | Curtiss, III |
| 5,961,983 | A | 10/1999 | Brey et al. |
| 6,024,961 | A | 2/2000 | Curtiss, III |
| 6,180,614 | B1 | 1/2001 | Davis |
| 6,248,329 | B1 | 6/2001 | Chandrashekar et al. |
| 6,350,454 | B1 | 2/2002 | Thune |
| 6,383,496 | B1 | 5/2002 | Curtiss, III |
| 6,399,074 | B1 | 6/2002 | Roland |
| 6,403,094 | B1 | 6/2002 | Titball |
| 6,610,529 | B1 | 8/2003 | Curtiss, III |
| 6,780,405 | B1 | 8/2004 | Curtiss, III |
| 6,872,547 | B1 | 3/2005 | Curtiss, III |
| 6,969,513 | B2 | 11/2005 | Galen |
| 7,083,794 | B2 | 8/2006 | Curtiss, III |
| 7,195,757 | B2 | 3/2007 | Curtiss, III |
| 7,205,125 | B2 | 4/2007 | Castillo |
| 7,341,860 | B2 | 3/2008 | Curtiss, III |
| 7,871,604 | B1 | 1/2011 | Curtiss, III |
| 7,968,101 | B2 | 6/2011 | Kawaoka |
| 8,133,493 | B2 | 3/2012 | Curtiss, III |
| 2003/0031683 | A1 | 2/2003 | Curtiss, III |
| 2003/0175772 | A1 | 9/2003 | Wang |
| 2004/0077556 | A1 | 4/2004 | Chinery |
| 2004/0101531 | A1 | 5/2004 | Curtiss, III |
| 2004/0120962 | A1 | 6/2004 | Curtiss, III |
| 2004/0137003 | A1 | 7/2004 | Curtiss, III |
| 2004/0203039 | A1 | 10/2004 | Hensel |
| 2005/0036987 | A1 | 2/2005 | Pawelek |
| 2005/0106175 | A1 | 5/2005 | Montanes |
| 2005/0106176 | A1 | 5/2005 | Curtiss, III |
| 2005/0118193 | A1 | 6/2005 | Andino-Pavlovsky et al. |
| 2006/0140975 | A1 | 6/2006 | Curtiss, III |
| 2006/0171917 | A1 | 8/2006 | Campbell |
| 2006/0206961 | A1 | 9/2006 | Cirpus |
| 2006/0233829 | A1* | 10/2006 | Curtiss, III ............ 424/200.1 |
| 2006/0234346 | A1 | 10/2006 | Retallack |
| 2006/0275255 | A1 | 12/2006 | Gudkov |
| 2007/0025981 | A1 | 2/2007 | Szalay |
| 2008/0248066 | A1 | 10/2008 | Dubensky, Jr. |
| 2009/0175829 | A1 | 7/2009 | Forbes |
| 2010/0124558 | A1 | 5/2010 | Curtiss, III et al. |
| 2010/0285592 | A1 | 11/2010 | Curtiss, III |
| 2010/0317084 | A1 | 12/2010 | Curtiss, II |
| 2011/0033501 | A1 | 2/2011 | Curtiss, III et al. |
| 2011/0256181 | A1 | 10/2011 | Curtiss, III |
| 2012/0087946 | A1 | 4/2012 | Curtiss, III |

FOREIGN PATENT DOCUMENTS

| | | | |
|---|---|---|---|
| EP | 0465560 | B1 | 6/1996 |
| EP | 0500699 | B1 | 6/1998 |
| EP | 0558631 | B1 | 3/1999 |
| EP | 0433372 | B1 | 6/2002 |
| EP | 1030690 | B1 | 7/2002 |
| EP | 0556333 | B1 | 3/2003 |
| EP | 1326960 | B1 | 12/2004 |
| EP | 0832255 | B1 | 12/2005 |
| EP | 1537214 | B1 | 3/2006 |
| EP | 1292687 | B1 | 8/2006 |
| WO | 88/09669 | A1 | 12/1988 |
| WO | 89/03427 | A1 | 4/1989 |
| WO | 90/02484 | A1 | 3/1990 |
| WO | 90/11687 | A1 | 10/1990 |
| WO | 90/11688 | A1 | 10/1990 |
| WO | 90/12086 | A1 | 10/1990 |
| WO | 91/06317 | A1 | 5/1991 |
| WO | 92/08486 | A1 | 5/1992 |
| WO | 92/09684 | A1 | 6/1992 |
| WO | 93/04202 | A1 | 3/1993 |
| WO | 94/24291 | A2 | 10/1994 |
| WO | 94/24291 | A3 | 12/1994 |
| WO | 96/40947 | A1 | 12/1996 |
| WO | 99/25387 | A1 | 5/1999 |
| WO | 01/83785 | A2 | 11/2001 |
| WO | 02/30457 | A2 | 4/2002 |
| WO | 01/83785 | A3 | 6/2002 |
| WO | 02/059292 | A2 | 8/2002 |
| WO | 02/030457 | A3 | 1/2003 |
| WO | 02/030457 | A3 | 7/2003 |
| WO | 02/059292 | A3 | 7/2003 |
| WO | 03/079792 | A1 | 10/2003 |
| WO | 03/096812 | A1 | 11/2003 |
| WO | 2004/020643 | A2 | 3/2004 |
| WO | 2004/020643 | A3 | 4/2004 |
| WO | 2005/001069 | A1 | 1/2005 |
| WO | 2012087483 | A1 | 6/2008 |
| WO | 2008/141226 | A2 | 11/2008 |
| WO | 2009/025888 | A2 | 2/2009 |
| WO | 2009/046449 | A1 | 4/2009 |
| WO | 2009/046451 | A1 | 4/2009 |
| WO | WO 2009/046449 | * | 4/2009 ............ A01N 63/00 |
| WO | 2010/045620 | A1 | 4/2010 |
| WO | 2010/078584 | A1 | 8/2010 |
| WO | 2010/135563 | A1 | 11/2010 |
| WO | 2011/091291 | A1 | 7/2011 |
| WO | 2011/150421 | A2 | 12/2011 |

OTHER PUBLICATIONS

Colllins et al., (Infect. Immun. 1991. vol. 59(3): 1079-1085).*
Bittner et al., (Microbial Pathogenesis. 2004 vol. 36:19-24).*
Nagy et al.(Infect. Immun. 2004. vol. 72(7): 4297-4301).*
Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in *Xenopus* oocytes. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.

(56) References Cited

OTHER PUBLICATIONS

Khan et al., Immunogenicity and protective efficacy of DnaJ (hsp40) of *Streptococcus pneumoniae* against lethal infection in mice Vaccine, 2006, pp. 6225-6231, vol. 24.

Kim et al., Direct transcriptional control of the plasminogen activator gene of *Yersinia pestis* by the cyclic AMP receptor protein. J Bacteriol, 2007, pp. 8890-8900, vol. 189.

Kolodrubetz et al., Regulation of the L-arabinose transport operons in *Escherichia coli*. J Mol Biol, 1981, pp. 215-227, vol. 151, No. 2.

Kwon et al., *Salmonella*-based vaccines for infectious diseases. Expert Review of Vaccines, 2007, pp. 147-152, vol. 6.

Lange et al., Identification of a central regulator of stationary-phase gene expression in *Escherichia coli*. Mol Microbiol, 1991, pp. 49-59, vol. 5.

Lee et al., Regulation of L-arabinose transport in *Salmonella typhimurium* LT2. Mol Gen Genet, 1982, pp. 136-141, vol. 185, No. 1.

Lee et al., Surface-displayed viral antigens on *Salmonella* carrier vaccine. Nat Biotechnol, 2000, pp. 645-648, vol. 18, No. 6.

Lewis, The lac repressor. C R Biol, 2005, pp. 521-548, vol. 328, No. 6.

Lobell et al., AraC-DNA looping: orientation and distance-dependent loop breaking by the cyclic AMP receptor protein. J Mol Biol, 1991, pp. 45-54, vol. 218.

Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.

Loessner et al., Bacteria-mediated DNA transfer in gene therapy and vaccination. Expert. Opin. Biol. Ther., 2004, pp. 157-168, vol. 4.

Loessner et al., Remote control of tumour-targeted *Salmonella enterica serovar* Typhimurium by the use of L-arabinose as inducer of bacterial gene expression in vivo. Cell Microbiol, 2007, pp. 1529-1537, vol. 9.

Marshall et al., Use of the stationary phase inducible promoters, spy and dps, to drive heterologous antigen expression in *Salmonella* vaccine strains. Vaccine, 2000, pp. 1298-1306, vol. 18, No. 14.

Medina et al., Use of live bacterial vaccine vectors for antigen delivery: potential and limitations. Vaccine, 2001, pp. 1573-1580, vol. 19.

Mehigh et al., Expression of the low calcium response in *Yersinia pestis*. Microb Pathog, 1989, pp. 203-217, vol. 6.

Moore et al., Enhanced protective immunity against Pneumococca infection with PspA DNA and protein. Vaccine, 2006, p. 5755, vol. 24.

Mossing et al., Upstream operators enhance repression of the lac promoter. Science, 1986, pp. 889-892, vol. 233, No. 4766.

Motin et al., Passive immunity to *Yersiniae* mediated by anti-recombinant V antigen and protein A-V antigen fusion peptide. Infect Immun, 1994, pp. 4192-4201, vol. 62.

Muller et al., Repression of lac promoter as a function of distance, phase and quality of an auxiliary lac operator. J Mol Biol, 1996, pp. 21-29, vol. 257, No. 1.

Muller-Hill et al., Mutants that mke more lac repressor. Proc Natl Acad Sci U S A, 1968, pp. 1259-1264, vol. 59, No. 4.

Muller-Hill, Lac repressor and lac operator. Prog Biophys Mol Biol, 1975, pp. 227-252, vol. 30, No. 2-3.

Nabors et al., Immunization of healthy adults with a single recombinant Pneumococcal surface protein A (PspA) variant stimulates broadly cross-reactive antibodies to heterologous PspA molecules. Vaccine, 2000, p. 1743, vol. 18.

Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.

Nedialkov et al., Resistance to Lipopolysaccharide mediated by the *Yersinia pestis* V antigen-polyhistidine fusion peptide: amplification of interleukin-10. Infect Immun, 1997, pp. 1196-1203, vol. 65.

Neutra et al., Antigen sampling across epithelial barriers and induction of mucosal immune responses. Annu Rev Immunol, 1996, pp. 275-300, vol. 14.

O'Callaghan et al., High efficiency transformation of *Salmonella typhimurium* and *Salmonella typhi* by electroporation. Mol Gen Genet, 1990, pp. 156-158, vol. 223, No. 1.

Ortqvist et al., Randomised trial of 23-valent Pneumococcal capsular polysaccharide vaccine in prevention of Pneumonia in middle-aged and elderly people. Swedish Pneumococcal Vaccination Study Group. Lancet, 1998, pp. 399-403, vol. 351.

Perry et al., Temperature regulation of the hemin storage (Hms+) phenotype of *Yersinia pestis* is posttranscriptional. J Bacteriol, 2004, pp. 1638-1647, vol. 186.

Petersen et al., Essential role for cyclic AMP and its receptor protein in *Yersinia enterocolitica* virulence. Infect Immun, 2004, pp. 3665-3672, vol. 70.

Ramarathinam et al., *Salmonella typhimurium* induces IFN-gamma production in murine splenocytes. Role of natural killer cells and macrophages. J Immunol, 1993, pp. 3973-3981, vol. 150.

Raupach et al., Bacterial virulence, proinflammatory cytokines and host immunity: how to choose the appropriate *Salmonella* vaccine strain? Microbes and Infection, 2001, p. 1261, vol. 3.

Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.

Sarubbi et al., (1989) Characterization of the spoT gene of *Escherichia coli*. J Biol Chem, 1989, pp. 15074-15082, vol. 264.

Schmieger et al., Altered cotransduction frequencies exhibited by HT-mutants of *Salmonella*-phage P22. Mol Gen Genet, 1976, pp. 307-309, vol. 143.

Schmieger, Phage P22-mutants with increased or decreased transduction abilities. Mol Gen Genet, 1972, pp. 75-88, vol. 119.

Schödel et al., Hybrid hepatitis B virus core antigen as a vaccine carrier moiety. II. Expression in avirulent *Salmonella* spp. For mucosal immunization. Adv Exp Med Biol., 1996, pp. 15-21, vol. 397.

Schodel, Prospects for oral vaccination using recombinant bacteria expressing viral epitopes. Adv. Virus Res., 1992, pp. 409-446, vol. 41.

Schwyn et al., Universal chemical assay for the detection and determination of siderophores. Analytical Biochemistry, 1987, p. 47, vol. 160.

Sedgwick et al., A solid-phase immunoenzymatic technique for the enumeration of specific antibody-secreting cells. Journal of Immunological Methods, 1983, p. 301, vol. 57.

Shalaby, Development of oral vaccines to stimulate mucosal and systemic immunity: barriers and novel strategies. Clin Immunol Immunopathol, 1995, pp. 127-134, vol. 74, No. 2.

U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 091686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.

(56) References Cited

OTHER PUBLICATIONS

U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
Nieto et al., Complex Structure of the nuclear translocation signal of influenza virus polymerase PA subunit. Journal of General Virology, 1994, pp. 29-36, vol. 75.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica serovar typhimurium*. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehydel Biol. Chem., 1955, pp. 39-50, vol. 213.
Briles et al., Immunization of humans with recombinant Pneumococcal surface protein a (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to Pneumococcal bacteremia. Infect. Immun., 1999, pp. 6533-6542, vol. 67.
Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in Peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide accines in the Absence of T and NK Cells. J Immunol, 1998, pp. 5525-5533, vol. 161.
Buchmeier, et al., DNA repair is more important than catalase for *Salmonella virulence* in mice. J. Clin. Invest., 1995, pp. 1047-1053, vol. 95.
Bumann, Regulated antigen expression in live recombinant *Salmonella enterica serovar typhimurium* strongly affects colonization capabilities and specific CD4(+)-T-cell responses. Infect Immun, 2001. pp. 7493-7500, vol. 69, No. 12.
Kotton et al., Enteric pathogens as vaccine vectors for foreign antigen delivery. Infect. Immun., 2004, pp. 5535-5547, vol. 72.
Lee et al., Characterization of recent H5 subtype avian influenza viruses from US poultry. Avian Pathol., 2004, pp. 288-297, vol. 33.
Lee et al., Mechanism of araC autoregulation and the domains of two overlapping promoters, PC and PBAD, in the L-arabinose regulatory region of *Escherichia coli*. Proc. Natl. Acad. Sci. U S A, 1981, pp. 752-756, vol. 78.
Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.
Lee et al., Trigger factor retards protein export in *Escherichia coli*. J Biol Chem, 2002, pp. 43527-43535, vol. 277.
Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.
Loessner et al., Differential effect of auxotrophies on the release of macromolecules by *Salmonella enterica* vaccine strains. FEMS Microbiol. Lett., 2006, pp. 81-88, vol. 265.
Loewen et al., Genetic mapping of katF, a locus that with katE affects the synthesis of a second catalase species in *Escherichia coli*. J Bacteriol, 1984, pp. 668-675, vol. 160.
Luytjes et al., Amplification, expression, and packaging of foreign gene by influenza virus. Cell, 1989, pp. 1107-1113, vol. 59.
Malley et al., CD4+ T cells mediate antibody-independent acquired immunity to *Pneumococcal colonization*. PNAS, 2005, pp. 4848-4853, vol. 102.
Massin et al., Cloning of the chicken RNA polymerase I promoter and use for reverse genetics of influenza A viruses in avian cells. J. Virol., 2005, pp. 13811-13816, vol. 79.
Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.
McClelland et al., Complete genome sequence of *Salmonella enterica serovar* typhimurium LT2. Nature, 2001, pp. 852-856, vol. 413, No. 6858.
McDaniel et al., Monoclonal antibodies against protease sensitive Pneumococcal antigens can protect mice from fatal infection with *Streptococcus pneumoniae*. J. Exp. Med., 1984, pp. 368-397, vol. 160.
McDaniel et al., Use of insertional inactivation to facilitate studies of biological properties of Pneumococcal surface protein A (PspA). J. Exp. Med., 1987, pp. 381-394, vol. 165.
Mesika et al., A regulated, NF κB-assisted import of plasmid DNA into mammalian cell nuclei. Mol. Ther., 2001, pp. 653-657, vol. 3.
Miller et al., A novel suicide vector and its use in construction of insertion mutations: osmoregulation of outer membrane proteins and virulence determinants in *Vibrio cholerae* requires toxR. J Bacteriol, 1988, pp. 2575-2583, vol. 170.
Miller et al., Bacteriophage T4 genome. Microbiol Mol Biol Rev, 2003, pp. 86-156, vol. 67, No. 1.
Molinari et al., Rhe annual impact of seasonal influenza in the US: measuring disease burden and costs. Vaccine, 2007, pp. 5086-5096, vol. 25.
Mulvey et al., Regulation of transcription of katE and katF in *Escherichia coli*. J Bacteriol, 1990, pp. 6713-6720, vol. 172.
Murti et al., Localization of RNA polymerases on influenza viral ribonucleoproteins by immunogold labeling. Virology, 1988, pp. 562-566, vol. 164.
Nardelli-Haefliger et al., Human papillomavirus type 16 virus-like particles expressed in attenuated *Salmonella typhimurium* elicit mucosal and systemic neutralizing antibodies in mice. Infect Immun, 1997, pp. 3328-3336, vol. 65.
Nayak et al., A live recombinant avirulent oral *Salmonella* vaccine expressing Pneumococcal surface protein a induces protective responses against *Streptococcus pneumoniae*. Infect Immun., 1998, pp. 3744-3751, vol. 66.
Neumann et al., An improved reverse genetics system for influenza A virus generation and its implications for vaccine production. Proc. Natl. Acad. Sci. USA, 2005, pp. 16825-16829, vol. 102.
Neumann et al., Generation of influenza A viruses entirely from cloned cDNAs. Proc. Natl. Acad. Sci. USA, 1999, pp. 9345-9350, vol. 96.
Neumann et al., RNA polymerase I-mediated expression of influenza viral RNA molecules. Virology, 1994, pp. 477-479, vol. 202.

(56) References Cited

OTHER PUBLICATIONS

Noda et al., Architecture of ribonucleoprotein complexes in influenza A virus particles. Nature, 2006, pp. 490-492, vol. 439.
Oehler et al., The three operators of the lac operon cooperate in repression. EMBO J, 1990, pp. 973-979, vol. 9, No. 4.
Ogunniyi et al., Contributions of Pneumolysin, Pneumococcal Surface Protein A (PspA), and PspC to Pathogenicity of Streptococcus pneumoniae D39 in a Mouse Model. Infect. Immun., 2007, pp. 1843-1851, vol. 75.
Osterholm, Preparing for the next pandemic. N. Engl. J. Med., 2005, pp. 1839-1842, vol. 352.
Ozaki et al., Generation of high-yielding influenza A viruses in African green monkey kidney (Vero) cells by reverse genetics. J. Virol., 2004, pp. 1851-1857, vol. 78.
Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic Escherichia coli Colonization Factor Antigen I by Salmonella typhimurium* Elicits a Biphasic T Helper Cell Response. Infect. Immun., 1999, pp. 6249-6256, vol. 67.
Pashine et al., Thi dominance in the immune response to live *Salmonella typhimurium* requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates *Salmonella* virulence nucleic acid sequence expression. Mol Microbiol, 2004, pp. 1827-1844, vol. 52, No. 6.
Prouty et al., *Salmonella enterica serovar typhimurium* invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of *Salmonella* strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a Pneumococcal conjugate vaccine, PncT, protect mice against invasive infection caused by *Streptococcus pneumoniae* serotypes 6A and 6B. J Infect Dis, 2001, pp. 253-260, vol. 183.
Hori et al, Constructionof selt-disruptive *Bacillus megaterium* in response to substrate exhaustion for polyhydroxybutryrate production. Appl Microbiol Biotechnol, 2002, pp. 211-216, vol. 59.
Houng et al., Expression of Vi antigen in *Escherichia coli* K-12: characterization of ViaB from *Citrobacter freundii* and identity of ViaA with RcsB. J.Bacterio, 1992, pp. 5910-5915, vol. 174, No. 18.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Simonsen et al., The impact of influenza epidemics on hospitalizations. J. Infect. Dis., 2000, pp. 831-837, vol. 181.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of Bordetella pertussis using an attenuated *Salmonella typhimurium* vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with Pneumococcal surface protein a and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from *Yersinia pestis* KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, The Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.
Coombes et al., SseL is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia*, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.

(56) References Cited

OTHER PUBLICATIONS

Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* KIM. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murI gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the *Yersinia pestis* Yfu ABC inorganic iron transport system. Infect Immun, 2001, pp. 2829-2837, vol. 69.
Gor et al., TH1-TH2: a Procrustean paradigm. Nat Immunol, 2003, p. 503-505, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
PCT/US2008/063303 (WO 2008/141226)—International Search Report and Written Opinion of the International Searching Authority, Nov. 26, 2008.
U.S. Appl. No. 12/759,842, Office Action dated Oct. 4, 2011.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.
PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.
PCT/US2011/038588 (WO 2011/150421)—International Search Report and Written Opinion of the International Searching Authority, Nov. 22, 2011.
PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.

(56) References Cited

OTHER PUBLICATIONS

European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of *Yersinia pestis* is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in *Yersinia pestis* include structural genes for outer membrane proteins. Infect Immun, 1986, pp. 445-454, vol. 51.
Sun et al., The role of relA and spoT in *Yersinia pestis* KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.
Une et al., In vivo comparison of avirulent Vwa- and Pgm- or Pstr phenotypes of *Yersiniae*. Infect Immun, 1984, pp. 895-900, vol. 43.
Uzzau et al., Epitope tagging of chromosomal genes in Salmonella. Proc Natl Acad Sci U S A, 2001, pp. 15264-15269, vol. 98.
Viboud et al., Yersinia outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica serotype typhi* regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in *Yersinia pestis*. Infect Immun, 1982, pp. 953-959, vol. 38.

Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in *Rhodococcus opacus* PD630 and *Mycobacterium smegmatis* mc2155, and provides an anchor to target other proteins. Microbiology, 2006, pp. 3271-3280, vol. 152.
Kong et al, Regulated Delayed Expression of rfaH in an Attenuated *Salmonella enterica serovar typhimurium* Vaccine Enhances Immunogenicity of Outer Membrane Proteins and Heterologous Antigen. Infec Immun. 2009, pp. 5572-5582, vol. 77, No. 12.
Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.
Morita et al., Antibacterial Activity of *Bacillus amyloliquefaciencs* Phage Endolysin without Holin Conjugation. Journal of Biosciences and Bioengineering, 2001, pp. 469-473, vol. 91, No. 5.
Navasa et al, Temperature has reciprocal effects on colanic acid and polysialic acid biosynthesis in *E. coli* K92. Appl Microbiol Biotechnol, 2009, pp. 721-729, vol. 82.
Stevens, Immunization with the C-Domain of alpha-Toxin Prevents Lethal Infection, Localizes Tissue Injury, and Promotes Host Responses to Challenge with *Clostridium perfringens*. JID, 2004, pp. 767-773, vol. 190.
Verjan et al, Genetic Loci of Major Antigenic Protein Genes of *Edwardsiella tarda*. Applied and Environmental Microbiology, 2005, pp. 5654-5658, vol. 71, No. 9.
U.S. Appl. No. 12/599,655 Office Action dated Jul. 2, 2012.
U.S. Appl. No. 12/681,721, Office Action dated May 24, 2012.
U.S. Appl. No. 12/759,842, Office Action dated Jun. 7, 2012.
Ellis, New Technologies for Making Vaccines. Vaccines, 1988, pp. 568-574, Chapter 29, WB Saunders Company, United States.
Greenspan et al, Defining eptiopes: It's not as easy as it seems. Nature Biotechnology, 1999, pp. 936-937, vol. 17.
Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25; Cold Spring Harbor Laboratory.
U.S. Appl. No. 12/615,872 Office Action dated Oct. 23, 2012.
PCT/US2011/061896—International Search Report and Written Opinion of the International Searching Authority, Apr. 5, 2012.
Spellberg et al., Type 1/type 2 immunity in infectious diseases. Clin. Infect. Dis., 2001, pp. 76-102, vol. 32.
Schnaitman et al., Genetics of Lipopolysaccharide biosynthesis in Enteric Bacteria. Microbiological Reviews, 1993, pp. 655-682, vol. 57, No. 3.
Byl et al, Sequence of the Genomore of *Salmonella* bacteriophage P22. Journal of Bacteriology, 2000, pp. 6472-6484, vol. 182, 22.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.

(56) References Cited

OTHER PUBLICATIONS

Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infect.Immun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica Servoar typhimurium*. Journal of Bacteriology, 2009, pp. 1278-1292, vol. 191, No. 4.
U.S. Appl. No. 12/615,872, Office Action dated Mar. 14, 2012.
Collins et al, Mutation at rfc or pmi Attenuate *Salmonella typhimurium* Virulence for Mice. Infect and Immun, 1991, pp. 1079-1085, vol. 59, No. 3.
Curtiss et al., Stabilization of Recombinant Avirulent Vaccine Strains in vivo. Res. Microbiol., 1990, pp. 797-805, vol. 141.
Curtiss et al, Avirulent *Salmonell typhimurim* cyc crp oral vaccine strains expressing a Streptococcal colonization and virulence antigen. Vaccine, 1988, pp. 155-160, vol. 6.
Darzins et al., Nucleotide sequence analysis of the phosphomannose isomerase gene (pmi) of *Pseudomonas aeruginose* and comparison with the corresponding *Escherichia coli* gene manA. Gene, 1986, pp. 293-302, vol. 42.
Doggett et al., Immune Responses to *Streptococcus sobrinus* Surface Protein Antigen A Expressed by Recombinant *Salmonella typhimurium*. Infect and Immun, 1993, pp. 1859-1866, vol. 61, No. 5.
Egan et al., A Regulatory Cascade in the Induction of rhaBAD. J. Mol. Biol., 1993, pp. 87-98, vol. 234.
Guzman et al., Tight regulations, Modulations, and High-Level Expression by Vectors Containing the Arabinose Pbad Promotor. Journal of Bacteriology, 1995, pp. 4121-4130, vol. 177, No. 14.
Kennedy et al., Attenuation and Immunogenicity of cya crp Derivatives of *Salmonella choleraeuis* in Pigs. Infect Immun, 1999, pp. 4628-4636, vol. 67, No. 9.
Nickerson et al., Role of Sigma Factor RpoS in Initial Stages of *Salmonella typhimurium* Infection. Infect Immun, 1997, p. 1814-1823, vol. 65, No. 5.
Schodel et al., Hybrid Hepatitis B Virus Core-Pre-S Proteins Synthesized in Avirulent *Salmonella typhimurium* and *Salmonella typhi* for Oral Vaccination. Infect Immun, 1994, pp. 1669-1676, vol. 62, No. 5.
Schodel, Recombinant Avirulent Salmonellae as Oral Vaccine Carriers. Infection, 1992, pp. 5-12, No. 1.
Siegele et al., Gene Expression from plasmids containing the araBAD promoter at subsaturating inducer concentrations represents mixed populations. PNAS, 1997, pp. 8168-8172, vol. 94.
Song et al., Organization and Regulation of the d-Xylose Operons in *Escherichia coli* K-12: XylR Acts as a Transcriptional Activator. Journal of Bacteriology, 1997, pp. 7025-7032, vol. 197, No. 22.
Srinivasan et al., Oral Immunization with Attenuated *Salmonella* Expressing Human Sperm Antigen Induces Antibodies in Serum and the Reproductive Tract. Biology of Reproduction, 1995, p. 462-471 vol. 53.
PCT/US2008/063293 (WO 2009/025888)—International Search Report and Written Opinion of the International Searching Authority, Feb. 12, 2009.
CDC, Update: influenza activity—United States, Sep. 30, 2007-Apr. 5, 2008, and composition of the Sep. 2008 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
U.S. Appl. No. 13/006,072, Office Action dated Apr. 19, 2012.
Sun et al., Highly efficient method for introducing successive multiple scarless gene deletions and markerless gene insertions into the *Yersinia pestis* chromosome. Appl Environ Microbiol, 2008, pp. 4241-4245, vol. 74.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Waltman et al., Biochemical Characteristics of *Edwardsiella ictaluri*. Applied and Enviornmental Microbiology, 1986, pp. 101-104, vol. 51, No. 1.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (SCOTS). Mol Microbiol, 2001, pp. 1211-1222, vol. 41.
Takaya et al., The ATP-Dependent Lon Protease of *Salmonella enterica serovar typhimurium* Regulates Invasion and Expression of Genes Carried on *Salmonella* Pathogenicity Island 1. Journal of Bacteriology, 2002, pp. 224-232, vol. 184, No. 1.
Dean, 1997. Import of plasmid DNA into the nucleus is sequence specific. Exp. Cell Res., 1997, pp. 293-302, vol. 230.
Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella typhimurium* expressing a cloned Porphyromonas gingivalis hemagglutinin. Infect Immun, 1994, pp. 1652-1657, vol. 62, No. 5.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of *Shigella sonnei* form I antigen genes into the galE *Salmonella typhi* Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.

(56) References Cited

OTHER PUBLICATIONS

Galan et al., Cloning and molecular characterization of genes whose products allow *Salmonella typhimurium* to penetrate tissue culture cells. Proc Natl Acad Sci U S A, 1989, pp. 6383-6387, vol. 86.
Galen et al., Optimization of Plasmid Maintenance in the Attenuated Live Vector Vaccine Strain *Salmonella typhi* CVD 908-htrA. Infect. Immun., 1999, pp. 6424-6433, vol. 67.
Garmory et al., Antibiotic-free plasmid stabilization by operator-repressor titration for vaccine delivery by using live *Salmonella enterica serovar typhimurium*. Infect. Immun., 2005, pp. 2005-2011, vol. 73.
Gay et al., Positive selection procedure for entrapment of insertion sequence elements in gram-negative bacteria. J Bacteriol, 1985, pp. 918-921, vol. 164, No. 2.
Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.
Gerdil, The annual production cycle for influenza vaccine. Vaccine, 2003, pp. 1776-1779, vol. 21.
Ghany et al. Candidate live, attenuated *Salmonella enterica serotype typhimurium* vaccines with reduced fecal shedding are immunogenic and effective oral vaccines. Infect. Immun., 2007, pp. 1835-1842, vol. 75.
Greenwood, The epidemiology of Pneumococcal infection in children in the developing world. Philos. Trans. R. Soc. Lond. B. Biol. Sci., 1999, pp. 777-785, vol. 354.
Gulig et al., Plasmid-associated virulence of *Salmonella typhimurium*. Infect Immun, 1987, pp. 2891-2901, vol. 55.
Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.
Hall et al., The role of fur in the acid tolerance response of *Salmonella typhimurium* is physiologically and genetically separable from its role in iron acquisition. J Bacteriol, 1996, pp. 5683-5691, vol. 178.
Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.
Hicks et al., Incidence of *Pneumococcal* disease due to non-pneumococcal conjugate vaccine (PCV7) serotypes in the United States during the era of widespread PCV7 vaccination, 1998-2004. J Infect Dis, 2007, pp. 1346-1354, vol. 196.
Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.
Hoffmann et al., "Ambisense" approach for the generation of influenza A virus: vRNA and mRNA synthesis from one template. Virology, 2000, pp. 310-317, vol. 267.
Hohmann et al., Macrophage-inducible expression of a model antigen in *Salmonella typhimurium* enhances immunogenicity. Proc Natl Acad Sci U S A, 1995, pp. 2904-2908, vol. 92, No. 7.
Hollingshead et al., Diversity of PspA: mosaic genes and evidence for past recombination in *Streptococcus pneumoniae*. Infect Immun., 2000, pp. 5889-5900, vol. 68.
Hopkins et al., A recombinant *Salmonella typhimurium* vaccine induces local immunity by four different routes of immunization. Infect Immun, 1995, pp. 3279-3286, vol. 63.

Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.
Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.
Kang et al., Immune responses to recombinant *Pneumococcal* PspA antigen delivered by live attenuated *Salmonella enterica serovar typhimurium* vaccine. Infect. Immun., 2002, pp. 1739-1749, vol. 70.
Kang et al., Transduction-mediated transfer of unmarked deletion and point mutations through use of counterselectable suicide vectors. J Bacteriol, 2002, pp. 307-312, vol. 184.
Katzman et al., Invertebrate connective tissue. Isolation of D-arabinose from sponge acidic polysaccharide. Biochem J, 1970, pp. 17-19, vol. 119, No. 1.
Hurme et al, A Proteinaceous Gene Regulator Thermameter in *Salmonella*. Cell, 1997, pp. 55-64, vol. 90.
Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.
Klumpp et al., Roles of the influenza virus polymerase and nucleoprotein in forming a functional RNP structure. EMBO J., 1997, pp. 1248-1257, vol. 16.
Kong et al, Regulated programmed lysis of recombinant *Salmonella* in host tissues to release protective antigens and confer biological containment. PNAS, 2008, pp. 9361-9366, vol. 105, No. 27.
Konjufca et al., A Recombinant Attenuated *Salmonella enterica serovar typhimurium* Vaccine Encoding *Eimeria acervulina* Antigen Offers Protection against *E. acervulina* Challenge. Infect. Immun., 2006, pp. 6785-6796, vol. 74.
Quenee, Lauriane E., et al., *Yersinia pestis* caf1 Variants and the Limits of Plague Vaccine Protection, Infection and Immunity, May 2008, vol. 76, No. 5, pp. 2025-2036.
U.S. Appl. No. 13/088,141, Office Action dated Dec. 6, 2012.
U.S. Appl. No. 13/006,072, Office Action dated Dec. 11, 2012.
Kong, W., T-10-, Improving DNA Vaccine Vector for Efficient Vaccine Delivery Using Live Attenuated Bacterial Carrier, The Society, vol. 2008, No. 108, pp. 668.
Mesika, Adi, et al., A Regulated, NF kB-Assisted Import of Plasmid DNA into Mammalian Cell Nuclei, Molecular Therapy, vol. 3, No. 5, May 2001, pp. 653-657.
Ribeiro, Sofia C., et al., The Role of Polyadenylation Signal Secondary Structures on the Resistance of Plasmid Vectors to Nucleases, The Journal of Gene Medicine, vol. 6, 2004, pp. 565-573.
Rytkonen, Anne, et al.,. SseL, a *Salmonella* Deubiquitinase Required for Macrophage Killing and Virulence, PNAS, vol. 104, No. 9, Feb. 27, 2007, pp. 3502-3507.
Wang, Shixia, et al., Hemagglutinin (HA) Proteins from H1 and H3 Serotypes of Influenza a Viruses Require Different Antigen Designs for the Induction of Optimal Protective Antibody Responses as Studied by Codon-Optimized HA DNA Vaccines, Journal of Virology, vol. 80, No. 23, Dec. 2006, pp. 11628-11637.
U.S. Appl. No. 13/302,575, Office Action dated Sep. 25, 2012.
U.S. Appl. No. 12/615,872, Office Action dated Oct. 23, 2012.
American Society of Microbiology, vol. 108; 2008: (p. 668).

* cited by examiner

```
                       SEQUENCE LISTING

<160> NUMBER OF SEQ ID NOS: 27

<210> SEQ ID NO 1
<211> LENGTH: 19
<212> TYPE: DNA
<213> ORGANISM: Artificial Sequence
<220> FEATURE:
<223> OTHER INFORMATION: SALMONELLA

<400> SEQUENCE: 1
ctcgagagga gtcattatg                                                  19

<210> SEQ ID NO 2
<211> LENGTH: 19
<212> TYPE: DNA
<213> ORGANISM: Artificial Sequence
<220> FEATURE:
<223> OTHER INFORMATION: SALMONELLA

<400> SEQUENCE: 2
ctcgagaaga gtcattgtg                                                  19

<210> SEQ ID NO 3
<211> LENGTH: 19
<212> TYPE: DNA
<213> ORGANISM: Artificial Sequence
<220> FEATURE:
<223> OTHER INFORMATION: SALMONELLA

<400> SEQUENCE: 3
ctcgagagga gtcattatg                                                  19

<210> SEQ ID NO 4
<211> LENGTH: 20
<212> TYPE: DNA
<213> ORGANISM: Artificial Sequence
<220> FEATURE:
<223> OTHER INFORMATION: SALMONELLA

<400> SEQUENCE: 4
actcgagagg agtcattgtg                                                 20

<210> SEQ ID NO 5
<211> LENGTH: 19
<212> TYPE: DNA
<213> ORGANISM: Artificial Sequence
<220> FEATURE:
<223> OTHER INFORMATION: SALMONELLA
```

```
<400> SEQUENCE: 5
ctcgaggagg gtcattgtg                                                    19

<210> SEQ ID NO 6
<211> LENGTH: 38
<212> TYPE: DNA
<213> ORGANISM: Artificial Sequence
<220> FEATURE:
<223> OTHER INFORMATION: SALMONELLA

<400> SEQUENCE: 6
actgcctgca gcccgggctt aaactgcggc agcttgtc                               38

<210> SEQ ID NO 7
<211> LENGTH: 32
<212> TYPE: DNA
<213> ORGANISM: Artificial Sequence
<220> FEATURE:
<223> OTHER INFORMATION: SALMONELLA

<400> SEQUENCE: 7
actgcctgca gcttcatcct ttaagccgta tc                                     32

<210> SEQ ID NO 8
<211> LENGTH: 37
<212> TYPE: DNA
<213> ORGANISM: Artificial Sequence
<220> FEATURE:
<223> OTHER INFORMATION: SALMONELLA

<400> SEQUENCE: 8
atgcactcga gaggagtcat tatgcaatcc tggtatt                                37

<210> SEQ ID NO 9
<211> LENGTH: 31
<212> TYPE: DNA
<213> ORGANISM: Artificial Sequence
<220> FEATURE:
<223> OTHER INFORMATION: SALMONELLA

<400> SEQUENCE: 9
cgacggtacc ggttgtattc tgaacgatcg c                                      31

<210> SEQ ID NO 10
<211> LENGTH: 37
<212> TYPE: DNA
<213> ORGANISM: Artificial Sequence
<220> FEATURE:
<223> OTHER INFORMATION: SALMONELLA

<400> SEQUENCE: 10
atgcactcga gaagagtcat tatgcaatcc tggtatt                                37

<210> SEQ ID NO 11
<211> LENGTH: 37
<212> TYPE: DNA
<213> ORGANISM: Artificial Sequence
<220> FEATURE:
<223> OTHER INFORMATION: SALMONELLA

<400> SEQUENCE: 11
atgcactcga gaagagtcat tgtgcaatcc tggtatt                                37

<210> SEQ ID NO 12
```

<211> LENGTH: 30
<212> TYPE: DNA
<213> ORGANISM: Artificial Sequence
<220> FEATURE:
<223> OTHER INFORMATION: SALMONELLA

<400> SEQUENCE: 12
actgggtacc ccatcgccac gcgttttggc                                        30

<210> SEQ ID NO 13
<211> LENGTH: 37
<212> TYPE: DNA
<213> ORGANISM: Artificial Sequence
<220> FEATURE:
<223> OTHER INFORMATION: SALMONELLA

<400> SEQUENCE: 13
tgaacgatcg cctgcaggaa tgactcttat ccgcttg                                37

<210> SEQ ID NO 14
<211> LENGTH: 36
<212> TYPE: DNA
<213> ORGANISM: Artificial Sequence
<220> FEATURE:
<223> OTHER INFORMATION: SALMONELLA

<400> SEQUENCE: 14
agtcattcct gcaggcgatc gttcagaata caacct                                 36

<210> SEQ ID NO 15
<211> LENGTH: 30
<212> TYPE: DNA
<213> ORGANISM: Artificial Sequence
<220> FEATURE:
<223> OTHER INFORMATION: SALMONELLA

<400> SEQUENCE: 15
atctcccggg ttatgcactg ccgggacgcg                                        30

<210> SEQ ID NO 16
<211> LENGTH: 21
<212> TYPE: DNA
<213> ORGANISM: Artificial Sequence
<220> FEATURE:
<223> OTHER INFORMATION: SALMONELLA

<400> SEQUENCE: 16
atcacaattc taggatagaa t                                                 21

<210> SEQ ID NO 17
<211> LENGTH: 37
<212> TYPE: DNA
<213> ORGANISM: Artificial Sequence
<220> FEATURE:
<223> OTHER INFORMATION: SALMONELLA

<400> SEQUENCE: 17
actgcctgca gcccgggtct ttctgttcta cagaacc                                37

<210> SEQ ID NO 18
<211> LENGTH: 31
<212> TYPE: DNA
<213> ORGANISM: Artificial Sequence
<220> FEATURE:
<223> OTHER INFORMATION: SALMONELLA

<400> SEQUENCE: 18
actgcctgca gagattcatc atgaggttcc c    31

<210> SEQ ID NO 19
<211> LENGTH: 29
<212> TYPE: DNA
<213> ORGANISM: Artificial Sequence
<220> FEATURE:
<223> OTHER INFORMATION: SALMONELLA

<400> SEQUENCE: 19
atgcactcga gaggactcta tatgcttat    29

<210> SEQ ID NO 20
<211> LENGTH: 32
<212> TYPE: DNA
<213> ORGANISM: Artificial Sequence
<220> FEATURE:
<223> OTHER INFORMATION: SALMONELLA

<400> SEQUENCE: 20
acggaggtac cctctctgaa ctccatcaac ac    32

<210> SEQ ID NO 21
<211> LENGTH: 35
<212> TYPE: DNA
<213> ORGANISM: Artificial Sequence
<220> FEATURE:
<223> OTHER INFORMATION: SALMONELLA

<400> SEQUENCE: 21
atgcactcga gaggactcta tgtgcttata atttc    35

<210> SEQ ID NO 22
<211> LENGTH: 34
<212> TYPE: DNA
<213> ORGANISM: Artificial Sequence
<220> FEATURE:
<223> OTHER INFORMATION: SALMONELLA

<400> SEQUENCE: 22
atgcactcga gaggctctat gtgcttataa tttc    34

<210> SEQ ID NO 23
<211> LENGTH: 21
<212> TYPE: DNA
<213> ORGANISM: Artificial Sequence
<220> FEATURE:
<223> OTHER INFORMATION: SALMONELLA

<400> SEQUENCE: 23
atcacaattc taggatagaa t    21

<210> SEQ ID NO 24
<211> LENGTH: 30
<212> TYPE: DNA
<213> ORGANISM: Artificial Sequence
<220> FEATURE:
<223> OTHER INFORMATION: SALMONELLA

<400> SEQUENCE: 24
ctgcctgcag aagtatgtcg cggcacgatg    30

<210> SEQ ID NO 25
<211> LENGTH: 37
<212> TYPE: DNA

```
<213> ORGANISM: Artificial Sequence
<220> FEATURE:
<223> OTHER INFORMATION: SALMONELLA

<400> SEQUENCE: 25
ataacttacc tgcaggatag agcctttaga aaaaatg                              37

<210> SEQ ID NO 26
<211> LENGTH: 37
<212> TYPE: DNA
<213> ORGANISM: Artificial Sequence
<220> FEATURE:
<223> OTHER INFORMATION: SALMONELLA

<400> SEQUENCE: 26
ggctctatcc tgcaggtaag ttatacggcg gcaatgc                              37

<210> SEQ ID NO 27
<211> LENGTH: 31
<212> TYPE: DNA
<213> ORGANISM: Artificial Sequence
<220> FEATURE:
<223> OTHER INFORMATION: SALMONELLA

<400> SEQUENCE: 27
atctcccggg gttcgtttaa acctgtttca c                                   31
```

BACTERIUM COMPRISING A REGULATED RFAH NUCLEIC ACID

FIELD OF THE INVENTION

The present invention encompasses a recombinant bacterium comprising a regulated rfaH nucleic acid. Additionally, the invention encompasses a recombinant bacterium comprising both a regulated rfaH and a regulated rfc nucleic acid.

BACKGROUND OF THE INVENTION

When recombinant attenuated *Salmonella* vaccines (RASV) are used to deliver heterologous antigens, it may be advantageous to reduce the host immune response against the RASV carrier, thereby enhancing the immune response against the heterologous antigen. The dominant immunogen on the *Salmonella* cell surface is lipopolysaccharide (LPS) O-antigen. However, strains with mutations that eliminate LPS O-antigen may be less immunogenic due to failure of these kinds of mutants to colonize the intestinal tract and invade intestinal mucosal cells. Hence, there is a need in the art for a bacterium that comprises a mutation that allows O-antigen synthesis, yet still reduces the host immune response against the bacterium. This feature would also contribute to the potential use of the RASV vector for multiple vaccines to prevent against multiple infectious disease agents.

SUMMARY OF THE INVENTION

One aspect of the present invention encompasses a recombinant bacterium comprising a regulated rfaH nucleic acid.

Another aspect of the present invention encompasses a recombinant bacterium comprising a regulated rfaH nucleic acid, and at least one nucleic acid sequence encoding at least one exogenous antigen.

Yet another aspect of the present invention encompasses a recombinant bacterium comprising a regulated rfaH nucleic acid and a regulated rfc nucleic acid.

A further aspect of the invention encompasses a vaccine. Generally speaking, the vaccine comprises a recombinant bacterium comprising a regulated rfaH nucleic acid.

Other aspects and iterations of the invention are described more thoroughly below.

DETAILED DESCRIPTION OF THE INVENTION

Figure 1:
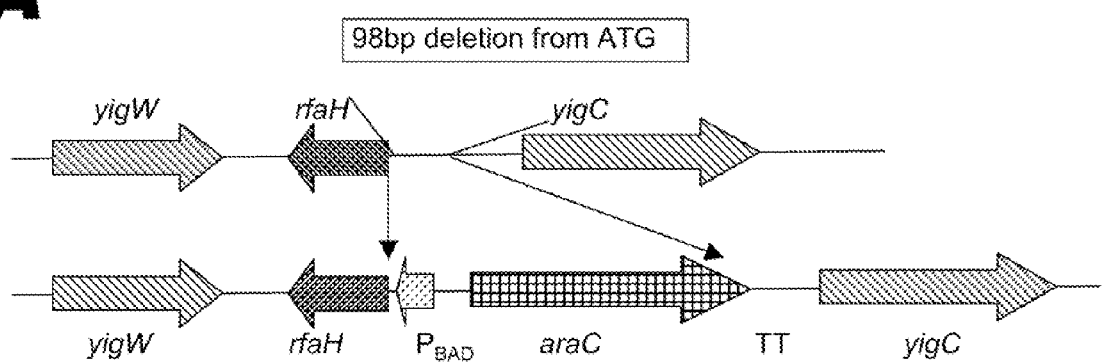
FIG. 1. Arabinose regulation of rfaH. (A) map for deletion-insertion mutations resulting in arabinose-regulated rfaH expression. (B) lipopolysaccharide (LPS) phenotypes of wild-type *S. Typhimurium* UK-1 χ3761 and the indicated isogenic derivatives. LPS from different mutant strains grown in Nutrient Broth with/without 0.1% arabinose were silver stained after separation by 12% SDS-PAGE. (C) western blots of LPS preparations from B. Blots were probed with anti-*Salmonella* group B O-antigen antibodies.
Figure 1:
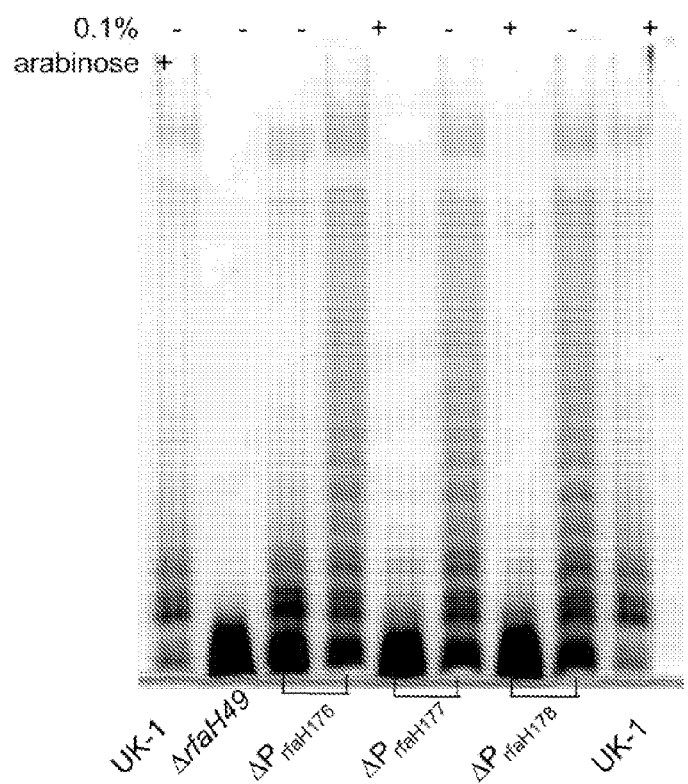

The present invention provides a recombinant bacterium comprising a regulated rfaH nucleic acid. Regulation of the expression of a rfaH nucleic acid allows the downregulation of O-antigen synthesis after growth of the bacterium in a host. This allows increased host immune responses to the exogenous antigen. In some embodiments, the recombinant bacterium further comprises at least one nucleic acid sequence encoding at least one exogenous antigen.

The invention also encompasses a vaccine composition comprising the recombinant bacterium of the invention and methods for using the recombinant bacterium.

I. Recombinant Bacterium

One aspect of the present invention encompasses a recombinant bacterium comprising a regulated rfaH nucleic acid. Alternatively, a recombinant bacterium of the invention may comprise both a regulated rfaH nucleic acid and a regulated rfc nucleic acid. Generally speaking, the bacterium may be any bacterium capable of expressing rfaH or a homolog thereof. As used herein, "homolog" refers to a nucleic acid sequence that has at least 50% homology to rfaH and encodes a protein with a substantially similar function as the protein encoded by rfaH. In one embodiment, a homolog has at least 60, 65, 70, 75, 80, 85, 90, or 95% homology to rfaH. In another embodiment, a homolog has at least 80, 81, 82, 83, 84, 85, 86, 87, 88, 89, 90, 91, 92, 93, 94, 95, 96, 97, 98, or 99% homology to rfaH. Methods of determining percent homology are known in the art. For instance, NBLAST may be used to determine percent homology between two nucleic acid sequences.

Generally speaking, a regulated rfaH nucleic acid reduces LPS O-antigen. This reduction provides the host immune system with better access to the outer membrane proteins of the recombinant bacterium, thereby enhancing induction of immune responses against these outer membrane proteins. In some embodiments, the outer membrane proteins may be upregulated to further enhance host immune responses to these proteins. Non-limiting examples of outer membrane proteins may include proteins involved in iron and manganese uptake. Iron and manganese are essential nutrients for exogenous pathogens and the induction of antibodies that inhibit iron and manganese uptake in effect starves the pathogens, conferring protective immunity on the host. Additionally, since these proteins are substantially homologous among bacteria, such a host immune response provides immunity against more than one *Salmonella* serotype as well as against other bacterial pathogens such as strains of *Yersinia*, *Shigella* and *Escherichia*.

A recombinant bacterium of the invention may further comprise at least one nucleic acid sequence encoding at least one exogenous antigen.

In some embodiments, the recombinant bacterium is gram negative. In certain embodiments, the recombinant bacterium may be *Salmonella*. In an exemplary embodiment, a bacterium of the invention may be derived from *S. Typhimurium, S. Typhi, S. Paratyphi, S. Gallinarum, S. Enteritidis, S. Choleraesius, S. Arizonae,* or *S. Dublin*. In another exemplary embodiment, a bacterium of the invention may be derived from *S. Typhimurium, S. Paratyphi,* or *S. Typhi*. In all cases, a recombinant bacterium of the invention generally does not comprise any drug resistance nucleic acid sequences or other sequence scars in the chromosomes of the recombinant strain.

(a) Regulated rfaH

A recombinant bacterium may comprise a regulated rfaH nucleic acid. As used herein, "regulated" refers to a chromosomally integrated nucleic acid sequence encoding rfaH operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

A regulated promoter used herein generally allows transcription of the rfaH nucleic acid sequence while in a permissive environment (i.e. in vitro growth), but ceases transcription of the rfaH nucleic acid sequence while in a non-permissive environment (i.e. during growth of the bacterium in an animal or human host). For instance, the promoter may be sensitive to a physical or chemical difference between the permissive and non-permissive environment. Suitable examples of such regulatable promoters are described in detail below, and other examples are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other bacteria contain arabinose regulatory systems homologous to the araC araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. Typhimurium* $P_{BAD}$. Thus, an arabinose-regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In an exemplary embodiment, a regulated rfaH nucleic acid may be $\Delta P_{rfaH176}$::TT araC $P_{BAD}$ rfaH. In another exemplary embodiment, a regulated rfaH nucleic acid may be $\Delta P_{rfaH177}$::TT araC $P_{BAD}$ rfaH. In yet another exemplary embodiment, a regulated rfaH nucleic acid may be $\Delta P_{rfaH178}$::TT araC $P_{BAD}$ rfaH.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the ma/EFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ rhaBAD promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the $P_{rhaRS}$ promoter and activates the production of RhaR and RhaS. RhaS together with L-rhamnose in turn binds to the $P_{rhaBAD}$ and the $P_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rhaBAD}$ promoter.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xylR-$P_{xylAB}$ and/or xylR-$P_{xylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

i. Modification to Optimize Expression

A nucleic acid sequence encoding rfaH and a regulatable promoter detailed above, for use in the present invention, may be modified so as to optimize the expression level of rfaH. The optimal level of expression of the rfaH nucleic acid sequence may be estimated or may be determined by experimentation. In an exemplary embodiment, the level of expression is optimized so that RfaH is synthesized while in the permissive environment (i.e. in vitro growth) at a level that substantially allows the synthesis of O-antigen, and is substantially not synthesized in a non-permissive environment, thereby substantially reducing the synthesis of O-antigen.

As stated above, the level of expression may be optimized by modifying the rfaH nucleic acid sequence. As used herein, "modify" refers to an alteration of the rfaH nucleic acid sequence and/or promoter that results in a change in the level of transcription of the rfaH nucleic acid sequence, or that results in a change in the level of synthesis of RfaH. For instance, in one embodiment, modify may refer to altering the start codon of the rfaH nucleic acid sequence. Generally speaking, a GTG or TTG start codon, as opposed to an ATG start codon, may decrease translation efficiency ten-fold. In another embodiment, modify may refer to altering the Shine-Dalgarno (SD) sequence of the rfaH nucleic acid sequence. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences.

In some embodiments, more than one modification or type of modification may be performed to optimize the expression level of the rfaH nucleic acid sequence. For instance, at least one, two, three, four, five, six, seven, eight, or nine modifications, or types of modifications, may be performed to optimize the expression level of the rfaH nucleic acid sequence.

In an exemplary embodiment, when the rfaH nucleic acid with regulated expression is $\Delta P_{rfaH176}$::TT araC $P_{BAD}$ rfaH, the SD sequence may be AGGA and the start codon may be ATG. In another exemplary embodiment, when the rfaH nucleic acid with regulated expression is $\Delta P_{rfaH177}$::TT araC $P_{BAD}$ rfaH, the SD sequence may be AAGA and the start codon may be ATG. In yet another exemplary embodiment, the rfaH nucleic acid with regulated expression may be $\Delta P_{rfaH178}$::TT araC $P_{BAD}$ rfaH, the SD sequence may be AAGA and the start codon may be GTG.

Methods of modifying a rfaH nucleic acid sequence and/or a regulatable promoter are known in the art and detailed in the examples.

ii. Transcription Termination Sequence

In some embodiments, the chromosomally integrated rfaH nucleic acid sequence further comprises a transcription termination sequence. A transcription termination sequence may be included to prevent inappropriate expression of nucleic acid sequences adjacent to the chromosomally integrated nucleic acid sequence and regulatable promoter.

(b) Nucleic Acid Encoding at Least One Exogenous Antigen

Generally speaking, a recombinant bacterium of the invention comprises at least one nucleic acid encoding at least one exogenous antigen. As used herein, the phrase "exogenous antigen" refers to an antigen that elicits an immune response against a pathogen other than the serovar of the recombinant bacterium itself. Non-limiting examples of exogenous antigens from *Yersinia* may include the V antigen and the psn nucleic acid product involved in iron acquisition. Non-limiting examples of exogenous antigens from *E. coli* may include salmochelin, aerobactin, the sit operon antigens involved in iron and manganese uptake, the fimbriae encoded by the yagZ fimbrial operon, other fimbriae encoded by nucleic acids in various ETEC, EPEC, EHEC, APEC, UPEC and/or ExPEC strains, the tsh nucleic acid product, the iss nucleic acid product, and LT-B, the non-toxic cell binding domain of the LT toxin. Non-limiting examples of exogenous antigens from *Shigella* may include the IpaD and aerobactin antigens. Non-limiting examples of exogenous antigens from *C. jejuni* may include PilA and CjaA antigen. Non-limiting examples of exogenous antigens from *C. perfringens* may include the α-toxin and NetB antigens.

It is not necessary that the nucleic acid encoding an exogenous antigen comprise the complete nucleic acid sequence of the antigen. It is only necessary that the exogenous antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular exogenous antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In certain embodiments, an exogenous antigen of the invention may comprise a B cell epitope or a T-cell epitope. Alternatively, an antigen to which an immune response is desired may be expressed as a fusion to a carrier protein that contains a strong promiscuous T-cell epitope and/or serves as an adjuvant and/or facilitates presentation of the antigen to enhance, in all cases, the immune response to the antigen or its component part. This can be accomplished by methods known in the art. Fusion to tetanus toxin fragment C, CT-B, LT-B, hepatitis virus B core, and woodchuck hepatitis virus core are particularly useful for these purposes, although other epitope presentation systems are well known in the art.

In certain embodiments, the expression of at least one nucleic acid encoding at least one exogenous antigen may be regulated. In further embodiments, a nucleic acid sequence encoding an antigen of the invention may comprise a secretion signal. In other embodiments, an antigen of the invention may be toxic to the recombinant bacterium.

A recombinant bacterium may comprise a long sequence of nucleic acid encoding several nucleic acid sequence products, one or all of which may be exogenous antigens. In some embodiments, the expression of at least one, at least two, at least three, at least four, at least five, at least six, or more nucleic acids encoding exogenous antigens is regulated in a bacterium of the invention. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein. In another alternative, the two or more antigens may be encoded by overlapping open reading frames.

In many cases, the high level expression of a nucleic acid sequence encoding an antigen in a bacterium reduces the bacterium's fitness, such that the bacterium grows slowly, is susceptible to stresses encountered in the host, and is generally less able to effectively colonize effector lymphoid tissues. High level expression of a nucleic acid sequence encoding an antigen, however, is highly desirable to maximize induction of an immune response against the antigen. Consequently, the phrase "regulated expression of at least one nucleic acid encoding at least one exogenous antigen" refers to expression of at least one nucleic acid encoding at least one exogenous antigen in a bacterium such that the bacterium is capable of colonizing a host at levels similar to a wild-type bacterium, and yet is still capable of eliciting an immune response against an exogenous pathogen when administered to the host. Methods of expressing, or regulating the expression of, at least one nucleic acid encoding at least one exogenous antigen include the regulated expression system detailed in section I. (a) above and the methods detailed in the examples. Additionally, the exogenous antigen of interest may be encoded on an extra-chromosomal vector. This can be used in the context of a balanced-lethal host-vector or balanced-attenuation host-vector system. Alternatively, the nucleotide sequence encoding the antigen of interest may be inserted into the chromosome but have its expression controlled by a regulatable system, e.g., LacI or C2, as with the regulated gene encoding the antigen of interest on an extra-chromosomal vector (e.g., a plasmid).

(c) Attenuation of the Recombinant Bacterium

In each of the above embodiments, a recombinant bacterium of the invention may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the gastrointestinal tract (in the case of *Salmonella*) and induce immune responses is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of lymphoid tissues before the recombinant bacterium is regulated to display the attenuated phenotype.

In one embodiment, a recombinant bacterium may be attenuated by regulating LPS O-antigen. In certain embodiments, both regulated attenuation and regulated expression of an exogenous antigen encoding sequence may be dependent upon an arabinose regulatable system. Consequently, the concentration of arabinose needed for optimal expression of the regulated exogenous antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

Other methods of attenuation are known in the art. For instance, attenuation may be accomplished by altering (e.g., deleting) native nucleic acid sequences found in the wild-type bacterium. For instance, if the bacterium is Salmonella, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall.

Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

When arabinose is absent, however, as it is in an animal or human host, the essential constituent of the peptidoglycan layer of the cell wall is not synthesized. This mutation represents an arabinose dependant lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, cannot be exogenously supplied because exogenous bacteria cannot take the nutrient up from the media. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid.

Similarly, various embodiments may comprise the araC $P_{BAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above.

In one embodiment, ΔasdA27::TT araC $P_{BAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{BAD}$ c2 has the 1104 base-pair asd nucleic acid sequence deleted (1 to 1104, but not including the TAG stop codon) and the 1989 base-pair fragment containing T4 ipIII TT araC $P_{BAD}$ c2 inserted. The c2 nucleic acid sequence in ΔasdA27::TT araC $P_{BAD}$ c2 has a SD sequence that was optimized to TAAGGAGGT. It also has an improved $P_{BAD}$ promoter such that the −10 sequence is improved from TACTGT to TATAAT. Furthermore, it has a codon optimized c2 nucleic acid sequence, in which the second codon was modified from AAT to AAA.

In further embodiments, the bacterium may be attenuated by regulating the murA nucleic acid sequence encoding the first enzyme in muramic acid synthesis and the asd nucleic acid sequence essential for DAP synthesis. These embodiments may comprise the chromosomal deletion-insertion mutations ΔasdA19::TT araC $P_{BAD}$ c2 or ΔasdA27::TT araC $P_{BAD}$ c2 and $\Delta P_{murA7}$::TT araC $P_{BAD}$ murA or $\Delta P_{murA12}$::TT araC $P_{BAD}$ murA or $\Delta P_{murA25}$::TT araC $P_{BAD}$ murA. This host-vector grows in LB broth with 0.1% L-arabinose, but is unable to grow in or on media devoid of arabinose since it undergoes cell wall-less death by lysis. In some embodiments of the invention, the recombinant bacterium may comprise araBAD and araE mutations to preclude breakdown and leakage of internalized arabinose such that asd and murA nucleic acid sequence expression continues for a cell division or two after oral immunization into an environment that is devoid of external arabinose. (For example a strain with the $\Delta P_{murA7}$:: TT araC $P_{BAD}$ murA deletion-insertion mutation undergoes about two cell divisions and then commences to lyse in media made of mouse or chicken feed or chicken breast meat, unless they are supplemented with arabinose). Either GTG or TTG start codons for the murA and asd nucleic acid sequences are important to decrease translation efficiency on multi-copy plasmids. The P22 $P_R$ promoter is in the anti-sense direction of both the asd nucleic acid sequence and the murA nucleic acid sequence. The P22 $P_R$ is repressed by the C2 repressor made during growth of the strain in media with arabinose (due to the $\Delta asdA19$::TT araC $P_{BAD}$ c2 deletion-insertion). However C2 concentration decreases due to cell division in vivo to cause $P_R$ directed synthesis of anti-sense mRNA to further block translation of asd and murA mRNA. The araC $P_{BAD}$ sequence is also not from *E. coli* B/r as originally described but represents a sequence derived from *E. coli* K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asd nucleic acid sequence does not replace the chromosomal asd mutation since they have a deleted sequence in common, consequently, the *E. coli* murA nucleic acid sequence was used in the plasmid instead of using the *Salmonella* murA nucleic acid sequence. The recombinant bacterium of this embodiment is avirulent at oral doses in excess of $10^9$ CFU to BALB/c mice. In addition to being fully attenuated, this construction exhibits complete biological containment with no in vivo recombinant bacteria survivors detectable after 21 days and no recombinant bacteria survivors during or after excretion. This property enhances vaccine safety and minimizes the potential for vaccination of individuals not intended for vaccination.

i. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I(c) above.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be necessary to synthesize a component of the cell wall of the bacterium, or may itself be a necessary component of the cell wall such as the protein encoded by murA. In still other embodiments, the protein may be listed in Section I(c) above.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

B. Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as $\Delta araBAD$ or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as $\Delta araBAD23$, which prevents use of arabinose retained in the cell cytoplasm at the time of oral immunization, and/or $\Delta araE25$ that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to rfaH nucleic acid sequences.

In some embodiments, more than one modification may be performed to optimize the attenuation of the bacterium. For instance, at least one, two, three, four, five, six, seven, eight or nine modifications may be performed to optimize the attenuation of the bacterium.

In various exemplary embodiments of the invention, the SD sequences and/or the start codons for the fur and/or the phoPQ virulence nucleic acid sequences may be altered so that the production levels of these nucleic acid products are optimal for regulated attenuation. For instance, a recombinant bacterium may comprise $\Delta P_{fur77}$::TT araC $P_{BAD}$ fur, whose start codon is changed from ATG to GTG, or $\Delta P_{fur81}$::TT araC $P_{BAD}$ fur, that has a weakened SD sequence as well as the start codon changed from ATG to GTG. Alternatively, a recombinant bacterium may comprise $\Delta P_{phopQ173}$::TT araC $P_{BAD}$ phoPQ, that has modifications to the start codon as well as the second codon, which was changed from ATG to GTG, or $\Delta P_{phopQ177}$::TT araC $P_{BAD}$ phoPQ, wherein the SD sequence has been changed to the weaker AAGG sequence, the start codon was modified, and the second codon was modified from ATG to GTG.

D. crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the rfaH nucleic acid sequence and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

E. Reduction in Fluid Secretion

In some embodiments, a recombinant bacterium of the invention may be modified so as to reduce fluid secretion in the host. For instance, the bacterium may comprise the $\Delta sopB1925$ mutation. Alternatively, the bacterium may comprise the $\Delta msbB48$ mutation.

F. Biological Containment

Under certain embodiments, a live recombinant bacterium may possess the potential to survive and multiply if excreted from a host. This leads to the possibility that individuals not electing to be immunized may be exposed to the recombinant bacterium. Consequently, in certain embodiments, a recombinant bacterium of the invention may comprise one or more mutations that decrease, if not preclude, the ability of *Salmonella* vaccines to persist in the GI tract of animals.

In another embodiment, a recombinant bacterium of the invention may comprise one or more of the $\Delta$(gmd fcl)-26 or $\Delta$(wza-wcaM)-8, $\Delta$agfBAC811 or $\Delta(P_{agfD}$ agfG)-4, $\Delta$bcs-ABZC2118 or $\Delta$bcsEFG2319 and $\Delta$(yshA-yihW)-157 mutations that block synthesis of colanic acid, thin aggregative fimbriae (i.e., curli), cellulose and extracellular polysaccharide, respectively, all of which contribute to biofilm formation. In addition, the mutation $\Delta$yhiR36 that prevents use of DNA as a nutrient, $\Delta$(shdA-ratB)-64, $\Delta$misL2 and $\Delta$bigA3 that encode four proteins that enable *Salmonella* to adhere to host extracellular matrix proteins and $\Delta$ackA233 that blocks use of acetate, may be used as a means for biological containment. In exemplary embodiments, a recombinant bacterium comprising a biological containment mutation are not adversely effected in their virulence.

In some embodiments, the recombinant bacterium may comprise a method of regulated delayed lysis in vivo that prevents bacterial persistence in vivo and survival if excreted. These chromosomal mutations may include: $\Delta$(gmd fcl)-26 or $\Delta$(wza-wcaM)-8 that precludes synthesis of colanic acid that can protect cells undergoing cell wall-less death from lysing completely, $\Delta$agfBAC811 that blocks synthesis of thin aggregative fimbriae (curli) that are critical for biofilm formation to enable persistent colonization on bile stones in the gall bladder, $\Delta$asdA27::TT araC $P_{BAD}$ c2 insertion-deletion mutation to impose a requirement for the peptidoglycan constituent DAP and $\Delta P_{murA12}$::TTaraC $P_{BAD}$ murA insertion-deletion mutation as a conditional-lethal mutation blocking synthesis of the peptidoglycan constituent muramic acid. The latter two mutations are typically complemented by a regulated delayed lysis plasmid vector such as pYA3681 that has an arabinose-dependent expression of asdA and murA genes. A recombinant bacterium comprising such mutations grows normally in the presence of arabinose. In vivo, however, the bacterium ceases to express any nucleic acids encoding the AsdA and MurA enzymes, such that synthesis of the peptidoglycan cell wall layer ceases, ultimately resulting in the lysis of the bacterium. This lysis may result in the release of a bolus of antigen specific for an exogenous pathogen, thereby serving as a means to enhance induction of immunity against that exogenous pathogen while conferring complete biological containment.

G. rfc Mutations

In addition to regulating LPS O-antigen synthesis with mannose, the synthesis of LPS O-antigen may be regulated by arabinose, which is also absent in vivo. For instance, a bacterium may comprise the mutation $\Delta P_{rfc}$::TT araC $P_{BAD}$ rfc. (P stands for promoter and TT stands for transcription terminator.) The rfc nucleic acid sequence is necessary for the addition of O-antigen subunits, which typically comprise three or four sugars, in a repeat fashion. When the rfc nucleic acid sequence is absent, only one O-antigen repeat subunit is added to the LPS core polysaccharide. Normally, the serotype-specific O-antigen contains some 50 or so repeats of the O-antigen subunit, catalyzed by the enzyme encoded by the rfc nucleic acid sequence. In the case of a bacterium comprising the $\Delta P_{rfc}$::TT araC $P_{BAD}$ rfc deletion-insertion mutation, expression of the rfc nucleic acid sequence is dependant on the presence of arabinose that can be supplied during in vitro growth of the strain, but that is absent in vivo. Consequently, rfc expression ceases in vivo, resulting in the cessation of assembly of the O-antigen repeat structure. This reduces the bacterium's ability to induce an immune response against the serotype-specific O-antigen. Suitable examples of rfc mutations may be found in the examples.

H. Other Mutations

In one embodiment, a recombinant bacterium of the invention may comprise a mutation in a nucleic acid that encodes FljB or FliC. For instance, a bacterium of the invention may comprise a ΔfljB217 mutation. Alternatively, a bacterium may comprise a ΔfliCI80 mutation. The ΔfljB217 mutation deletes the structural nucleic acid sequence that encodes the Phase II flagellar antigen whereas the ΔfliCI80 mutation deletes the 180 amino acids encoding the antigenically variable serotype-specific domain of the Phase I FliC flagellar antigen.

II. Vaccine Compositions and Administration

A recombinant bacterium of the invention may be particularly suited for use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesentery lymph nodes, liver and spleen may augment the induction of systemic and cellular immune responses directed against the bacterium. Thus the use of recombinant *Salmonella* for oral immunization stimulates all three branches of the immune system, which is particularly important for immunizing against infectious disease agents that colonize on and/or invade through mucosal surfaces.

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective. As used herein, "protective" means that the immune response contributes to the lessening of any symptoms associated with infection of a host with the pathogen the antigen was derived from or designed to elicit a response against. For example, a protective antigen from a pathogen, such as *Shigella*, may induce an immune response that helps to ameliorate symptoms associated with *Shigella* infection or reduce the morbidity and mortality associated with infection with the pathogen. The use of the term "protective" in this invention does not necessarily require that the host is completely protected from the effects of the pathogen.

Immune responses to antigens are well studied and widely reported. A survey of immunology is given by Paul, W E, Stites D et. al. and Ogra P L. et. al. Mucosal immunity is also described by Ogra P L et. al.

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. The vaccine can be administered as a prophylactic or for treatment purposes.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant. The vaccine compositions may further comprise additional components known in the art to improve the immune response to a vaccine, such as T-cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and non-parenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1\times10^7$ to about $1\times10^{10}$ CFU depending upon the age of the host to be immunized. In some embodiments, the initial oral dose may be about $1\times10^5$ to about $1\times10^{10}$ CFU. Generally speaking, intranasal doses are lower than the dose for oral immunization. For instance, in some embodiments, the intranasal dose may be between about 80 and about 120 times lower than the oral dose. Similarly, parenteral doses are lower than the dose for intranasal immunization. For example, the parenteral dose may be between about 5 and 15 times lower than the intranasal dose. Administering multiple dosages may also be used as needed to provide the desired level of protective immunity.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection, or other parenteral routes are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like In an exemplary embodiment, the recombinant bacterium may be administered orally. Oral administration of a composition comprising a recombinant bacterium allows for greater ease in disseminating vaccine compositions for infectious agents to a large number of people in need thereof, for example, in Third World countries or during times of biological warfare. In addition, oral administration allows for attachment of the bacterium to, and invasion of, the gut-associated lymphoid tissues (GALT or Peyer's patches) and/or effective colonization of the mesentery lymph nodes, liver, and spleen. This route of administration thus enhances the induction of mucosal immune responses as well as systemic and cellular immune responses.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians, veterinarians, and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against an antigen in a host. The method comprises administering to the host an effective amount of a composition comprising a recombinant bacterium of the invention.

In still another embodiment, a recombinant bacterium of the invention may be used in a method for eliciting an immune response against an exogenous pathogen in an individual in need thereof. Generally speaking, a recombinant bacterium of the invention is also capable of eliciting an immune response against at least one exogenous pathogen in addition to *Salmonella*. This may be accomplished, for instance, by regulating the expression of an exogenous antigen as described above. In an alternative embodiment, the exogenous antigen may be an iron-regulated outer membrane protein (IROMP) or a manganese-regulated outer membrane protein (MnROMP). For instance, the mutation $\Delta P_{fur}$::TT araC $P_{BAD}$ fur in a *Salmonella* recombinant bacterium may cause up-regulation of IROMPS while the bacterium is growing in the host. This up-regulation may elicit a host immune response against the IROMPS of the *Salmonella* recombinant bacterium that cross-reacts with similar proteins from *Shigella, E. coli*, and *Yersinia*.

An "exogenous pathogen," as used herein, refers to a pathogen capable of invading and colonizing the intestines of a host and causing pathology. The pathology, however, is not limited to the gastrointestinal tract. Many exogenous pathogens cause extra intestinal diseases such as typhoid fever, meningitis, septicemia, and urinary tract infections, and use the intestines as a route of entry or as a reservoir from which to spread to other sites of entry. Additionally, some exogenous bacteria can invade and colonize via the respiratory tract. This is most common in birds, such as chickens and turkeys that scratch to aerosolize exogenous bacteria that can invade the lungs and airsacs during breathing. These same exogenous bacteria are also ingested by birds such that they are equally capable of residing in the intestinal tract. In either case, these exogenous bacteria are still able to colonize internal tissues to cause disease independent of whether the invasion occurred via the gastrointestinal or respiratory tracks. Non-limiting examples of exogenous pathogens may include *E. coli* serotypes O124, O86:B7, H37, O27, O124:B17, O6:H16, O25:H+, O27:H2O, O157:H7; *Shigella* Serogroup A or *S. dysenteriae* (12 serotypes), Serogroup B or *S. flexneri* (6 serotypes), Serogroup C or *S. boydii* (23 serotypes), Serogroup D or *S. sonnei* (1 serotype); *Clostridium perfringens; Yersinia enterocolitica; Yersina pseudotuberculosis*; and *Campylobacter jejuni*.

The elicited immune response may include, but is not limited to, an innate immune response, a humoral immune response and a cell-mediated immune response. In one embodiment, Th2-dependent mucosal and systemic antibody responses to the exogenous antigen(s) are observed. Immune responses may be measured by standard immunological assays known to one of skill in the art. In an exemplary embodiment, the immune response is protective.

In some embodiments, a recombinant bacterium of the invention may be used in a method for eliciting an immune response against at least 1, 2, 3, 4, 5 or more than 5 exogenous pathogens in an individual in need thereof. The method comprises administrating to the host an effective amount of a composition comprising a recombinant bacterium as described herein. In a further embodiment, a recombinant bacterium described herein may be used in a method for ameliorating one or more symptoms of an exogenous disease in a host in need thereof. The method comprises administering an effective amount of a composition comprising a recombinant bacterium as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1 rfaH Mutations

When recombinant attenuated *Salmonella* vaccines (RASV) are used to deliver heterologous antigens, it may be advantageous to reduce the host immune response against the RASV carrier, thereby enhancing the immune response against the heterologous antigen. The dominant immunogen on the *Salmonella* cell surface is lipopolysaccharide (LPS) O-antigen (58). However, strains with mutations that eliminate LPS O-antigen may be less immunogenic due to failure of these kinds of mutants to colonize the intestinal tract and invade intestinal mucosal cells (60, 61). We hypothesize that in vivo programmed down-regulation of O-antigen expression, occurring after colonization of host lymphoid tissues, will serve to reduce the immune response against the RASV carrier, while triggering a strong immune response against heterologous antigens (12) and outer membrane proteins cross-reactive with other enteric bacteria (40). The genes for LPS core and O-antigen biosynthesis are clustered into long operons (53, 68) that cannot be fully transcribed if the native promoter is replaced by a heterologous promoter. RfaH, a transcriptional anti-terminator, reduces the polarity of long operons by binding to the ops sequence, encoded in an untranslated 5' region of the transcript, and interacting with the transcription complex (1). RfaH is required for expression of secreted and surface-associated cell components of *Salmonella enterica* serovar *Typhimurium*, including O-antigen and core sugar components of LPS (3, 55). rfaH mutant strains produce truncated LPS and reduced amounts of O-antigen and core (31) rendering them sensitive to human serum (26), hypersensitive to bile and attenuated in mice (38, 62). ΔrfaH mutants are immunogenic in mice, inducing a protective immune response against *Salmonella* challenge (39). The major immunogenic surface molecules of *S. enterica* are the O-antigen and flagella. Complete LPS is of considerable importance, as rough mutants of *Salmonella* lacking LPS O-antigen side chains or portions of the core are avirulent, fail to colonize the intestinal tract and are deficient in invading cells of the intestinal mucosa (60). To circumvent this problem, we and others have explored different ways to achieve regulated O-antigen synthesis, such that O-antigen is synthesized in vitro, but not in vivo, creating vaccine strains that are phenotypically wild-type at the time of immunization and become attenuated after colonization of host tissues. We have termed this strategy regulated delayed attenuation (13, 14, 29). One means to achieve regulated delayed attenuation is the deletion of certain genes essential for O-antigen synthesis such as pmi (manA) (11, 14, 29) or galE (18, 24, 59). Strains with Δpmi or ΔgalE deletions have a reversibly rough phenotype because they are only able to synthesize complete O-antigen or O-antigen combined to entire core when grown in the presence of mannose or galactose, respectively. When grown in the presence of their respective sugar, these mutants are fully fit to carry out host colonization and invasion of host tissues during the early stages of infection (14, 22). Upon reaching deeper tissues where free mannose and galactose are not available, O-antigen is no longer synthesized and the strains become phenotypically rough.

Another strategy for achieving regulated delayed attenuation relies on substitution of the promoter of a gene of interest with the arabinose-regulated araC $P_{BAD}$ promoter (13, 14). The araC $P_{BAD}$ promoter has been used to develop regulated delayed attenuation strains in which the expression of a number of *Salmonella* virulence genes such as fur, crp, and rpoS are dependent upon arabinose availability (13). In this work, the rfaH promoter, including sequences for activator or repressor protein binding, was deleted and replaced with an araC $P_{BAD}$ cassette to yield *Salmonella* strains in which rfaH transcription was arabinose-dependent. By manipulation of translation signals, we constructed a series of strains, each synthesizing different amounts of RfaH. Growth of these strains in the presence of arabinose permitted transcription of rfaH and synthesis of full length O-antigen. We evaluated these strains for virulence, immunogenicity and the ability to deliver a test antigen, the pneumococcal protein PspA. Immunized mice were challenged with virulent *Streptococcus pneumoniae* to determine protective efficacy.

Materials and Methods

Bacterial Strains, Plasmids, Media, and Growth Conditions.

The bacterial strains and plasmids used in this study are listed in Table 1. *S. Typhimurium* cultures were grown at 37° C. in LB broth (4), nutrient broth (Difco) or on LB agar with or without 0.1% arabinose. Selenite broth, with or without supplements, was used for enrichment of *Salmonella* from mouse tissues. Diaminopimelic acid (DAP) was added (50 µg/ml) for the growth of Δasd strains (43). LB agar containing 5% sucrose was used for sacB gene-based counterselection in allelic exchange experiments. *S. pneumoniae* WU2 was cultured on brain heart infusion agar containing 5% sheep blood or in Todd-Hewitt broth plus 0.5% yeast extract. MOPS minimal medium (45) with/without 10 µg/ml p-aminobenzoic acid (pABA) was used to confirm the phenotype of ΔpabA ΔpabB mutants.

Plasmids and Mutant Strain Construction.

DNA manipulations were carried out as described (52). Transformation of *E. coli* and *S. enterica* was done by electroporation. Transformants were selected on LB agar plates containing appropriate antibiotics. Selection for Asd+ plasmids was done on LB agar plates. The primers used in this work are listed in Table 2. A 500-bp DNA fragment containing the region upstream of the rfaH promoter was PCR amplified using the *S. Typhimurium* χ3761 genome as template with primers RfaH1-FXmal-pstI and RfaH1-RPstI (Table 2). The PCR-amplified fragment was digested with PstI and cloned into the PstI site of vector pYA3700 (Table 1), which lies just upstream of araC. Primer T4TT-R, that binds to the T4 transcriptional terminator antisense sequence present downstream of the PstI site in pYA3700 and primer RfaH1-RPstI were used to screen plasmid isolates for inserts in the correct orientation. This intermediate plasmid was digested with XhoI and KpnI, restriction sites that lie downstream of the araC $P_{BAD}$ cassette. Three different 0.5 kb PCR fragments encoding the entire 489 bp rfaH gene and an additional 21 bp downstream, were amplified from the *S. Typhimurium* χ3761 genome, using three different upstream primers, RfaH2-FXhoI, RfaH2-1, and RfaH2-2, and the same downstream primer RfaH2-Rkpnl. Each PCR fragment was engineered to encode a different Shine-Dalgarno (SD) sequence and/or start codon (Table 1) due to differences in the upstream primers. The PCR fragments were digested with XhoI and KpnI and inserted into the intermediate plasmid described above. The three resulting constructs were confirmed by DNA sequence analysis. Then, 2.5-kb DNA fragments encoding araC $P_{BAD}$ rfaH and rfaH 5' and 3' flanking regions were excised from each of the plasmids by digestion with KpnI and XmaI and inserted into pRE112, resulting in plasmids pYA4721, pYA4301, and pYA4304. To construct the ΔrfaH49 deletion, two pairs of primers RfaH-1F/RfaH-1R and RfaH-2F/RfaH-2R were used to amplify approximately 300-bp fragments upstream and downstream of rfaH, respectively, from the χ3761 genome. The two PCR fragments were purified in agarose gels and used as template at a 1:1 molar ratio for joining by PCR using primers RfaH-1F and RfaH-2R. The resulting PCR product was digested with KpnI and XmaI and ligated with plasmid pRE112, digested with the same two enzymes, resulting in plasmid pYA4718, which carries a deletion of the entire rfaH gene from ATG to TAA. The mutations were introduced into S. Typhimurium χ3761 by allelic exchange using the four suicide vectors pYA4718, pYA4721, pYA4301, and pYA4304 to generate χ9945, χ9660, χ9734, χ9735, respectively. The ΔrfaH49 and $P_{rfaH178}$ mutations were also introduced into S. Typhimurium strain χ9241 to yield strain χ9884 and χ9852, respectively. The presence of both pabA1516 and pabB232 mutations in Salmonella strain χ9241, χ9884 and χ9852 were verified by the inability of the strains to grow in MOPS minimal medium without p-aminobenzoate. The presence of ΔasdA16 mutation was confirmed by inability to grow in media without DAP and by PCR. The ΔaraBAD23 mutation was verified by PCR and by its white colony phenotype on MacConkey agar supplemented with 1% arabinose. LPS profiles of Salmonella strains were examined by the methods of Hitchcock and Brown (20) using cultures standardized based on $OD_{600}$.

P22 Transduction Studies.

P22HT int (56) was propagated on S. Typhimurium strain χ9430 carrying the integrated suicide plasmid pYA4284, which confers chloramphenicol resistance. Strains to be tested were grown overnight in nutrient broth at 37° C. Cultures were diluted 1:100 into fresh, prewarmed nutrient broth with or without 0.1% arabinose and grown at 37° C. to an $OD_{600}$ of 0.9. Then, 10 μl of phage ($1 \times 10^8$ PFU) was added to 1 ml of cells ($5 \times 10^8$ CFU) and the mixture was incubated at room temperature for 30 min, centrifuged and resuspended in 200 μl of buffered saline with gelatin (BSG). A 100 μl aliquot was spread onto LB agar plates containing 15 μg/ml chloramphenicol and incubated overnight at 37° C. Colonies were counted the following day. This experiment was performed twice.

Minimum Inhibitory Concentration (MIC) Test.

The MICs of different antimicrobial substances were determined by using 96-well tissue culture plates (69). Two-fold serial dilutions of the bile salt, deoxycholate (0.1 to 50 mg/ml), and polymyxin B (0.1 to 10 μg/ml) were made across the plates. Bacteria were grown at OD600=0.8-0.9 in nutrient broth with or without 0.1% arabinose and washed in PBS. Cells were diluted to $1 \times 10^5$ to $1 \times 10^6$ CFU in nutrient broth with or without arabinose. 0.1 ml of the diluted cell suspension was added to each well. The microtiter plates were incubated overnight at 37° C. The optical density of each culture was determined using a model SpectraMax M2e (Molecular Devices, CA) plate reader. The threshold of inhibition was 0.1 at $OD_{600}$. Actual titers were determined by spreading culture dilutions onto LB plates followed by overnight incubation at 37° C. Assays were repeated at least three times.

Actual titers were determined by spreading culture dilutions onto LB plates followed by overnight incubation at 37° C. Assays were repeated at least three times.

Swimming.

Swimming motility was assessed on LB plates solidified with 0.3% agar and supplemented with 0.5% glucose with or without 0.1% arabinose. The plates were allowed to dry at room temperature for 2 h. Freshly grown bacteria were collected from LB agar plates without arabinose, washed and diluted in saline. Six microliters of bacterial suspension (approximately $1 \times 10^6$ CFU) was spotted onto the middle of the plates, which were subsequently incubated at 37° C. for 6 h. The diameter of the swimming colonies were measured. Experiments were repeated three times.

Determination of Virulence in Mice.

Seven week old, female BALB/c mice were obtained from the Charles River Laboratories. All animal procedures were approved by the Arizona State University Animal Care and Use Committees. Mice were acclimated for 7 days after arrival before starting the experiments.

For determination of the 50% lethal dose ($LD_{50}$), bacteria were grown statically overnight at 37° C. in LB broth, diluted 1:50 into fresh media containing 0.1% arabinose, and grown with aeration (180 rpm) at 37° C. When the cultures reached an OD600=0.8-0.9, they were harvested by room temperature centrifugation at 4,000 rpm, washed once, and normalized to the required inoculum density in BSG by adjusting the suspension to the appropriate $OD_{600}$ value. Groups of five mice each were infected orally with 20 μl containing various doses of S. Typhimurium χ3761 or its derivatives, ranging from $1 \times 10^3$ CFU to $1 \times 10^8$ CFU. Animals were observed for 4 weeks post infection, and deaths were recorded daily.

To evaluate colonization, mice were orally inoculated with 20 μl of BSG containing $1 \times 10^9$ CFU of each strain. At days 4 and 8 after inoculation, three animals per group were euthanized and spleen and liver samples were collected. Each sample was homogenized in a total volume of 1 ml BSG, and dilutions of $10^{-1}$ to $10^{-6}$ (depending on the tissue) were plated onto MacConkey agar and LB agar, each containing 0.1% arabinose, to determine the number of viable bacteria. A 0.1 ml aliquot of each tissue sample was inoculated into selenite cysteine broth. Samples that were positive by enrichment in selenite cysteine broth for 14 h at 37° C. were recorded as <10 CFU/g.

Immunogenicity of Vaccine Strains in Mice.

RASV strains were grown statically overnight in LB broth with 0.1% arabinose at 37° C. The following day, 2 ml of the overnight culture was inoculated into 100 ml of LB broth with 0.1% arabinose and grown with aeration at 37° C. to an $OD_{600}$ of 0.8 to 0.9. Cells were harvested by room temperature centrifugation at 4,000 rpm for 15 min and the pellet resuspended in 1 ml of BSG. Mice were orally inoculated with 20 μl of BSG containing $1 \times 10^9$ CFU of each strain on day 0 and boosted on day 28 with the same dose of the same strain. Blood was obtained by mandibular vein puncture at biweekly intervals. Blood was allowed to coagulate at 37° C. for two hours. Following centrifugation, the serum was removed from the whole blood and stored at −20° C.

Antigen Preparation.

rPspA protein was purified as described (25). The rPspA clone which encodes the α-helical region of PspA (aa 1-302) in pET20b, was kind gift from Dr. Susan Hollingshead at the University of Alabama at Birmingham. S. Typhimurium LPS was purchased from Sigma. Outer membrane proteins were prepared as described (25). To prepare whole cell antigens, various enteric bacteria were grown statically overnight at 37° C. in LB broth, diluted 1:50 into fresh media, and grown with aeration (180 rpm) at 37° C. to an $OD_{600}$=0.8-0.9. Cells were harvested by centrifugation at 4,000 rpm, washed once in PBS, and suspending in coating buffer (50 mM $Na_2CO_3$, 50 mM $NaHCO_3$, 0.1% sodium azide, pH 9.6) to an $OD_{600}$=0.8. Then, 100 μl/well of the resulting cell suspension was used to coat the ELISA plate overnight at 4° C.

SDS-PAGE and Western Blot Analyses.

Protein samples were boiled for 5 min and then separated by SDS-PAGE. For western blotting, proteins separated by SDS-PAGE were transferred electrophoretically to nitrocellulose membranes. The membranes were blocked with 3% skim milk in 10 mM Tris-0.9% NaCl (pH 7.4) and incubated with rabbit polyclonal antibodies specific for PspA (51) or GroEL (Sigma, St. Louis, Mo.). The secondary antibody was an AP-conjugated goat anti-rabbit immunoglobulin G (IgG) (Sigma). Immunoreactive bands were detected by the addition of BCIP/NBT solution (Sigma). The reaction was stopped after 2 min by washing with large volumes of deionized water.

Enzyme-Linked Immunosorbent Assay (ELISA).

ELISA was used to assay serum antibodies against *S. Typhimurium* LPS, rPspA, bacterial outer membrane proteins, including those from *Salmonella* (SOMPs) and whole cell bacterial suspensions ($1 \times 10^9$ CFU/ml) as previously described (30). Color development (absorbance) was recorded at 405 nm using a SpectraMax M2e automated ELISA plate reader (Molecular Devices, Menlo Park, Calif.). Absorbance readings 0.1 higher than PBS control values were considered positive.

Pneumococcal Challenge.

We assessed the protective efficacy of immunization with the attenuated *Salmonella* expressing pspA at week 8 by intraperitoneal (i.p.) challenge with $4 \times 10^4$ CFU of *S. pneumoniae* WU2 in 200 µl of BSG (44) The LD50 of *S. pneumoniae* WU2 in BALB/c mice was $2 \times 10^2$ CFU by i.p. administration (data not shown). Challenged mice were monitored daily for 30 days.

Statistical Analysis.

Antibody titer data were expressed as geometric means and the relative immunoreactivity was expressed as an arithmetic mean. The means were evaluated with two-way ANOVA and Chi square test for multiple comparisons among groups. $P<0.05$ was considered statistically significant.

Results

Mutant Construction and LPS Phenotypes.

Figure 1C:
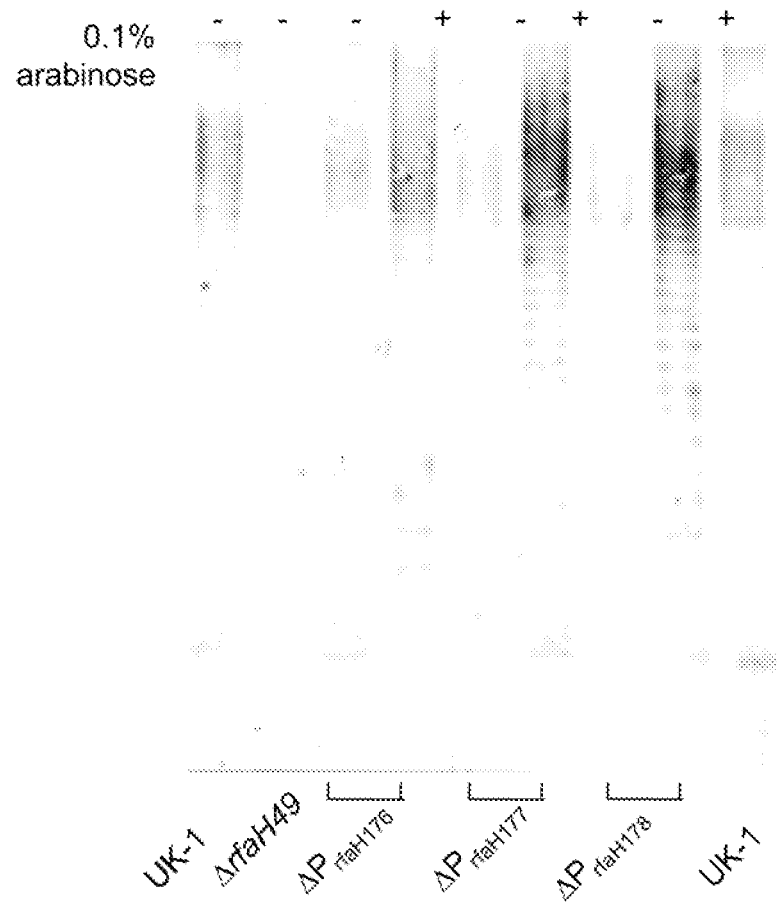

We constructed *S. Typhimurium* χ3761 derivatives with rfaH transcribed from the arabinose-regulated araC $P_{BAD}$ promoter, each designed to synthesize different amounts of RfaH. FIG. 1A illustrates the chromosomal structure of the araC $P_{BAD}$ rfaH mutant strains. Ninety-eight base pairs upstream of the start codon were replaced with araC $P_{BAD}$ to create the $\Delta P_{rfaH177}$ mutation. A different Shine-Dalgarno (SD) sequence or a GTG start codon was introduced to create $\Delta P_{rfaH176}$ and $\Delta P_{rfaH178}$, respectively. The SD and start codon sequence for each mutant strain is given in Table 1. The levels of O-antigen synthesis in the mutants were determined by silver staining (FIG. 1B) and by western blotting using anti-Salmonella group B O-antigen serum (FIG. 1C). Lack of rfaH expression, either by deletion (ΔrfaH49) or growth of $P_{BAD}$ rfaH strains in the absence of arabinose, resulted in a reduced O-antigen synthesis in all four mutant strains. In the three araC $P_{BAD}$ rfaH mutants, nearly wild-type O antigen levels were restored by the addition of arabinose to the growth medium. None of the three arabinose-regulated rfaH mutants were completely rough when grown in the absence of arabinose, although the $\Delta P_{rfaH178}$ strain produced the least amount of high molecular weight O-antigen (FIG. 1B, 1C). The $\Delta P_{rfaH176}$ mutant with a canonical SD sequence and ATG start codon would be expected to synthesize the most RfaH and the $\Delta P_{rfaH178}$ mutant, with a non-ideal SD sequence and a GTG start codon would be expected to synthesize the least amount of RfaH among the three strains. Although we did not directly measure the amount of RfaH synthesized by each strain, the differing amounts of O-antigen produced by each are consistent with our expectations, with the $\Delta P_{rfaH176}$ mutant producing the most O-antigen and the $P_{rfaH178}$ mutant producing the least amount, in the absence of arabinose. The ΔrfaH49 mutant did not produce any detectable high molecular weight O-antigen with or without arabinose (FIG. 1B, 1C).

To further evaluate arabinose-regulated O-antigen synthesis, we performed infection studies with the O-antigen-specific phage P22. Strains were grown in nutrient broth with or without arabinose and used as recipients for transduction assays. When strains χ9660 ($\Delta P_{rfaH176}$), χ9734 ($\Delta P_{rfaH177}$) and χ9735 ($\Delta P_{rfaH178}$) were grown with arabinose, the number of transductants obtained was similar to the wild-type parent strain χ3761 (Table 3). In the absence of the arabinose, the number of transductants was reduced about 10-fold, which was still about 3-4-fold more than that obtained with the ΔrfaH49 strain, χ9445. These results are consistent with our observations that in the absence of arabinose, the strains with arabinose-regulated rfaH make less full-length O-antigen than χ3761 and more than χ9445 (FIG. 1).

Phenotypic Evaluation of rfaH Mutant Strains.

A previous report indicated that an rfaH deletion resulted in increased sensitivity to antimicrobial peptides (38). Therefore, we evaluated our mutant strains for sensitivity to the bile salt, deoxycholate and to the antimicrobial peptide polymyxin B. The deoxycholate and polymyxin B MICs for the wild-type strain χ3761 were >5-fold higher than for the ΔrfaH49 mutant χ9945 (Table 3). These results are in agreement with previous reports that a *Salmonella* SL1344 ΔrfaH292 mutant strain is more sensitive to polymyxin B than wild type (38). Strain χ9960, the arabinose-regulated $P_{rfaH176}$, had MICs for both test substances similar to the wild-type, exhibiting only a 2-fold reduction in MIC in the absence of arabinose, consistent with the leaky phenotype observed for O-antigen synthesis (FIG. 1). The other two arabinose regulated rfaH strains, χ9734 and χ9735 had nearly wild-type MICs for DOC and polymyxin B in the presence of arabinose. The MICs in the absence of arabinose were identical to the ΔrfaH49 strain χ9945.

Rough mutants are unable to swarm, because of insufficient surface wetness (64). Therefore, we evaluated the capacity of our mutant strains to exhibit swarming motility on soft agar (Table 3). Strain χ9945 (ΔrfaH49) did not swarm, as expected. Swarming was dramatically reduced (>2-fold reduction in diameter) in the absence of arabinose for the arabinose-regulated rfaH strain χ9735 ($\Delta P_{rfaH178}$). The remaining two strains, χ9660 ($\Delta P_{rfaH176}$) and χ9734 ($\Delta P_{rfaH177}$), showed slight reductions in swarming (<2-fold reduction in diameter) in the absence of arabinose. Swarming was restored to wild-type levels in the presence of arabinose in all three arabinose-regulated rfaH strains.

Virulence of $\Delta P_{rfaH}$ and ΔrfaH49 Mutant Strains in Mice.

To assess the virulence of the rfaH mutants, we determined their $LD_{50}$s in BALB/c mice (Table 3). The ΔrfaH49 mutant was highly attenuated, with no death occurring at the maximum dose tested, $1 \times 10^8$ CFU, in agreement with previous results (39). The parent strain χ3761 was highly virulent with an $LD_{50}$ of $1 \times 10^4$ CFU. The arabinose-regulated mutant strains χ9734 and χ9735 were both attenuated with $LD_{50}$s of $1 \times 10^6$ CFU despite the fact that they were grown in the presence of arabinose prior to inoculation. Strain χ9660, the $\Delta P_{rfaH176}$ mutant, was not tested since our earlier phenotypic analyses indicated that rfaH expression was not tightly regulated (FIG. 1, Table 3).

Expression of the Pneumococcal Gene pspA in RASV Strain χ9241 Derivatives Carrying Different rfaH Mutations.

*S. Typhimurium* strain χ9241 is an attenuated vaccine strain that has been successfully used to deliver the pneumococcal surface protein PspA and induce protective immunity against *S. pneumoniae* challenge (30, 71). To evaluate the effect of rfaH mutations on the efficacy of this vaccine strain, the ΔrfaH49 and ΔP$_{rfaH178}$ mutations were introduced into χ9241 to yield strains χ9884 and χ9852, respectively. Subsequently, the Asd$^+$ recombinant plasmid pYA4088, which encodes a recombinant pspA gene fused to DNA encoding the β-lactamase signal sequence (71), was introduced into the new strains. Expression of pspA is driven by the P$_{trc}$ promoter and the bla signal sequence directs periplasmic secretion of PspA. Note that strain χ9241 carries the ΔrelA198::araC P$_{BAD}$ lacI TT deletion/insertion mutation. When this strain is grown in the presence of arabinose, lacI is expressed. The LacI protein binds to the P$_{trc}$ promoter on pYA4088, preventing pspA expression. Once the strain invades and colonizes host tissues, where arabinose is not available, LacI is no longer synthesized and pspA is expressed. This feature has been termed regulated delayed in vivo antigen synthesis (71).

Figure 2:
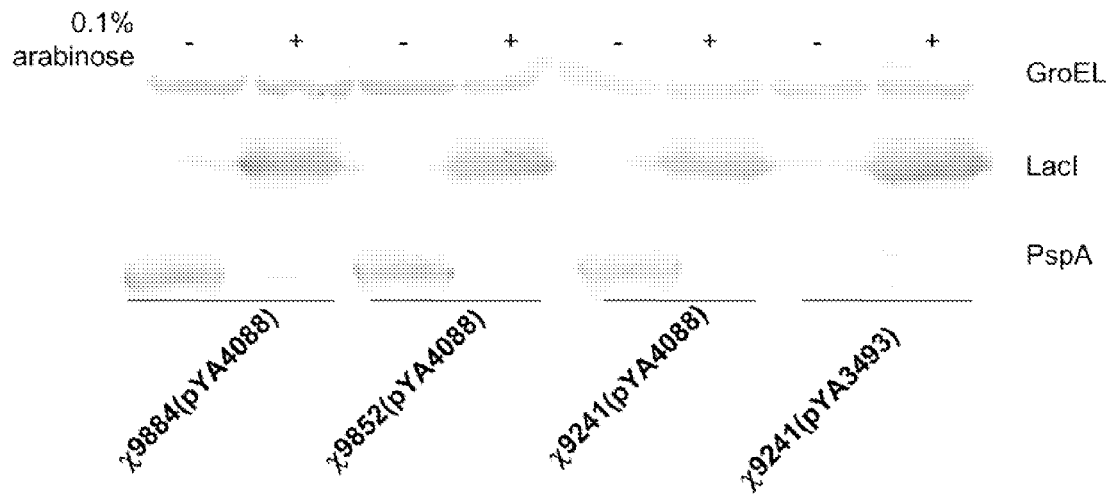
FIG. 2. PspA and LacI synthesis are regulated by 0.1% arabinose. Western blotting showing the synthesis of PspA in *S. Typhimurium* strains χ9884(pYA4088) (ΔrfaH49), χ9852 (pYA4088) ($\Delta P_{rfaH178}$), χ9421(pYA4088) (RfaH+) and χ9241(pYA3493). Bacteria were grown in LB broth with or without 0.1% arabinose overnight at 37° C. Equal numbers of cells from each culture were pelleted, suspended in loading buffer, and boiled. After centrifugation, equal volumes were subjected to SDS-PAGE, transferred to nitrocellulose and probed with a polyclonal antibody specific for PspA, LacI, or GroEL, respectively. GroEL was used as a standardization marker.

All strains expressed a protein with an approximate molecular mass of 38.5 kDa, the expected size of the LacI protein that reacted specifically with an anti-LacI polyclonal antibody (FIG. 2). No LacI was detected when the strains were grown in LB media without 0.1% arabinose. Conversely, in LB media with 0.1% arabinose where all strains expressed LacI, no PspA protein was detected. Strains carrying pYA4088 grown in the absence of arabinose produced PspA, but not LacI. There was no obvious difference in the amount of PspA synthesized for any of the strains carrying pYA4088.

Colonization of Mouse Tissues and Immune Responses in Mice after Oral Immunization with RASV Expressing PspA.

Figure 3A:
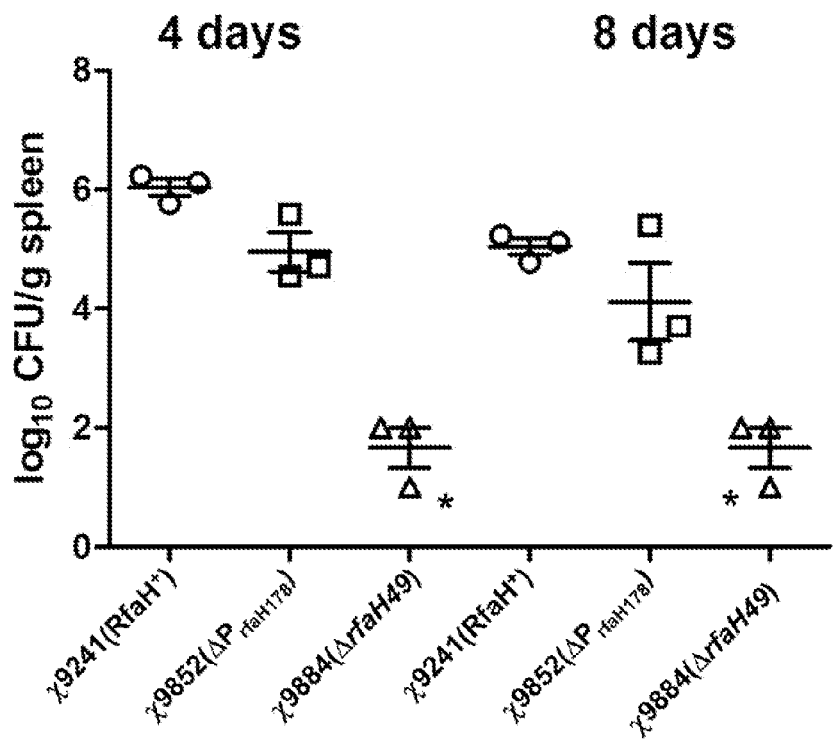
FIG. 3. Colonization of mouse spleen and liver by attenuated *S. Typhimurium* grown in LB broth containing 0.1% arabinose. (A) Spleen and (B) liver colonization by the indicated strains in BALB/c mice on 4 days and 8 days post inoculation. * no bacteria were detected by direct plating, but were positive by selenite cysteine broth enrichment. These samples were scored as <10 CFU.
Figure 3B:
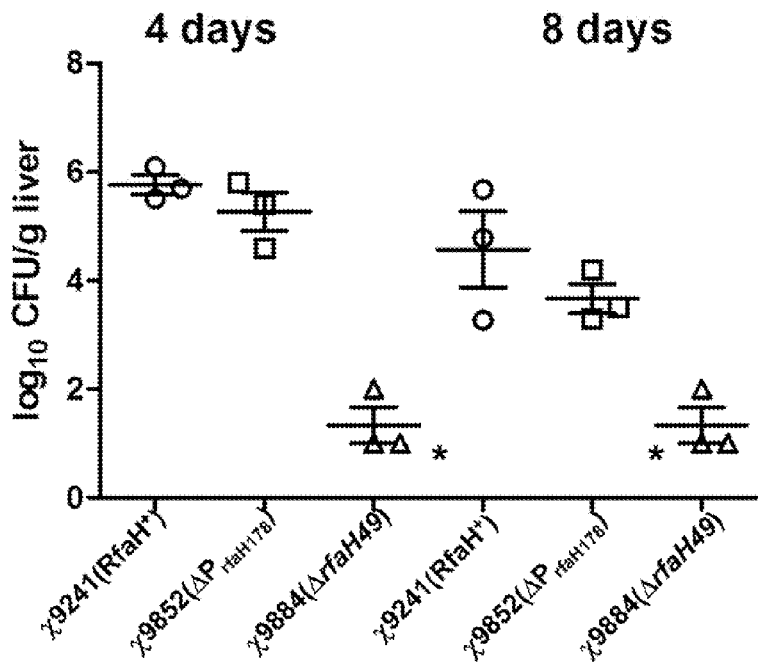

To evaluate the effect of arabinose regulated rfaH expression on colonization of mouse tissues, strains χ9241 (pYA4088), χ9884(pYA4088) and χ9852(pYA4088) were grown in the presence of arabinose and used to inoculate groups of BALB/c mice. On days 4 and 8, three mice from each group were euthanized and spleen and liver samples were harvested, homogenized and plated onto MacConkey and LB plates, each containing 0.1% arabinose. We found significant differences between the strains in their abilities to colonize liver and spleen (FIG. 3). Strain χ9852(pYA4088) (ΔP$_{rfaH178}$) and its parent strain χ9241 (pYA4088) colonized spleen and liver to significantly higher numbers than χ9884 (pYA4088) (ΔrfaH49) (P<0.0001). There was a slight reduction in tissue colonization by χ9852(pYA4088) compared to its parent strain χ9241(pYA4088), but the difference was not statistically significant (P>0.05).

Effect of rfaH Mutations on Immunogenicity and Protective Efficacy of RASV Strains.

Figure 4A:
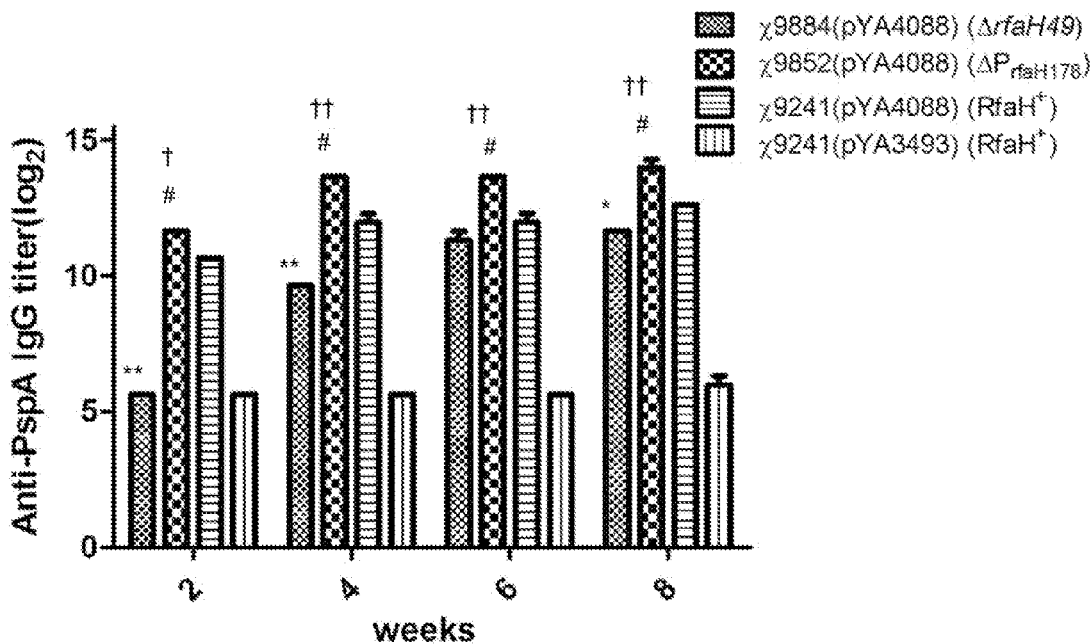
FIG. 4. Serum IgG responses in immunized and control mice. Total serum IgG specific for rPspA (A), *S. Typhimurium* LPS (B) and SOMP (C) were measured by ELISA. The data represent reciprocal anti-IgG antibody levels in pooled sera from mice orally immunized with attenuated *Salmonella* carrying either pYA4088 (pspA) or pYA3493 (control) at the indicated weeks after immunization. Error bars represent variation between triplicate wells. Mice were boosted at week 4. **: χ9884(pYA4088) vs. χ9241(pYA4088), P<0.001, *: χ9884(pYA4088) vs. χ9241(pYA4088), P<0.01; #: χ9884 (pYA4088) vs. χ9852(pYA4088), P<0.001; ††: χ9852 (pYA4088) vs. χ9241(pYA4088), P<0.001, †: χ9852 (pYA4088) vs. χ9241(pYA4088), P<0.01. For panel (C) χ9884(pYA4088) was different from all other groups (P<0.001). There was no statistical difference between the other strains shown in panel (C).
Figure 4:
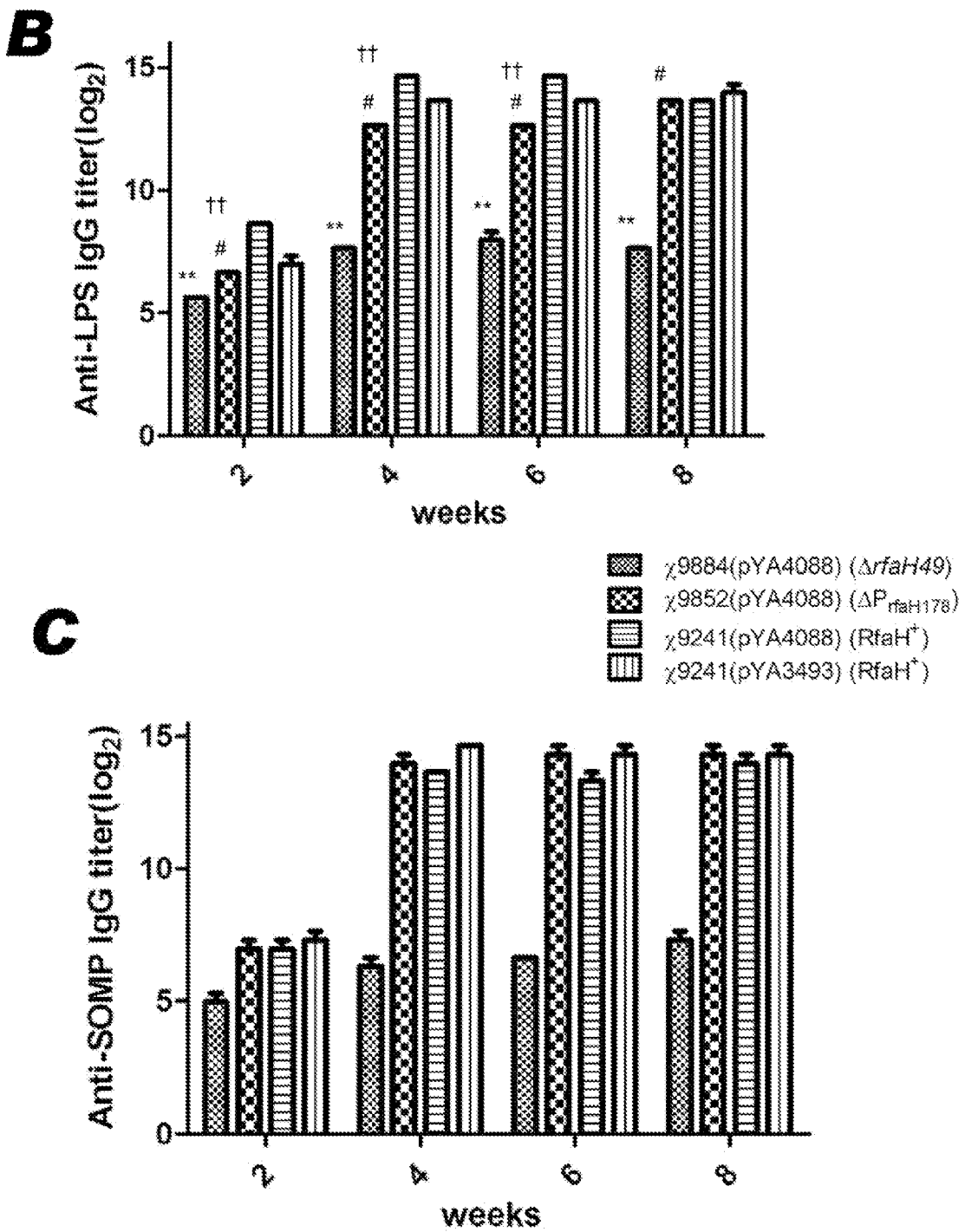

We orally inoculated groups of mice with 1–2×10$^9$ CFU of either χ9241(pYA4088), χ9884(pYA4088) (ΔrfaH49), χ9852(pYA4088) (ΔP$_{rfaH178}$), or control strain χ9241 (pYA3493) that does not express pspA. Mice were boosted with a similar dose of the same strain 4 weeks later. The antibody responses to rPspA and *Salmonella* LPS in the sera of immunized mice were measured (FIG. 4). This experiment was performed twice, 5 mice per group were used in the first experiment, and 8-11 mice per group were used in the second experiment. The results from both experiments were similar and have been pooled for analysis. High serum IgG titers against PspA were observed by 2 weeks after the primary immunization in mice inoculated with χ9241(pYA4088) and χ9852(pYA4088) (FIG. 4A). Anti-PspA titers in mice immunized with χ9884(pYA4088) (ΔrfaH) were slower to develop and by 6 weeks had reached levels comparable to mice immunized with χ9241(pYA4088). However, mice immunized with χ9852(pYA4088) (ΔP$_{rfaH178}$) achieved significantly higher titers than the other two groups. No anti-PspA IgG was detected in sera from mice inoculated with the control strain χ9241(pYA3493).

Anti-LPS titers were low, but detectable at 2 weeks (FIG. 4B). Titers remained low in mice immunized with the ΔrfaH strain χ9884(pYA4088) throughout the course of the experiment, while anti-LPS serum titers increased in mice immunized with the other strains. Before week 8, the anti-LPS titers were significantly lower in mice immunized with the ΔP$_{rfaH178}$ strain χ9852(pYA4088) than in either group immunized with a χ9241 derivative (P<0.001) and they were significantly higher than those of mice immunized with the ΔrfaH strain (P<0.001). By week 8, mice immunized with either of the χ9241 derivatives or with χ9852(pYA4088) had similar anti-LPS IgG titers. Anti-SOMP titers were similar for all strains except χ9884(pYA4088), which was statistically different (P<0.001).

IgG Isotype Analyses.

We evaluated the IgG isotype subclasses IgG1 and IgG2a (FIG. 5) responses to rPspA. Th1-helper cells direct cell-mediated immunity and promoter class switching to IgG2a, and Th2 cells provide potent help for B cell antibody production and promote class switching to IgG1. Immunization with strain χ9884(pYA4088) induced a strong Th2-response, since the levels of ant-PspA IgG1 were higher than IgG2a. Conversely, immunization with strains χ9852(pYA4088) (ΔP$_{rfaH178}$) and χ9241(pYA4088) (RfaH$^+$) induced primarily a Th1-type response against PspA.

Evaluation of Protective Immunity.

To evaluate the effect the ΔrfaH49 and ΔP$_{rfaH178}$ mutations on the ability of the RASV expressing PspA to induce protective immunity, mice were challenged by the intraperitoneal route with 4×10$_4$ CFU (200 LD$_{50}$s) of *S. pneumoniae* WU2 4 weeks after the boost. Immunization with any of the pspA-expressing strains provided significant protection against challenge compared to control strain χ9241 (pYA3493) (FIG. 6; P<0.001). Immunization with χ9852 (pYA4088) (ΔP$_{rfaH178}$) induced significantly greater protection than did immunization with χ9884(pYA4088) (ΔrfaH49) (P<0.05). There was no significant difference between the protective efficacy of χ9241(pYA4088) and the other strains expressing pspA (P>0.05). All of the mice that died in these experiments succumbed within 4 days after challenge.

Increased Immunogenicity of Conserved Antigens Against Different Enteric Bacteria.

Figure 7:
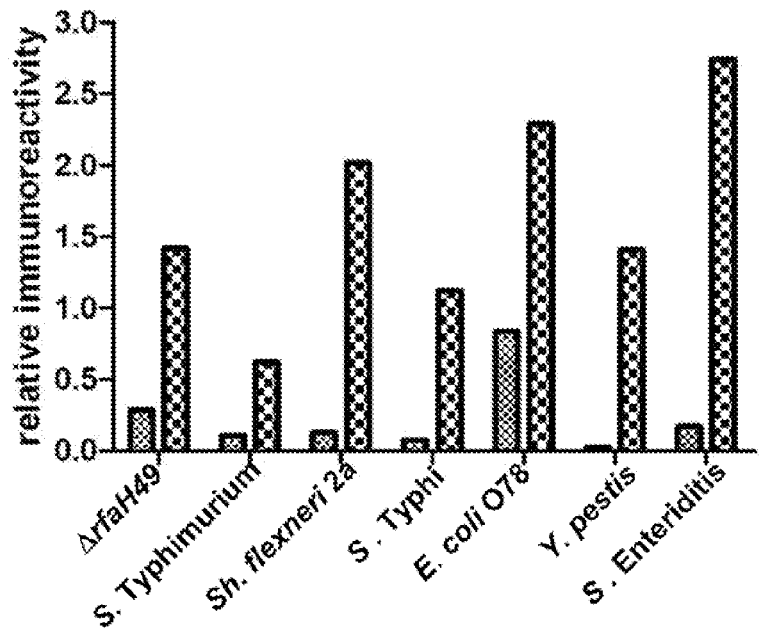
FIG. 7. Relative reactivity of immune sera, taken 6 weeks after the primary immunization, to homologous and heterologous bacteria from mice immunized with χ9241(pYA4088) and its mutant derivatives. Pooled immune sera from mice immunized by χ9884(pYA4088) (ΔrfaH49), χ9852 (pYA4088) ($\Delta P_{rfaH178}$) and χ9241(pYA4088) (parent vaccine strain) were tested against whole cells (A) or purified outer membrane proteins (B) from different enteric bacteria by indirect ELISA. Reactivity is expressed relative to that of χ9241(pYA4088) immune serum at the same dilution. Means of values from 3 independent experiments are shown. All χ9852(pYA4088) groups were significantly different from the χ9884(pYA4088 groups (P<0.001). (ΔrfaH49 χ9945; *S. Typhimurium* χ3761; *Shigella flexneri* 2a wild-type 2457T; *Salmonella Typhi* ISP1820; *Escherichia coli* O78, χ7122; *Yersinia pestis* KIM6+; *S. Enteriditis* χ3550 (Group D1).
Figure 7:
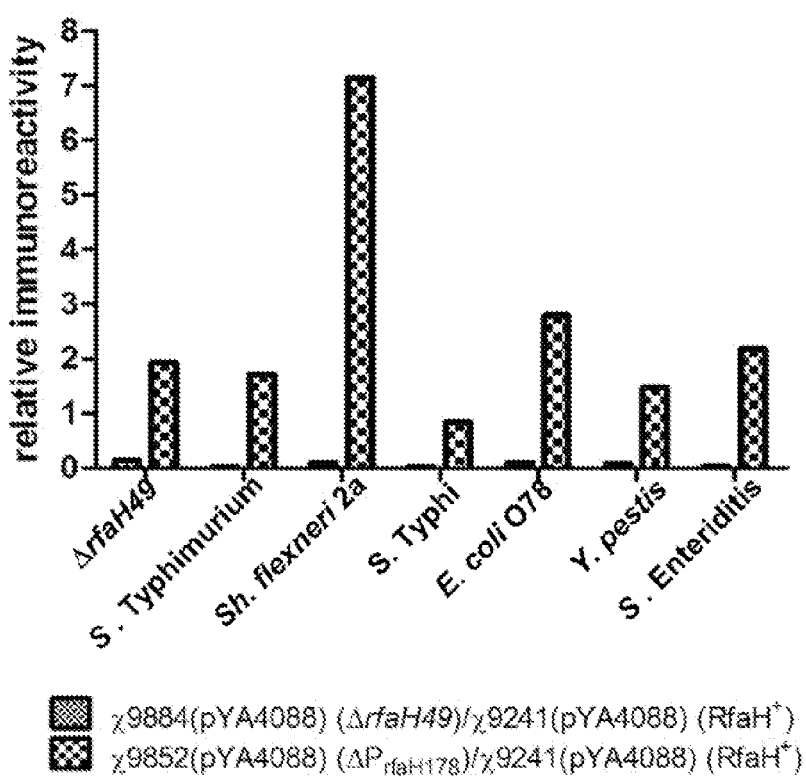

Previous work has shown that a ΔrfaH mutation increased the immunogenic reactivity of conserved minor epitopes from other enteric bacteria (42). Therefore, we examined the cross-reactive antibodies elicited by the ΔrfaH49 vaccine strain χ9884(pYA4088) with those elicited by the arabinose regulated ΔP$_{rfaH178}$ strain χ9852(pYA4088) and the RfaH$^+$ strain χ9241(pYA4088). The reactivity of pooled immune sera (11-16 mice per group) from groups of mice inoculated in the previous experiment taken two weeks after boosting was evaluated by ELISA against a panel of homologous and heterologous wild-type strains as well as their outer membrane proteins (FIG. 7). In each case, immunization with the arabinose regulated rfaH strain χ9852(pYA4088) generated higher titers against both whole cells and OMPs isolated from a diverse group of gram-negative organisms, including *S. Typhimurium, Salmonella enterica* serovars *Typhi* and *Enteriditis, Shigella flexneri, E. coli,* and *Yersinia pestis* than the ΔrfaH49 strain χ9884(pYA4088).

Discussion

Recombinant attenuated *S. Typhimurium* strains have been used extensively as multivalent vectors expressing heterologous antigens. An ideal RASV should be able to invade and transiently persist in lymphoid tissues (PP, spleen, liver) to stimulate both strong primary and lasting memory immune responses, cause no disease symptoms and be susceptible to all clinically useful antibiotics (2, 9, 10). Achieving this balance between adequate attenuation/safety and ability to elicit long-lasting protective immunity is not always easy or straightforward. We have developed several strategies to address this issue, including regulated delayed attenuation (13, 14, 29), whereby the live vaccine strain displays abilities similar to a wild-type virulent parental pathogen to successfully colonize effector lymphoid tissues before display and imposition of the fully attenuated phenotype, and regulated delayed antigen synthesis in which the expression of a heterologous antigen gene is delayed until the vaccine strain has colonized host tissues (71).

Figure 5:
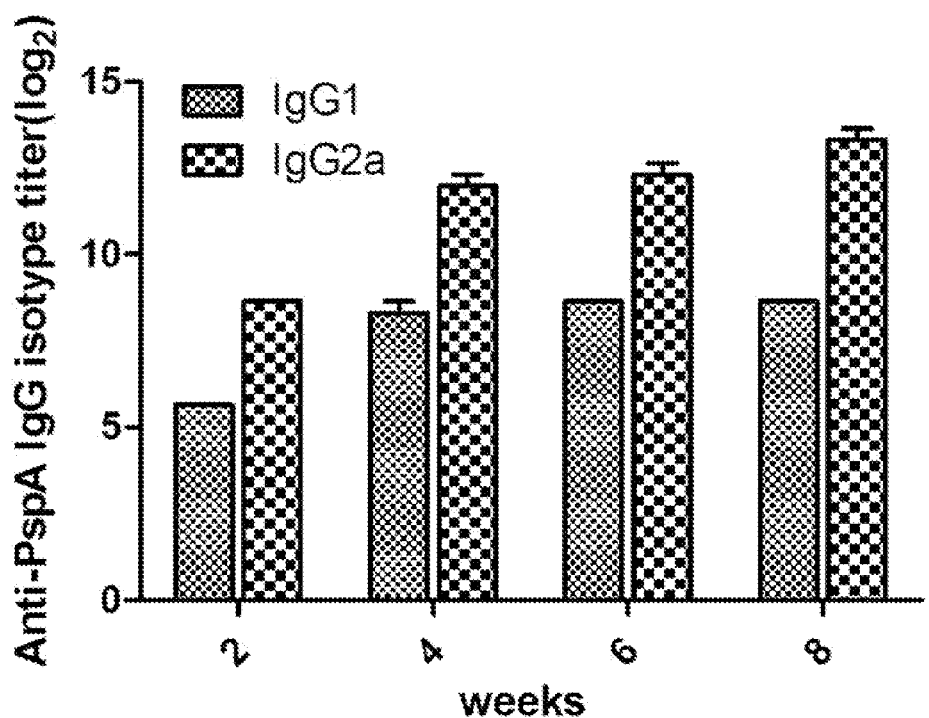
FIG. 5. Serum IgG1 and IgG2a responses to rPspA. The data represent ELISA results determining IgG1 and IgG2a subclass antibody levels to rPspA in sera of BALB/c mice orally immunized with (A) χ9241(pYA4088)(RfaH+), (B) χ9852 (pYA4088)($\Delta P_{rfaH178}$), or (C) χ9884(pYA4088) (ΔrfaH49) at the indicated weeks after immunization.
Figure 5:
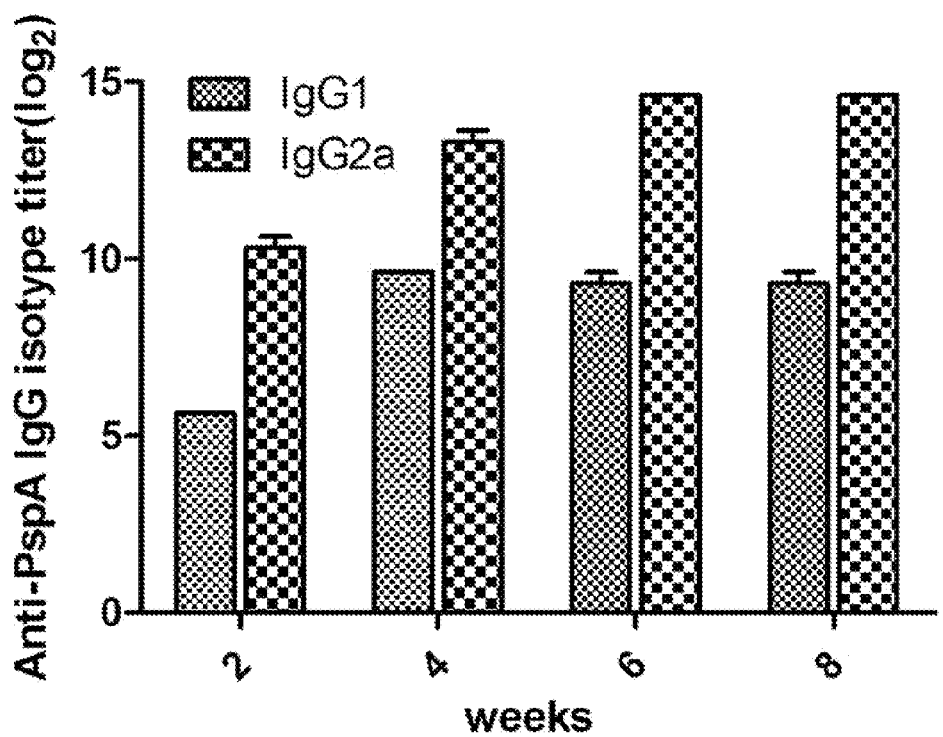
Figure 5C:
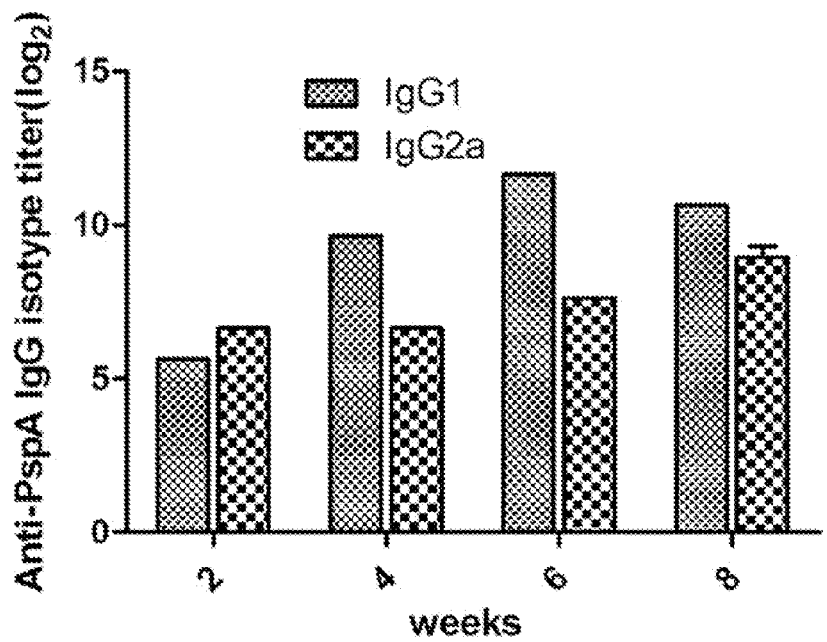

In this work we have applied the regulated delayed attenuation approach to produce strains with arabinose-regulated synthesis of RfaH, a transcriptional antiterminator required for production of complete LPS (38, 54) and for transcription of other virulence-associated genes including the sii operon, which contributes to the intestinal phase of infection (38); We compared arabinose-regulated rfaH expression strains to a ΔrfaH strain. Based on P22 transduction assays, the ΔrfaH mutant produced some full-length O-antigen (Table 3) undetectable on silver stained gels (FIG. 1), consistent with a previous report (42). When grown without arabinose, the regulated delayed rfaH strains produced O-antigen detectable by silver stain, although the amount was reduced compared to the same strains grown with arabinose or to strains expressing wild-type rfaH (FIG. 1; Table 3). A ΔrfaH mutant of *S. Typhimurium* has been shown to induce protection against challenge with wild-type *S. Typhimurium* (39). However, a potential drawback of this strain is its innate sensitivity to host antimicrobial agents such as bile and antimicrobial peptides (38) (Table 3). This, in addition to the lack of complete O-antigen, could lead to reduced colonization of lymphoid tissues (FIG. 3), an important criterion for stimulation of a strong, lasting immune response. When grown in the presence of arabinose, the phenotype of the $\Delta P_{rfaH178}$ mutant was similar to its wild-type parent, χ3761 (FIG. 1, FIG. 3, and Table 3). In the absence of arabinose, this mutant was nearly as susceptible as the ΔrfaH mutant to deoxycholate and polymyxin B. In addition, even when grown in the presence of arabinose, the $\Delta P_{rfaH178}$ mutant was attenuated with an $LD_{50}$ 100× greater than χ3761, although not as attenuated as the ΔrfaH mutant (Table 3). To ensure safety of live *Salmonella* vaccines, it is critical that the strain carry at least two, genetically unlinked attenuating mutations (15, 51, 66). Therefore, we evaluated the ΔrfaH mutation and the arabinose-regulated rfaH mutation $\Delta P_{rfaH178}$ in combination with the ΔpabA ΔpabB mutations in strain χ9241 and introduced plasmid pYA4088, which directs synthesis of a heterologous antigen, the pneumococcal protective antigen PspA (5, 34). The ΔrfaH derivative χ9884(pYA4088) colonized mouse tissues poorly compared to its parent, χ9241(pYA4088), typical of strains lacking full-length O-antigen (49, 54). However, the strain with the $\Delta P_{rfaH178}$ mutation χ9852(pYA4088) colonized host spleen and liver nearly as well as χ9241(pYA4088). Furthermore, mice immunized with two doses of χ9852(pYA4088) elicited an anti-PspA IgG response equal to or greater than that induced by χ9241(pYA4088) (FIG. 4). Mice immunized with the ΔrfaH mutant, χ9884(pYA4088), also developed anti-PspA serum IgG antibodies, although the titers were significantly lower than χ9241(pYA4088) or χ9852 (pYA4088). In addition, mice immunized with either χ9241 (pYA4088) or χ9852(pYA4088) developed much higher titers of IgG2a compared to the ΔrfaH strain χ9884 (pYA4088) (FIG. 5). IgG2a antibody is the most potent isoform for directing complement deposition, an important host mechanism for clearing *S. pneumoniae* (6).

Figure 6:
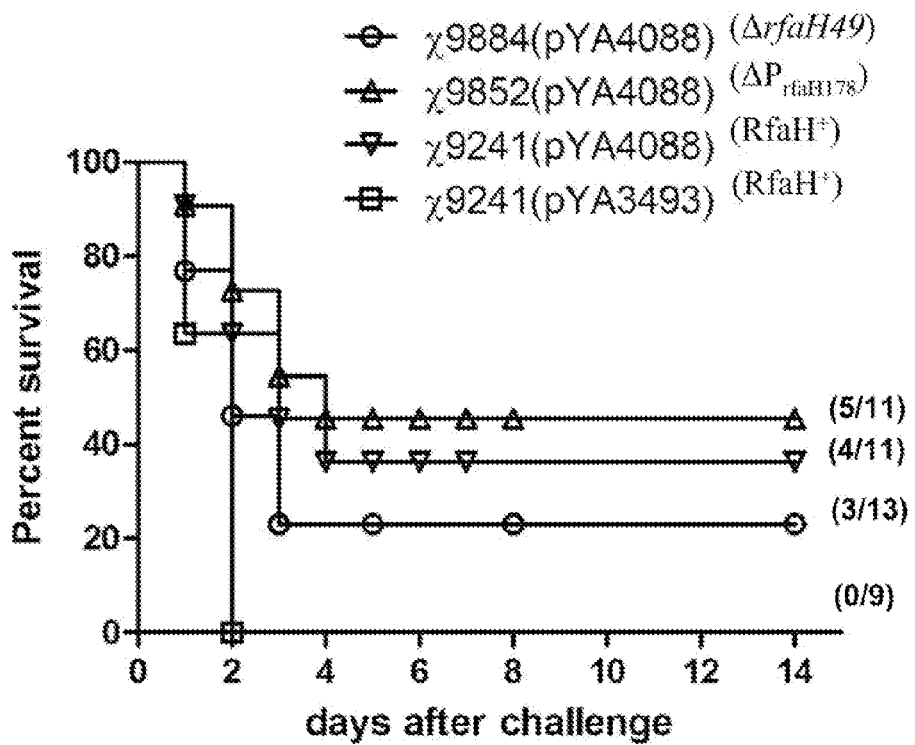
FIG. 6. Oral immunization with PspA-expressing *Salmonella* strains protects BALB/c mice against i.p. challenge with *S. pneumoniae* WU2, 9 (control) or 11-13 (vaccine) mice per group were orally immunized twice at 4-weeks intervals with the indicated vaccine strains. Mice were challenged with $4\times10^4$ CFU of *S. pneumoniae* WU2 ($200\times LD_{50}$) 4 weeks after the second oral immunization. Mortality was monitored for 3 weeks after pneumococcal challenge. The numbers in parentheses refer to the number of surviving [34] mice/the number of total mice per group. All vaccine groups were significantly different from the χ9241 (pYA3493) control (P<0.01). χ9884 (pYA4088) vs. χ9852(pYA4088): P=0.0326.

When challenged i.p. with virulent *S. pneumoniae*, all groups immunized with strains expressing pspA were protected (FIG. 6). Consistent with the colonization and serum antibody data, immunization with the regulated rfaH expression strain χ9852(pYA4088) provided significantly greater protection than the ΔrfaH strain χ9884(pYA4088) (P<0.05). These results support the notion that delaying expression of an attenuation phenotype increases protective efficacy (13, 14, 29).

In our laboratory, we are interested in developing vaccines against enteric pathogens, including pathogenic *E. coli*, enteric *Yersinia* species and *Shigella*. This is an area in which *S. Typhimurium* rfaH mutants may be valuable by inducing cross-protective antibodies against other enteric bacteria (42). Down-regulating the production of O-antigen, the major immunodominant antigen in *Salmonella*, has been shown to enhance the immunogenicity of conserved antigens (14). A recent study showed that mice immunized with a ΔrfaH mutant produced higher titers of serum antibodies against conserved antigens from different *Salmonella enterica* serovars and from other enteric organisms than an attenuated smooth strain (39, 42). The ΔrfaH ΔpabA ΔpabB strain χ9884 (pYA4088), induced an enhancement of cross-reactive antibodies to only itself and the avian pathogenic *E. coli* strain χ7122, but not to smooth, wild-type *S. Typhimurium*, *S. enterica* serovar *Typhi*, *S. enterica* serovar *Enteriditis*, *Shigella flexneri* or *Yersinia pestis* (FIG. 7A) or outer membrane proteins derived from these strains (FIG. 7B). The differences between our results and those previously reported could possibly be due to differences in time of serum collection, the number of boosts, strain background and/or the presence in our strains of additional attenuating mutations and plasmid pYA4088, directing synthesis of a heterologous antigen. In addition, we used χ9241(pYA4088) as the base strain to develop our ratios, while a ΔaroA strain was used in the previous study. Importantly, immunization with the arabinose-regulated rfaH strain χ9852(pYA4088) enhanced production of cross reactive antibodies to all strains tested, including strong responses against *S. Enteriditis*, *Shigella*, avian pathogenic *E. coli* and *Yersinia*. These results are most likely due to the overall higher immunogenicity of χ9852 (pYA4088) than χ9884(pYA4088) (FIG. 4), which, in turn, is probably related to the poor colonization of host tissues observed for χ9884(pYA4088) (FIG. 3). These results indicate that inclusion of the $\Delta P_{rfaH178}$ mutation in an RASV expressing pathogen-specific antigens designed to protect against *Shigella*, *E. coli* and/or *Yersinia* could enhance the protective efficacy against these pathogens. We stated previously that it would be advantageous to reduce the host immune response against the RASV carrier, thereby enhancing the immune response against the heterologous antigen. One of our goals for this study was to determine whether in vivo down regulation of rfaH would suppress the immune response against carrier specific 0 antigen. For this application, the $\Delta P_{rfaH178}$ mutation was not as useful as we had hoped. Although the immune response against LPS O-antigen was delayed in mice immunized with χ9852(pYA4088) compared to χ9241(pYA4088) (FIG. 4), by week 8, mice immunized with either strain had developed nearly identical anti-LPS titers. There are several possible explanations for this result. One is that a mutation arose in vivo that allowed for arabinose-independent rfaH expression in χ9852(pYA4088). This is unlikely, as we did not observe any such mutants in the spleen isolates we tested. While the araC $P_{BAD}$ promoter cassette used in this study is tightly regulated in vivo, as we established in a previous study (27), it is possible that low levels of non-phosphorylated arabinose in the mouse diet may have been sufficient to allow enough rfaH expression to permit full length O-antigen synthesis. In addition, χ9852 (pYA4088) was grown in the presence of arabinose, conditions permissive for rfaH expression, and given as a boost on day 28, which may have also played a role in generating the observed high anti-LPS antibody titers. A final possible explanation is that our ELISA coating antigen was complete LPS, which includes lipid A, core and O-antigen. One might expect better presentation of LPS core to the mouse immune system by the rfaH mutant strains compared to χ9241 (pYA4088), leading to an increase in anti-core antibody titers. Our ELISA was not designed to distinguish between anti-core and anti-O-antigen antibodies. This question will be investigated in a future study to answer this question. This is an interesting question since these anti-core antibodies may be cross-reactive with and potentially cross-protective against other enteric bacteria that share the same core structure. In summary, we have shown that rfaH mutations can be combined with other attenuating mutations to produce vaccine an RASV capable of delivering a protective antigen to induce protective immunity. The delayed regulated mutation, $\Delta P_{rfaH178}$ in combination with $\Delta pabA$ $\Delta pabB$ mutations was superior to a $\Delta pabA$ $\Delta pabB$ $\Delta rfaH$ strain in colonizing lymphoid tissues, eliciting serum antibodies to a heterologous antigen and inducing protective immunity against S. pneumoniae challenge. Notably, the $\Delta P_{rfaH178}$ vaccine was more effective than the isogenic $\Delta rfaH$ strain at inducing antibodies cross reactive with a number of other enteric pathogens, making it suitable for inclusion in vaccines to protect against enteric diseases.

Example 2 rfc Mutations

The use of attenuated bacteria as vaccine delivery vehicles for heterologous antigens has been studied extensively in both animals and humans. Attenuated *Salmonella* is the best choice due its ability to, when given orally, stimulate both cell and humoral-mediated immunity against a heterologous antigen and thus provide protection against pathogen challenge (7, 10, 12). A good live oral *Salmonella* vaccine would retain its ability to colonize and invade host lymphoid tissues but would be completely avirulent after oral administration (35). The lipopolysaccharide of *Salmonella* is a recognized virulence determinant, and contributes to several stages of the infectious process, including swarming motility (64), intestinal colonization (46), serum resistance (57), invasion/intracellular replication (38), and resistance to killing by macrophages. Rough *Salmonella* strains that do not make the O-antigen side chains or outer core or inner core sugar were not able to survive the succession of stresses encountered in vivo and were less virulent than the smooth *Salmonella* strain (21, 36). Therefore, due to their hyperattenuation, structural rough mutants have been considered to be inappropriate live vaccine carriers (41). There are currently many other attenuating mutations being investigated by researchers involved in vaccine development (7, 12, 14), but it is a good choice to manipulate the LPS synthesis genes when developing a recombinant attenuated *Salmonella* vaccine. Theoretically, a moderate decrease in the number and/or length of LPS chains can lead to attenuation paralleled by retained immunogenic potential to deliver the heterologous antigen.

Three *Salmonella Typhimurium* strains have apparently provided attenuation through modification of LPS. Two of these mutations, galE and pmi, are involved in synthesizing the sugars of LPS. GalE is a UDP-galactose epimerase that inter-converts UDP-glucose and UPD-galactose, an essential part of core sugar and O-antigen. This mutant synthesized core-defective LPS in the absence of galactose but made normal LPS when galactose was available in the growth media. The avirulence of this mutant in the murine model of Typhoid was thought to be due to the fact that the strains were susceptible to galactose-induced lysis (18, 24, 59). However, this same mutation, transferred to *S. Typhi*, was not attenuated and was poorly immunogenic in humans (23). Following a similar concept, a pmi knockout in *S. Typhimurium* was constructed and evaluated in our lab (14, 29, 11). Pmi is a phosphomannose isomerase, which converts fructose-6-P to mannose-6-P, and, in vivo, the deletion mutant is unable to synthesize the O-antigen due to unavailability of mannose, which is a component of O-antigen. When the mutant is grown in the presence of mannose, the smooth LPS phenotype is exhibited. This mutant was attenuated but also showed high immunogenicity and efficacy in enhancing induction of high antibody titers to cross-protective OMPs, however, the pmi deletion in *Typhi* has not yet been evaluated in humans, and this mutation will cause other phenotype modification in *S. Typhimurium* except LPS. Both galE and pmi mutant strains transiently express LPS before colonizing the GALT or organs (14, 22). Another gene involved in LPS biosynthesis, rfaH, was evaluated in BALB/c mice (38, 42). RfaH is a transcriptional anti-terminator, and is involved in the synthesis of many virulence determinants including O-antigen, core sugar, capsular polysaccharide, and Vi antigen (38). An rfaH deletion mutant, described as "gently rough", exhibited some deep-rough characteristics, i.e. lack of O-antigen and outer core, sufficient attenuation, susceptibility to detergents and to some antibiotics, but still proved to be immunogenic (42).

Rfc (Wzy) is a polymerase responsible for polymerizing the O-unit, and, in conjunction with Wzx (transporter), Wzz (length determinant) and WbaP (O-antigen synthesis initiation), synthesizing, assembling, and transporting the O-antigen to the periplasm, where WaaL (Ligase) ligates O-antigen to lipid A to form complete LPS (48, 65, 67). The mutant with an rfc deletion constitutively makes LPS with a single O-unit in each core molecule, which is designated as a semi-rough phenotype. *Salmonella* with an rfc mutation exhibited good colonization and immunogenic attributes against *S. Typhimurium* when orally inoculated into BALB/c mice (11). A tightly regulated araC $P_{BAD}$ activator-promoter has been used extensively in our lab to regulate gene expression (13, 14). We replaced the rfc promoter with an araC $P_{BAD}$ promoter to create arabinose inducible production of Rfc and thus regulate rfc expression to mimic transient expression of smooth LPS; this is similar to the manner in which the galE or pmi phenotypes are controlled by the availability of, galactose or mannose. It is of interest to evaluate the ability of each mutant to deliver heterologous antigen to the host immune system and the strains' ability to protect the host against subsequent challenge.

*Streptococcus pneumoniae* is the most important bacterial pathogen causing pneumonia in children and older adults. Pneumococcal conjugate vaccine (PCV) is effective in reducing invasive pneumococcal disease and pneumonia in humans. Unfortunately, there are many drawbacks to this widely used vaccine, such as: expensive costs (more than $200 per child), chemical contamination, serotype-replacement, poor immunogenicity, and short-term protection (no immunological memory) in infants and older adults. It is urgent that we develop a new efficient vaccine to broadly protect humans against pneumonia. A pneumococcal surface protein, PspA, is a protective antigen, and the immune response raised against it has been shown to protect against challenge by virulent *S. pneumoniae* (5).

In this work, we constructed a series of rfc mutations in our recombinant attenuated *Salmonella* vector (RASV), and, after immunizing mice with the mutant RASVs harboring a plasmid expressing pspA, evaluated the murine immune response and degree of protection afforded to the mice against challenge by *S. pneumonia* WU2.

Materials and Methods

Bacterial Strains, Plasmids, Media, and Growth Conditions.

The bacterial strains and plasmids used in this study are listed in Table 1. *S. Typhimurium* cultures were grown at 37° C. in Luria broth (LB) (4), nutrient broth (NB) (Difco) or on Luria agar (LA) with or without 0.1% arabinose. Selenite broth, with or without supplements, was used for enrichment of *S. Typhimurium* from mouse tissues. DAP was added (50 µg/ml) for the growth of Δasd strains (43). LA containing 5% sucrose was used for sacB gene-based counterselection in allelic exchange experiments. *S. pneumoniae* WU2 was cultured on brain heart infusion agar containing 5% sheep blood or in Todd-Hewitt broth plus 0.5% yeast extract, and were kept at −80° C. for future use. MOPS minimal medium (45) with/without 10 µg/ml p-aminobenzoic acid (pABA) was used to confirm the phenotype of ΔpabA ΔpabB mutants.

Plasmids and Mutant Strain Construction.

DNA manipulations were carried out as previously described (52). Electroporation was used to transform *E. coli* and *S. enterica*. Transformants were selected on LA plates containing appropriate antibiotics. Strains were grown on LA without supplement to select for bacteria harboring the Asd+ plasmid. The primers used in this work are listed in Table 2. A 500-bp DNA fragment containing the region upstream of the rfc promoter ($P_{rfc}$) was PCR amplified using the *S. Typhimurium* χ3761 genome as template with primers Rfc1-FXmaI-pstI and Rfc1-RPstI (Table 2). The amplicon was digested with PstI and ligated into the PstI site of vector pYA3700 (Table 1). This placed the promoter just upstream of araC. Primer T4TT-R, which binds to the T4 transcriptional terminator antisense sequence present downstream of the PstI site in pYA3700, and primer Rfc1-RPstI were used to screen plasmid isolates for inserts in the correct orientation. This intermediate plasmid was digested with XhoI and KpnI, restriction sites that lie downstream of the araC $P_{BAD}$ cassette. Three different 0.5 kb PCR fragments of rfc gene were amplified from the *S. Typhimurium* χ3761 genome, using three different upstream primers, Rfc2-FXhoI, Rfc2-1, and Rfc2-2, and the same downstream primer Rfc2-RkpnI. Each PCR fragment was engineered to encode a different Shine-Dalgarno (SD) sequence and/or start codon (Table 1) due to the differences in the upstream primers. The PCR fragments were digested with XhoI and KpnI and inserted into the intermediate plasmid described above. The three resulting constructs were confirmed by DNA sequence analysis. Then, 2.5-kb DNA fragments encoding araC $P_{BAD}$ rfc and rfc 5' and 3' flanking regions were excised from each of the plasmids by digestion with KpnI and XmaI and inserted into pRE112, resulting in plasmids pYA4297, pYA4298, and pYA4299. To construct the Δrfc-48 deletion, two pairs of primers Rfc-1F/Rfc-1R and Rfc-2F/Rfc-2R were used to amplify approximately 300-bp fragments upstream and downstream of rfc, respectively, from the χ3761 genome. The two PCR fragments were purified from agarose gels and were used as template at a 1:1 molar ratio for joining by PCR using primers Rfc-1F and Rfc-2R. The resulting PCR product was digested with KpnI and XmaI and ligated into plasmid pRE112, digested with the same two enzymes, resulting in plasmid pYA4717, which carries a deletion of the entire rfc gene from ATG to TAA. The mutations were introduced into *S. Typhimurium* χ3761 by allelic exchange using the four suicide vectors pYA4717, pYA4297, pYA4298 and pYA4299 to generate χ9944, χ9659, χ9736, χ9737, respectively. The Δrfc-48 and $\Delta P_{rfc174}$ mutations were also introduced into *S. Typhimurium* strain χ9241 to yield strains χ9885 and χ9853, respectively. The presence of both ΔpabA1516 and ΔpabB232 mutations in *S. Typhimurium* strains χ9241, χ9885 and χ9853 were verified by the inability of the strains to grow in MOPS minimal medium without p-aminobenzoate. The presence of ΔasdA16 mutation was confirmed by PCR and by strains' inability to grow in media without DAP. The ΔaraBAD23 mutation was verified by PCR and by its white colony phenotype on MacConkey agar supplemented with 1% arabinose. LPS profiles of *Salmonella* strains were examined by the methods of Hitchcock and Brown (20) using cultures standardized based on $OD_{600}$.

P22 Transduction Studies.

P22HT int (56) was propagated on *S. Typhimurium* strain χ9430 carrying the integrated suicide plasmid pYA4284, which confers chloramphenicol resistance. Strains to be tested were grown overnight in NB at 37° C. Cultures were diluted 1:100 into fresh, prewarmed nutrient broth with or without 0.1% arabinose and grown at 37° C. to an $OD_{600}$ of 0.9. Then, 10 µl of phage was added to 1 ml of cells ($5 \times 10^8$ CFU) and the mixture was incubated at room temperature for 30 min, centrifuged and resuspended in 200 µl of buffered saline with gelatin (BSG). A 100 µl aliquot was spread onto LA plates containing 15 µg/ml chloramphenicol and incubated overnight at 37° C. Colonies were counted the following day. This experiment was performed twice.

Minimum Inhibitory Concentration (MIC) Test.

The MICs of different antimicrobial substances were determined using 96-well microtitre plates (69). Two fold serial dilutions of the bile salt deoxycholate (0.1 to 50 mg/ml) and polymyxin B (0.1 to 10 µg/ml) were made down the plates. Bacteria were grown until they reached an $OD_{600}$ of 0.8-0.9 in NB with or without 0.1% arabinose and washed in PBS. Cells were diluted to $1.0 \times 10^5$ to $1.0 \times 10^6$ CFU in NB with or without arabinose. Then 0.1 ml of the diluted cell suspension was added to each well. The microtitre plates were incubated overnight at 37° C. The optical density of each culture was determined using a SpectraMax M2e (Molecular Devices, CA) plate reader. The threshold of inhibition was 0.1 at $OD_{600}$. Actual titers were determined by spreading culture dilutions onto LA plates followed by overnight incubation at 37° C. Assays were repeated at least three times.

Swimming.

Swimming motility was assessed on LB plates solidified with 0.3% agar supplemented with 0.5% glucose with or without 0.1% arabinose. The plates were allowed to dry at room temperature for 2 h. Freshly grown bacteria were collected from LB agar plates without arabinose, washed and diluted in saline. Six microliters of bacterial suspension (approximately $1 \times 10^6$ CFU) was spotted onto the middle of the plates, which were subsequently incubated at 37° C. for 6 h. The diameter of the swarming colonies were measured. Experiments were repeated three times.

Determination of Virulence in Mice.

Seven week old, female BALB/c mice were obtained from the Charles River Laboratories. The Arizona State University Animal Care and Use Committees approved all animal procedures. Mice were acclimated for 7 days after arrival before starting the experiments.

For determination of the 50% lethal dose ($LD_{50}$), bacteria were grown statically overnight at 37° C. in LB broth, diluted 1:50 into fresh media containing 0.1% arabinose, and grown with aeration (180 rpm) at 37° C. When the cultures reached an $OD_{600}$=0.8-0.9, they were harvested by room temperature centrifugation at 4,000 rpm, washed once, and normalized to the required inocula density in BSG by adjusting the suspension to the appropriate $OD_{600}$ value. Groups of five mice each were infected orally with 20 μl containing various doses of S. Typhimurium χ3761 or its derivatives, ranging from $1.0\times10^3$ CFU to $1.0\times10^8$ CFU. Animals were observed for 4 weeks post infection, and deaths were recorded daily.

To evaluate colonization, mice were orally inoculated with 20 μl of BSG containing $1.0\times10^9$ CFU of each strain. At days 4 and 8 after inoculation, three animals per group were euthanized and their spleens and livers were collected. Each sample was aseptically weighed and then homogenized in a total volume of 1 ml BSG dilutions of $10^{-1}$ to $10^{-6}$ (depending on the tissue) were plated onto MacConkey agar and LB agar, each containing 0.1% arabinose, to determine the number of viable bacteria. A 0.1 ml aliquot of each tissue sample was inoculated into selenite cysteine broth. Samples that were positive by enrichment in selenite cysteine broth for 14 h at 37° C. were recorded as <10 CFU/g.

Immunogenicity of Vaccine Strains in Mice.

RASV strains were grown statically overnight in LB broth with 0.1% arabinose at 37° C. The following day, 2 ml of the overnight culture was inoculated into 100 ml of LB broth with 0.1% arabinose and grown with aeration at 37° C. to an $OD_{600}$ of 0.8 to 0.9. Cells were harvested by room temperature centrifugation at 4,000 rpm for 15 min and the pellet resuspended in 1 ml of BSG. Mice were orally inoculated with 20 μl of BSG containing $1\times10^9$ CFU of each strain on day 0 and boosted on day 28 with the same dose of the same strain. Blood was obtained by mandibular vein puncture at biweekly intervals. Blood was allowed to coagulate at 37° C. for two hours. Following centrifugation, the serum was removed from the whole blood and stored at −20° C.

Antigen Preparation.

The rPspA protein was purified as described (25). The rPspA clone, which encodes the α-helical region of PspA (aa 1-302) in pET20b, was a kind gift from Dr. Susan Hollingshead at the University of Alabama at Birmingham. S. Typhimurium LPS was purchased from Sigma. Outer membrane proteins were prepared as described (25). To prepare whole cell antigens, various enteric bacteria were grown statically overnight at 37° C. in LB broth, diluted 1:50 into fresh media, and grown with aeration (180 rpm) at 37° C. to an $OD_{600}$=0.8-0.9. Cells were harvested by centrifugation at 4,000 rpm, washed once in PBS, and suspending in coating buffer (50 mM $Na_2CO_3$, 50 mM $NaHCO_3$, 0.1% sodium azide, pH 9.6) to an $OD_{600}$=0.8. Then, 100 μl/well of the resulting cell suspension was used to coat the ELISA plate overnight at 4° C.

SDS-PAGE and Western Blot Analyses.

Protein samples were boiled for 5 min and then separated by SDS-PAGE. For western blotting, proteins separated by SDS-PAGE were transferred electrophoretically to nitrocellulose membranes. The membranes were blocked with 3% skim milk in 10 mM Tris-0.9% NaCl (pH 7.4) and incubated with rabbit polyclonal antibodies specific for PspA (71) or GroEL (Sigma, St. Louis, Mo.). The secondary antibody was an AP-conjugated goat anti-rabbit immunoglobulin G (IgG) (Sigma). Immunoreactive bands were detected by the addition of BCIP/NBT solution (Sigma). The reaction was stopped after 2 min by washing with large volumes of deionized water.

Enzyme-Linked Immunosorbent Assay (ELISA).

ELISA was used to assay serum antibodies against S. Typhimurium LPS, rPspA, outer membrane proteins and whole cell bacterial suspensions ($1\times10^9$ CFU/ml) as previously described (30). Color development (absorbance) was recorded at 405 nm using a SpectraMax M2e automated ELISA plate reader (Molecular Devices, CA). Absorbance readings 0.1 nm higher than PBS control values were considered positive.

Measurement of Cytokine Concentrations.

Cytokine concentrations were determined by using the Bio-Plex Protein Array System (Bio-Rad) according to the kit's protocol. Cytokine-specific antibody-coated beads were used for these experiments; serum samples were diluted with specific serum dilution buffer (Bio-Rad), and then were incubated with antibody-coupled beads for 30 min with continuous shaking. The beads were washed 3 times with 100 μl wash buffer to remove unbound protein and then incubated with biotinylated cytokine-specific antibody for 30 min with continuous shaking. The beads were washed three times and were then incubated with streptavidin-phycoerythrin for 10 minutes. After incubation, the beads were washed three times in washing buffer and resuspended in 125 μl assay buffer. The constituents of each well were drawn up into the flow-based Bio-Plex suspension Array System, which indentifies each different color bead as a population of protein and quantifies each protein target based on secondary antibody fluorescence. Cytokine and chemokine concentrations were calculated by Bio-Plex Manager software using a standard curve derived from a recombinant cytokine standard, and two reading were made on each bead set.

Pneumococcal Challenge.

We assessed the protective efficacy of immunization with the attenuated Salmonella expressing pspA at week 8 by intraperitoneal (i.p.) challenge with $4\times10^4$ CFU of S. pneumoniae WU2 in 200 μl of BSG (44). The $LD_{50}$ of S. pneumoniae WU2 in BALB/c mice was $2\times10^2$ CFU by i.p. administration (data not shown). Challenged mice were monitored daily for 30 days.

Statistical Analysis.

Antibody titers were expressed as geometric means and the relative immunoreativity was expressed as an arithmetic mean. The means were evaluated with two-way ANOVA and Chi square test for multiple comparisons among groups. $P<0.05$ was considered statistically significant.

Results

Mutant Construction and LPS Phenotypes.

Mutants designed to express various levels of Rfc were constructed as described in Materials and Methods. FIG. 8A illustrates the chromosomal structure of the araC $P_{BAD}$ rfc mutant strains. Two-hundred and eighty-five base pairs upstream from the rfc start codon were replaced with araC $P_{BAD}$ and either a different Shine-Delgarno (SD) sequence, a changed ATG/GTG start codon, or both. Table 1 shows the SD and start codon sequence for each mutant strain.

Figure 8:
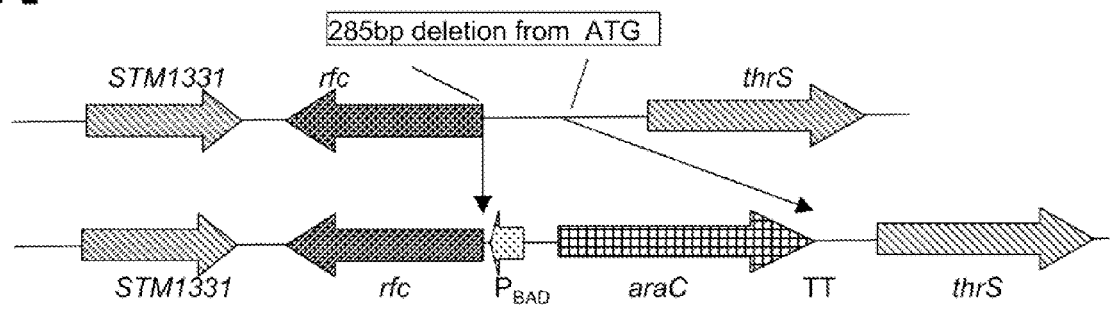
FIG. 8. (A) map for deletion-insertion mutations resulting in arabinose-regulated rfc expression. (B) lipopolysaccharide (LPS) phenotypes of wild type *Salmonella Typhimurium* χ3761 and its isogenic rfc mutant strain, purified LPS from different mutant strains growing in Nutrient Broth with/without 0.1% arabinose were silver stained after separation by 12% SDS-PAGE. (C) western blotting against LPS from B.
Figure 8:
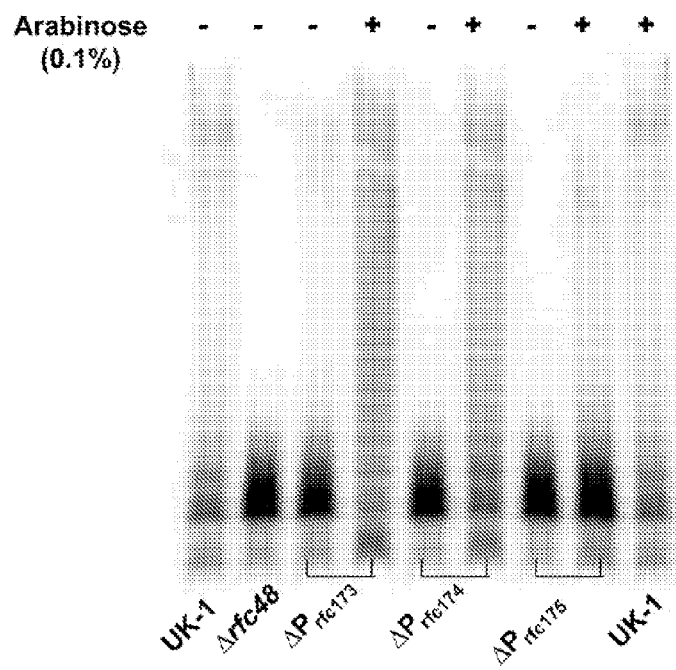
Figure 8C:
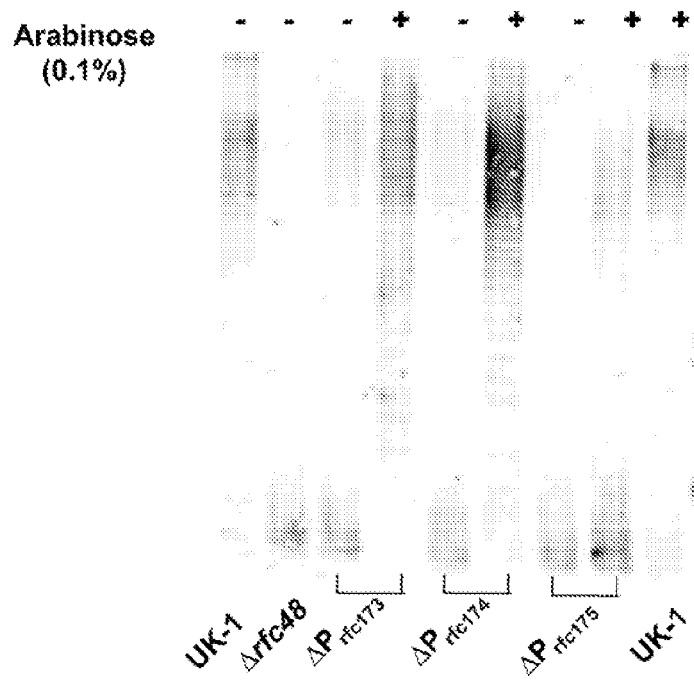

The effect of the rfc mutation on the LPS phenotypes was revealed by SDS-PAGE with silver staining (FIG. 8B) and by Western blotting against Salmonella Group B O-antigen (FIG. 8C). Deletion of rfc resulted in semi-rough O-antigen, but the other three mutants with promoter replacement have some semi-rough O-antigen with part of complete O-antigen in nutrient broth without arabinose. Growth in the presence of arabinose resulted in synthesis of full-length O-antigen in the araC $P_{BAD}$ rfc strains, but not in the χ9885 (Δrfc-48) strain. Only χ9736 ($\Delta P_{rfc174}$::TT araC $P_{BAD}$ rfc) resulted in an LPS pattern similar to the wild-type Salmonella UK-1. However, the χ9659 ($\Delta P_{rfc173}$::TT araC $P_{BAD}$ rfc) produced some complete O-antigen in the absence of arabinose, indicating leaky expression of rfc; the western blot also showed that this mutant with $\Delta P_{rfc173}$ araC $P_{BAD}$ rfc produced some high molecular O-antigen in Nutrient Broth without arabinose. Expression of rfc from the χ9737 ($\Delta P_{rfc175}$::TT araC $P_{BAD}$ rfc) mutant appeared to be more tightly controlled when grown without arabinose supplementation than other mutants, but the levels of Rfc were not enough to polymerize O-antigen as this strain produce more O-antigen with only one O-unit, similar to χ9944 (Δrfc-48) in nutrient broth with arabinose (FIG. 8B).

To further evaluate arabinose regulated O antigen synthesis, we performed infection studies with the S. Typhimurium O antigen-specific phage P22. Strains were grown in nutrient broth with or without arabinose and used as recipients for transduction assays. Strains χ9659 ($\Delta P_{rfc173}$::TT araC $P_{BAD}$ rfc), χ9736 ($\Delta P_{rfc174}$::TT araC $P_{BAD}$ rfc) and χ9737 ($\Delta P_{rfc175}$::TT araC $P_{BAD}$ rfc) were sensitive to transduction when grown with or without arabinose (Table 4), confirming existence of the complete O-antigen under both conditions. But the number of transductants for all three mutants decreased in Nutrient Broth without arabinose, indicating that some of O-antigen synthesis will shut down under conditions of no arabinose. In contrast, no transductants of Δrfc-48 mutant were found on the plate with $Cm^+$, indicating that P22 transduction requires multi O-unit O-antigen to bind. Our data is consistent with other reports (11).

Phenotypes of Mutant Strains.

Rough mutants, especially deep rough mutants display a pleiotropic phenotype (64). Three common features are increased susceptibility to environmental factors, loss cell surface organelles, and decreased ability to colonize the mouse intestine. We have assayed susceptibility to the different environmental factors such as the bile salt deoxycholate and the antimicrobial peptide polymyxin B and altered swarming. The results are summarized in Table 4.

The deoxycholate and polymyxin B MICs for the wild-type strain χ3761 were >4-fold higher than for the Δrfc-48 mutant χ9944 (Table 4). The three arabinose-regulated strains, had MICs for both test substances similar to the wild-type except χ9737 exhibiting only a 2-fold reduction in MIC for deoxycholate, consistent with the leaky phenotype observed for O-antigen synthesis (FIG. 8). The MICs in the absence of arabinose were identical to the Δrfc-48 strain χ9944 except χ9659 exhibiting a 2-time increase in MIC for polymyxin B, consistent with the leaky phenotype observed for O-antigen synthesis.

Rough mutants are unable to swarm, because of insufficient surface wetness (64). Swarming motility of Δrfc and arabinose-regulated rfc mutants was checked by dropping x ul onto the center of plates containing LB plus 0.3% agar. Both the χ9944 (Δrfc-48) and the three arabinose regulated mutants χ9659 ($\Delta P_{rfc173}$), χ9736 ($\Delta P_{rfc174}$) and χ9737 ($\Delta P_{rfc175}$) have the almost same swarming motility as wild type on plates without arabinose, indicating that one O-unit is sufficient to allow the strain to swarm. Arabinose-regulated rfc mutants χ9659 ($\Delta P_{rfc173}$), χ9736 ($\Delta P_{rfc174}$) and χ9737 ($\Delta P_{rfc175}$) showed higher motility than the wild-type UK-1 and χ9944 (Δrfc-48) mutant on LB plates supplemented with arabinose.

Virulence in BALB/c Mice.

Groups of female BALB/c mice received graded doses of various strains orally, and were monitored for 30 days after inoculation. The $LD_{50}$ for the strains is shown in Table 4.

The $LD_{50}$ of χ3761 ($1.0 \times 10^4$) in mice was similar to that previously observed (26). The mutant strain χ9944 (Δrfc-48) was avirulent by the oral route, as previously reported (11). The $LD_{50}$ of χ9659 ($\Delta P_{rfc173}$::TT araC $P_{BAD}$ rfc), with the original rfc promoter replacement by $P_{BAD}$, and with a new SD and start codon, was 15 fold higher than that of χ3761 when it was grown in arabinose-containing nutrient Broth prior to feeding. However, the phenotype of χ9736 ($\Delta P_{rfc174}$::TT araC $P_{BAD}$ rfc) was totally avirulent ($LD_{50} > 10^8$ CFU), even though this strain was grown in nutrient broth with 0.1% arabinose before oral administration to mice.

Mice that survived infection with the different mutants were challenged orally with $10^5$ $LD_{50}$ ($1.0 \times 10^9$) of wild-type S. Typhimurium 30 days after administration of the attenuated strains. All five mice immunized with $1.0 \times 10^8$ χ9736 ($\Delta P_{rfc174}$::TT araC $P_{BAD}$ rfc) were resistant to challenge. However, only two of five mice immunized with $1.0 \times 10^6$ χ9944 (Δrfc-48) survived after challenge by wild-type S. Typhiumurium. These data indicate that χ9736 ($\Delta P_{rfc174}$::TT araC $P_{BAD}$ rfc) was sufficiently attenuated but still retained its immunogenic characteristics.

Expression of the Pneumococcal Gene pspA in RASV Strain χ9241 Derivatives Carrying Different rfc Mutations.

To evaluate the ability of strains carrying the Δrfc-48 and $\Delta P_{rfc174}$TT araC $P_{BAD}$ rfc mutations to elicit an effective immune response in mice, mutations were introduced into χ9241 (30, 71), an attenuated S. Typhimurium strain typically used to evaluate mutations in our lab. The mutant strains χ9885 (Δrfc-48) and χ9853 ($\Delta P_{rfc174}$TT araC $P_{BAD}$ rfc) were constructed by using suicide plasmids pYA4717 and pYA4298, respectively, as described in Materials and Methods. The pYA4088 plasmid (expresses pspA under $P_{trc}$ promoter with LacI regulatory element) or the empty vector pYA3493, were electroporated into both mutants and the parent strain to check PspA and LacI expression in LB media with and without 0.1% arabinose.

Figure 9:
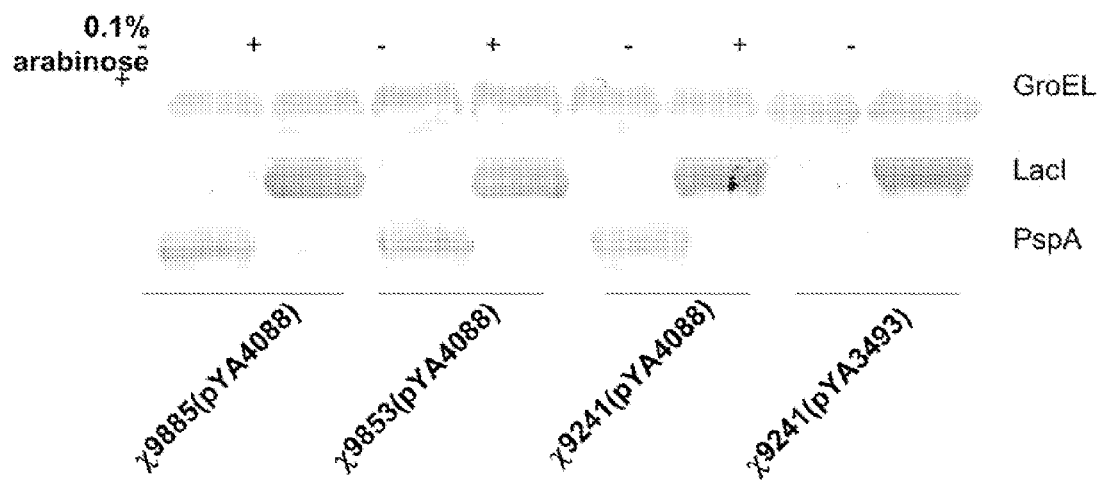
FIG. 9. PspA and LacI synthesis are regulated by 0.1% arabinose. Western blotting showing the synthesis of PspA in different rfc S. Typhimurium strains. Bacteria were grown in LB broth with or without 0.1% arabinose overnight at 37° C. Equal numbers of cells from each culture were pelleted, suspended in loading buffer, and boiled. After centrifugation, equal volumes were subjected to SDS-PAGE, transferred to nitrocellulose and probed with a polyclonal antibody specific for PspA, LacI, and GroEL, respectively. GroEL was used as a standardization marker.

FIG. 9 shows PspA and LacI expression in LB media with or without 0.1% arabinose. Whole cell lysates from strain χ9241(pYA4088), and rfc mutation strains χ9885(pYA4088) and χ9853(pYA4088) grown in LB broth with or without 0.1% arabinose, were prepared and examined by Western blot analysis (FIG. 9). All strains expressed a protein with an approximate molecular mass of 38.5 kDa, the expected size of the LacI protein that reacted specifically with an anti-LacI polyclonal antibody. No LacI was detected when the strains were grown in LB media without 0.1% arabinose. Conversely, in LB media with 0.1% arabinose, in which all strains expressed LacI, no PspA was detected. Strains carrying pYA4088 grown in the absence of arabinose produced PspA, but not LacI. There was no significant difference in PspA production for any of the strains carrying pYA4088.

Colonization of Mouse Tissues and Immune Responses in Mice after Oral Immunization with RASV Expressing PspA.

Figure 10:
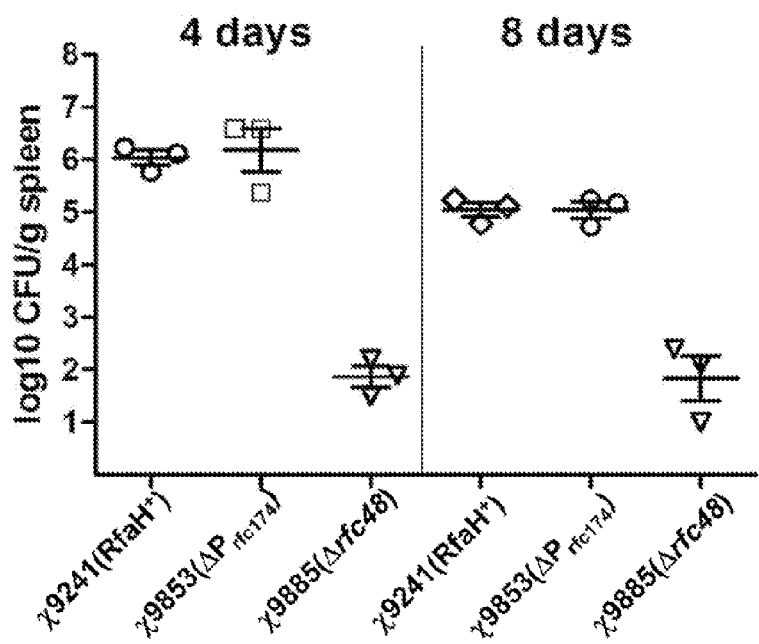
FIG. 10. Colonization of mouse spleens and livers by attenuated S. Typhimurium strains harboring plasmid pYA4088 growing in LB broth containing 0.1% arabinose. Shown is spleen (A) and liver (B) colonization by the indicated strains in BALB/c mice at 4 and 8 days post-inoculation. The horizontal lines represent the means and the error bars represent standard errors of the means.
Figure 10:
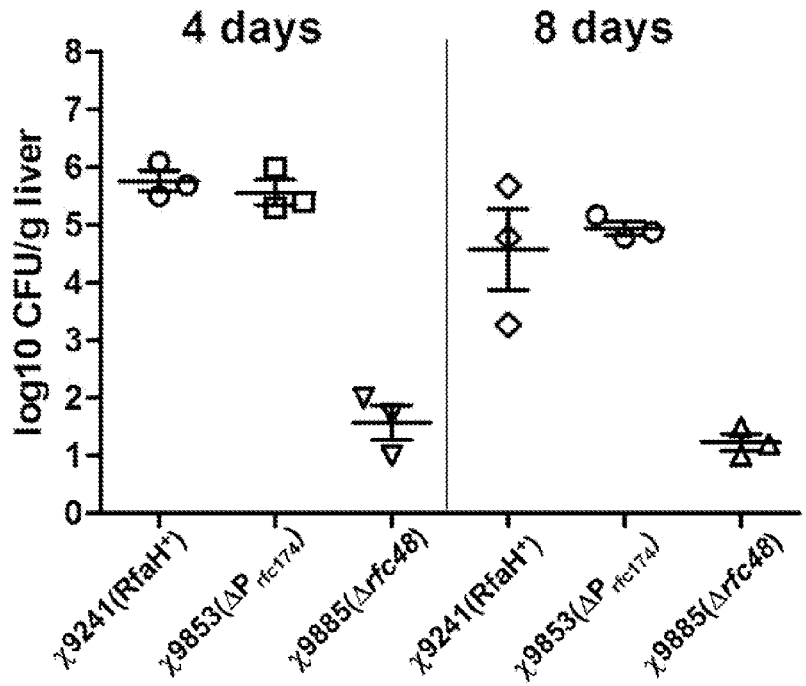

The observation that the $\Delta P_{rfc174}$::TT araC $P_{BAD}$ rfc were avirulent when given orally yet were capable of immunizing mice against a later χ3761 challenge suggests that the strains retained a limited ability to colonize either or both the intestinal or systemic immune tissues of the mice. To confirm that these mutations in χ9241 background still retained the ability to colonize systemic immune tissues of the mice, groups of mice were orally inoculated with $1.0 \times 0^9$ cells of various strains harboring pYA408, and bacterial colonization of spleen and liver was enumerated at 4 and 8 days post inoculation (FIG. 10).

The χ9241(pYA4088) and χ9853(pYA4088) ($\Delta P_{rfc174}$::TT araC $P_{BAD}$ rfc) colonized the spleen and liver, and reached to high numbers in both tissues, with a slight colonization reduction at eight days. However χ9885(pYA4088) (Δrfc-48) colonized the spleen and liver in low numbers, and this number did not increase after 8 days. There is a significant difference for bacterial load in spleen and liver between χ9885(pYA4088) (Δrfc-48) and χ9853(pYA4088) ($\Delta P_{rfc174}$::TT araC $P_{BAD}$ rfc) at 4 days and 8 days after inoculation (P<0.0001). There was a slight reduction in tissue colonization by χ9853(pYA4088) compared to its parent strain χ9241 (pYA4088), but the difference was not statistically significant (P>0.05).

Effect of rfc Mutations on Immunogenicity and Protective Efficacy of RASV Strains.

Figure 11:
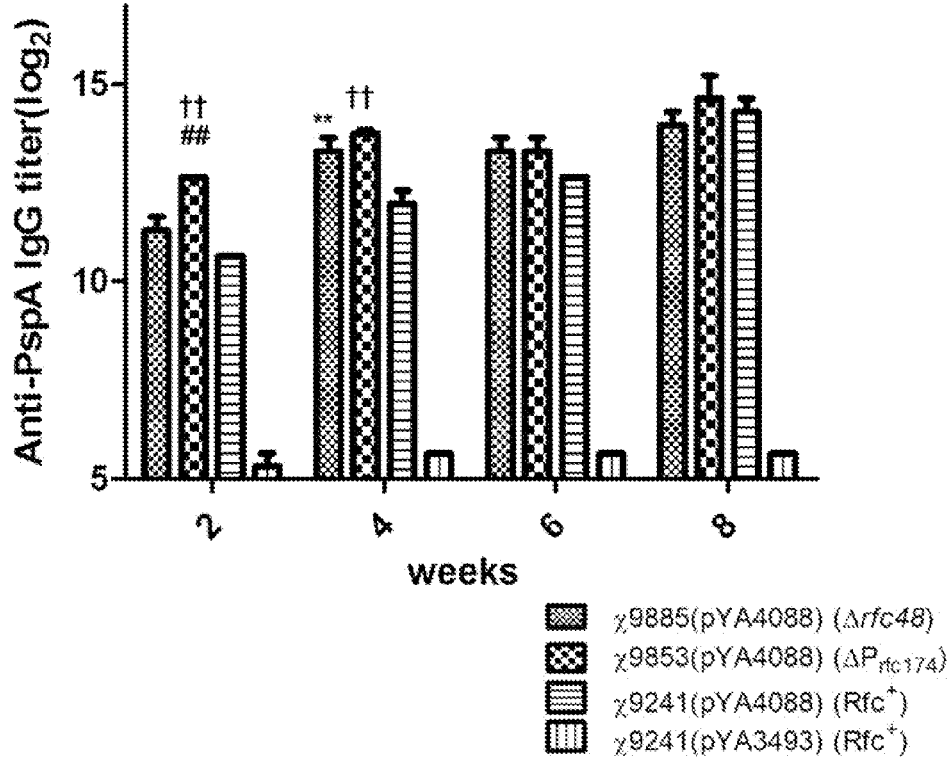
FIG. 11. Serum IgG responses in immunized and control mice. Total serum IgG specific for rPspA (A), S. Typhimurium LPS (B), and SOMPs (C) were measured by ELISA. The data represent reciprocal anti-IgG antibody levels in pooled sera from mice orally immunized with attenuated Salmonella carrying either pYA4088 (pspA) or pYA3493 (control) at the indicated number of weeks after immunization. The error bars represent variations between triplicate wells. The mice were boosted at week 4. **: χ9885 (pYA4088) vs. χ9241 (pYA4088) P<0.001; #: χ9885(pYA4088) vs χ9853 (YA4088) P<0.01; ##: χ9885(pYA4088) vs. χ9853 (pYA4088) P<0.001; ††: χ9853(pYA4088) vs. χ9241 (pYA4088) P<0.001; †: χ9853(pYA4088) vs. χ9241 (pYA4088) P<0.01.
Figure 11:
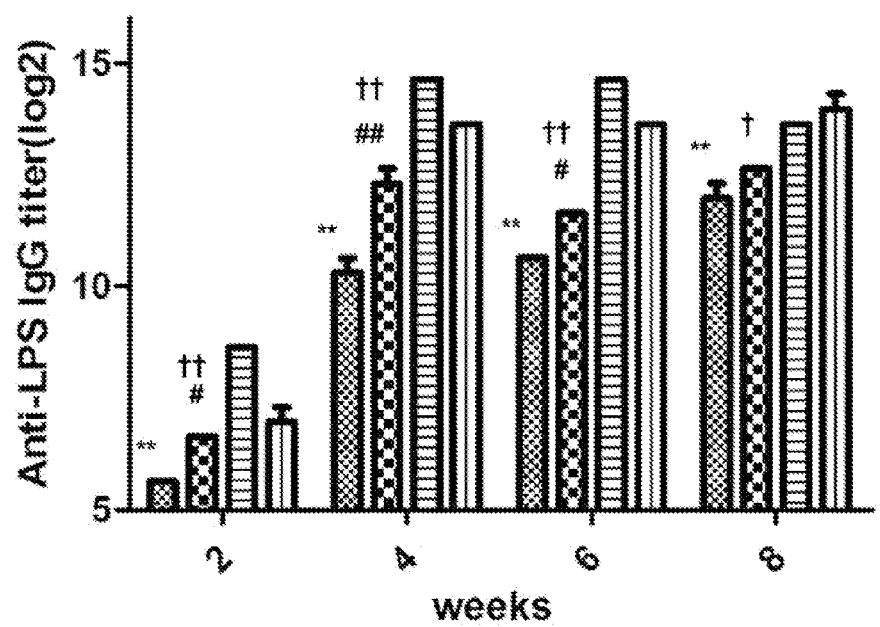
Figure 11C:
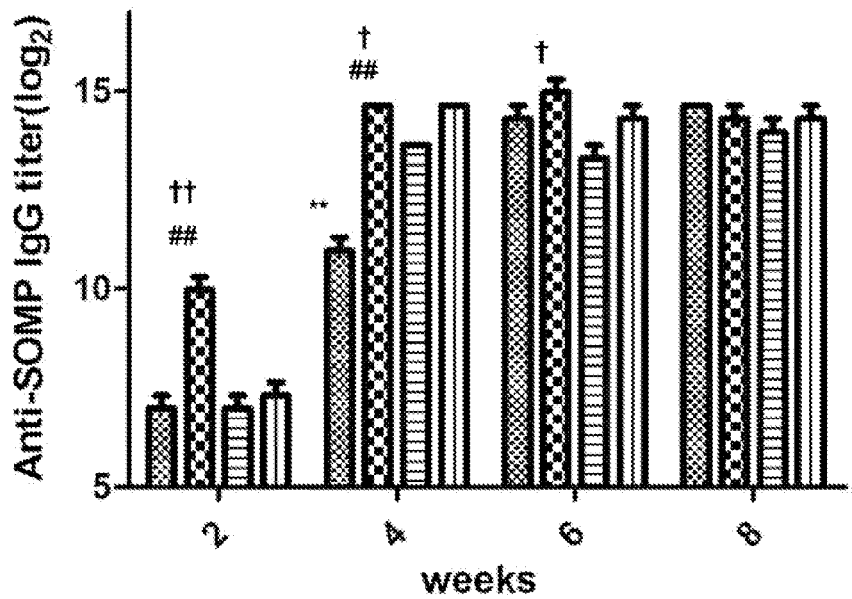

Mice were inoculated orally ($1.0 \times 10^9$ CFU) with four mutant strains harboring either pYA4088 or the empty vector pYA3493. Mice were boosted with a similar dose of the same strain 4 weeks later. The antibody responses to rPspA, *Salmonella* LPS and SOMP in the sera of immunized mice were measured according to material and methods (FIG. 11). This experiment was performed twice, 5 mice per group were involved in the first experiment, and 7-11 mice per group were used in the second experiment. The results from both experiments were similar and have been pooled for analysis.

High serum IgG titers against PspA (FIG. 11A) were observed 2 weeks after the primary immunization in mice inoculated with χ9241 (pYA4088), χ9885(pYA4088) and χ9853(pYA4088) however, there is a significant difference between the serum IgG titers from the mice immunized by χ9241 and χ9853(P<0.001). Anti-LPS titers were low, but detectable at 2 weeks, and reached a maximum by 8 weeks (FIG. 11B). Anti-LPS titers from mice immunized by χ9885 (pYA4088) and χ9853(pYA4088) were significantly lower than those of mice immunized by χ9241(pYA4088 or pYA3493) during all time points measured (P<0.01).

By week 4, the serum anti-rPspA IgG antibody levels of mice immunized with χ9885(pYA4088) was significantly higher than mice immunized with χ9241(pYA4088) (P<0.001), and was higher than mice immunized with χ9853 (pYA4088), but not significantly different. The anti-LPS IgG antibody levels in χ9853(pYA4088) immunized mice were significantly lower than mice immunized with χ9241 (pYA4088). No anti-PspA IgG was detected in mice immunized with strain χ9241(pYA3493).

After the second immunization at week 4, no significant boosting of serum antibody responses to either PspA or LPS was observed for mice immunized with χ9241(pYA4088) or the $\Delta P_{rfc174}$::TT araC $P_{BAD}$ rfc strain χ9853(pYA4088), but significant boosting of serum antibody responses to PspA was observed for mice immunized with the Δrfc-48 strain χ9885 (pYA4088), and boosting of anti-LPS IgG also was observed. The serum immune responses peaked at 6 weeks with no changes observed at week 8.

IgG Isotype Analyses.

Figure 12A:
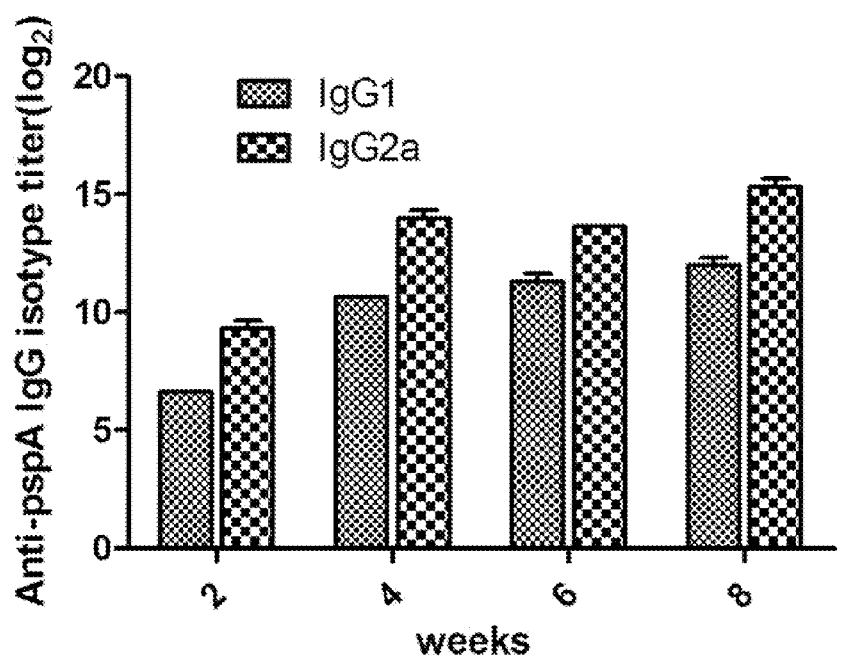
FIG. 12. Serum IgG1 and IgG2a responses to rPspA. The data represent ELISA results determining the level of IgG1 and IgG2a subclass antibody to rPspA in the sera of BALB/c mice orally immunized with (A) χ9853(pYA4088)($\Delta P_{rfc174}$), (B) χ9885(pYA4088)(Δrfc48), or (C) χ9241(pYA4088) (Rfc+) the indicated number of weeks after immunization. The error bars represent the standard deviations FIG. 13. Oral immunization with PspA-expressing Salmonella strains protects BALB/c mice against i.p. challenge with S. pneumoniae WU2, 9(control) or 11-13(vaccine) mice per group were orally immunized twice at 4-weeks intervals with the indicated vaccine strains. Mice were challenged with $4 \times 10^4$ CFU of S. pneumoniae WU2 (200 times $LD_{50}$) 4 weeks after the second oral immunization. Mortality was monitored for 2 weeks after pneumococcal challenge. Differences between groups were determined using Chi square test and the log-rank test. All vaccine groups were significantly different from the χ9241(pYA3493) control (P<0.002) by two methods. Chi square test: χ9885(pYA4088) vs. χ9853 (pYA4088), P=0.1219; χ9885(pYA4088) vs. χ9241 (pYA4088), P<0.0001; χ9853(pYA4088) vs. χ9241 (pYA4088), P=0.005. The log-rank test: no significant difference between vaccine strains (pYA4088).
Figure 12:
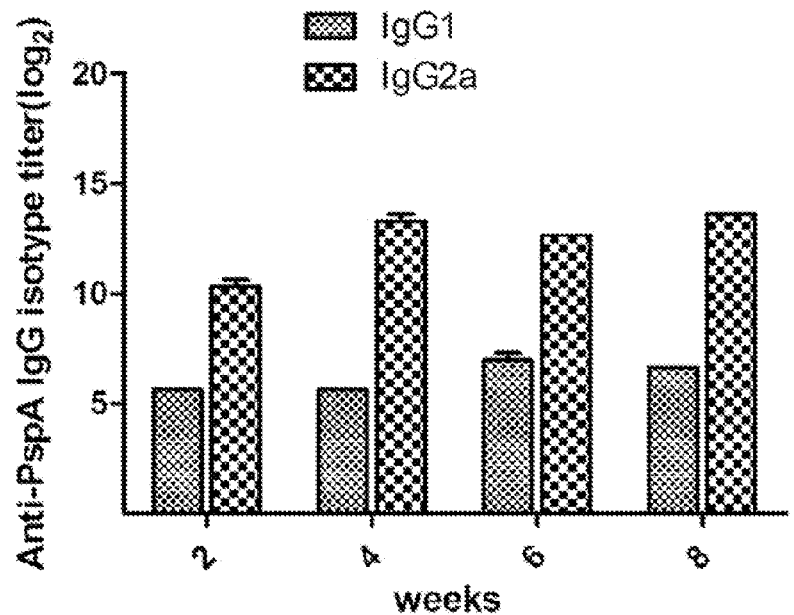
Figure 12:
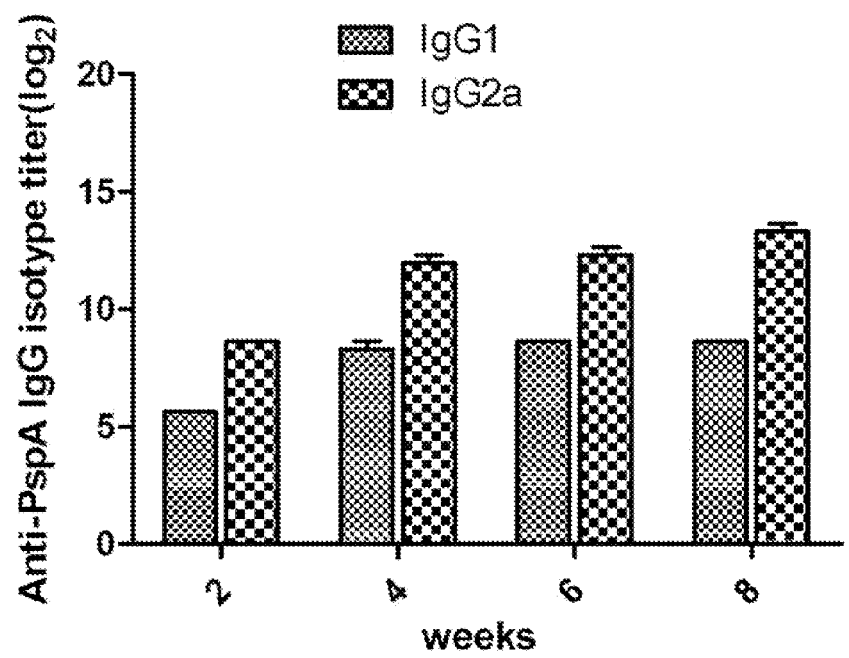

The serum immune responses to rPspA were further examined by measuring the levels of IgG isotype subclasses IgG1 and IgG2a. Th1 and Th2 mixed-type immune responses are typically observed after immunization with attenuated *Salmonella* strains. The IgG2a levels were always higher than IgG1 levels during each time period checked and the levels of anti-rPspA and IgG1 and IgG2a isotypes antibodies gradually increased (FIG. 12). The ratio of IgG2a to IgG1 was 16:1 for χ9885(pYA4088)-immunized mice and 2-4:1 for χ9241 (pYA4088) or χ9853 (pYA4088)-immunized mice.

Status of Systemic Cytokine Environment.

The colonization data show (FIG. 9) that after 8 days inoculation, the number of bacteria decreases; at that point cytokines production probably is highest. One week after the primary immunization, sera from each group of mice were subjected to Bio-Plex analysis to measure the overall levels of cytokine secretion. The cytokine secretion profiles are summarized in Table 5. Sera from all immunized mice showed increased levels of cytokine concentrations compared with the BSG immunized group except IL-10 of sera from mice immunized by χ9853. The concentrations of both Th1 cytokines (IL-2, TNF-α, IFN-γ, IL-12) and Th2 cytokines (IL-4, IL-5, IL-10, IL-13) are increased in χ9885(pYA4088) group compared to the χ9241(pYA4088) group. But the concentrations of both Th1 and Th2 cytokines have decreased or the same level in the χ9853(pYA4088) compared with that in χ9241 (pYA4088) group except IL-2.

Evaluation of Protective Immunity.

To examine the ability of RASV-rPspA vaccines to protect against pneumococcal infection, mice were challenged i.p. with $4.0 \times 10^4$ CFU (200 $LD_{50}$) of *S. pneumoniae* WU2 4 weeks after they were boosted. The three groups received either a vaccine strain harboring pYA4088 expressing PspA$_{RX1}$, which is cross-reactive with PspA produced by *S. pneumoniae* WU2 (FIG. 13) while control group received χ9241 containing pYA3493(empty vector). Immunization with any of the pspA-expressing strains provided significant protection against challenge (P<0.002) compared with control χ9241 containing pYA3493(empty vector). However, the protection afforded by χ9885(pYA4088) and χ9853 (pYA4088) was significantly higher than χ9241 (pYA4088) (P≤0.005). But there is no significant difference in the protection rate between χ9885 and χ9853. All of the mice that died in these experiments succumbed within 4 days of the challenge.

Increased Immunogenicity of Conserved Antigens Against Different Enteric Bacteria.

Figure 14:
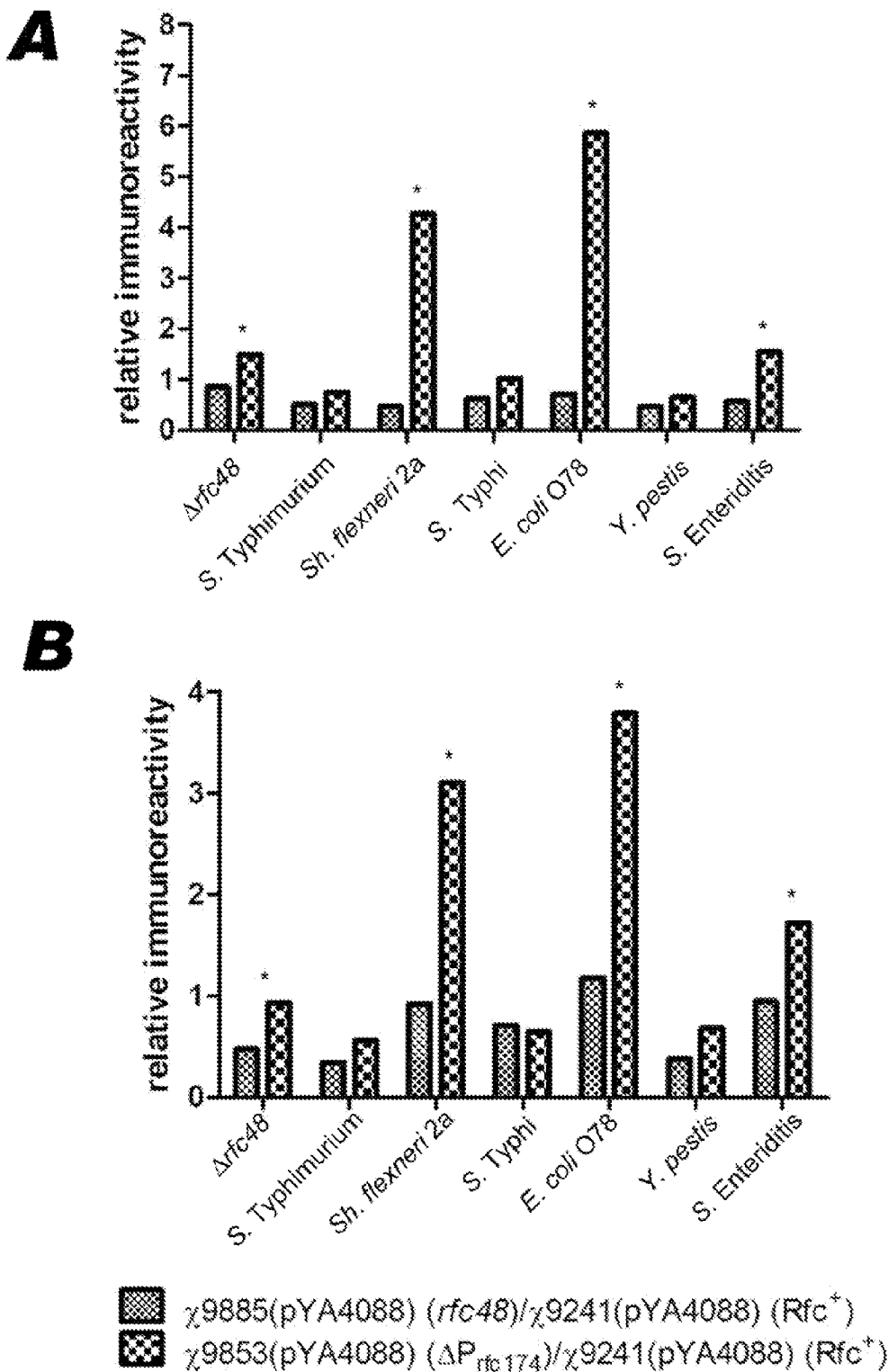
FIG. 14. Relative reactivities of immune sera, measured 6 weeks after the primary immunization, to homologous and heterologous bacteria from mice immunized with χ9241 (pYA4088) and its mutant derivatives. Pooled immune sera from mice immunized with χ9885(pYA4088) (Δrfc48), χ9853(pYA4088) ($\Delta P_{rfc174}$), and χ9241(pYA4088) (parent vaccine strain) were tested against whole cells (A) or purified outer membrane proteins (B) from different enteric bacteria by indirect ELISA. The reactivity is expressed relative to that of χ9241(pYA4088) immune serum at the same dilution. Means of values from three independent experiments are shown. * means the χ9853(pYA4088) groups were significantly different from the χ9885(pYA4088) groups (P<0.05). The strains are (left to right) Δrfc48 χ9944, S. Typhimurium χ3761, S. flexneri 2a wild type 2457T, S. Typhi ISP1820 χ7122, E. coli O78, Y. pestis KIM6+, and S. Enteriditis χ3550 (group D1).

We examined the cross-reactive antibodies elicited by the Δrfc48 vaccine strain χ9885(pYA4088), by the rfc arabinose regulated strain χ9853(pYA4088) and by the Rfc$^+$ strain χ9241 (pYA4088). The reactivity of pooled immune sera (11-16 mice per group) taken two weeks after boosting from groups of mice inoculated in the previous experiment was evaluated by ELISA against a panel of homologous and heterologous wild-type strains as well as their outer membrane proteins (FIG. 14). In each case, immunization with the arabinose regulated rfc strain χ9853(pYA4088) generated higher titers against both whole cells and OMPs isolated from a diverse group of Gram negative organisms, including *S. Typhimurium* and Enteriditis, *Shigella flexneri*, *E. coli*, and *Yersinia pestis* than the Δrfc-48 strain χ9885. The Δrfc-48 strain χ9885(pYA4088) also generated higher titers against OMPs isolated from BS64 (*Shigella flexneri* 2a wild-type 2457T), χ7122 (*Escherichia coli* O78), χ3550 (*S. Enteriditis* (Group D1)) than χ9241(pYA4088).

Discussion

The biggest challenge in the development of live *Salmonella* vaccines is to maintain a balance between safety and immunogenicity (12, 28). After oral or intranasal immunization, a RASV must be able to withstand acidic, osmotic, and enzymatic stresses as well as surviving the host defenses of bile, antimicrobial peptides, and innate immunity. The ideal RASV strain will be capable of tolerating the aforementioned stressors while remaining avirulent and capable of eliciting a robust immune response. LPS, especially O-antigen, confer *Salmonella* resistance to the environmental stresses and virulence. Strains with mutations that eliminate LPS O-antigen might be less immunogenic due to their failure to colonize the intestinal tract and invade intestinal mucosal cells (60, 61). It is advantageous for the vaccine strains to regulate the O-antigen synthesis in vitro, and shut off O-antigen in vivo after colonization of host lymphoid tissues (12).

In this work, we applied the regulated delayed attenuation approach to produce strains with arabinose-regulated synthesis of Rfc, O-antigen polymerase required for production of full-length O-antigen. We compared arabinose-regulated rfc expression strains to a Δrfc strain and wild-type strain in vitro assays. As previously seen in other arabinose controlled expression systems (26), the SD sequence and start codon will greatly affect the tight control expression of rfc under the araC $P_{BAD}$ promoter. In the case of arabinose-regulated rfc expression, based on the LPS profile silver staining and western blots analysis using *Salmonella* anti-LPS sera, only $\Delta P_{rfc174}$ were unable to produce O-antigen in the absence of arabinose, and able to produce the full-length O-antigen in the present of arabinose (FIG. 8). $\Delta P_{rfc173}$ showed some leaky expression of rfc, leading to synthesis of part O-antigen without arabinose, and $\Delta P_{rfc175}$ showed some tight control of rfc expression (FIG. 8). When grown without arabinose, the tightly regulated delayed rfc strain $\Delta P_{rfc174}$ and $\Delta P_{rfc175}$ still produced part full-length O-antigen detectable by P22 transduction assays, although they were undetectable by silver staining and western blots (FIG. 8 and Table 4), however the amount of P22 transductants was reduced compared to that produced by the same strain grown with arabinose or by strains expressing wild-type rfc. As mentioned above, an ideal *Salmonella* vaccine strain should exhibit wild-type abilities to withstand stresses and host defenses encountered after oral or intranasal immunization while remaining avirulent. When the $\Delta P_{rfc174}$ mutant was grown in the presence of arabinose, its phenotype was similar to that of its wild-type parent χ3761 (FIGS. 8 and 10 and Table 4) even though $\Delta P_{rfc174}$ mutant was totally attenuated ($LD_{50} > 10^9$) in the presence of arabinose (Table 4). In the absence of arabinose, this mutant was more susceptible to deoxycholate and polymyxin B than wild type parent χ3761. In our previous report that the colonization in lymphoid tissues is very important for inducing long and higher immune response against heterologous or itself antigens (26), we determined the colonization of vaccine strains in χ9241 background (pYA4088), which is widely used in our lab to evaluate other mutations. When the spleen and livers of the mice were examined 4 and 8 days post-inoculation, the numbers of the delayed attenuated mutant χ9853 (pYA4088) and parent strain χ9241(pYA4088) were similar while the number of χ9885(pYA4088) was significantly lower. These data are similar to the literature reported previously, showing that Δrfc-48 mutant is a poor colonizer, but it still colonized the lymphoid tissues at 10 to 1000 CFU/g (FIG. 10) (11). Our unpublished data showed that outer core of LPS greatly affect the colonization in systemic organ (spleen and liver), which will greatly affect immune response against heterologous antigens.

The Asd$^+$ recombinant plasmid pYA4088, which encodes a recombinant pspA gene fused to DNA encoding the β-lactamase signal sequence, was introduced into the new strains. The $P_{trc}$ promoter drives expression of pspA and the bla signal sequence directs periplasmic secretion of PspA. Strain χ9241 carries the ΔrelA198::araC $P_{BAD}$ lacI TT deletion/insertion. When this strain is grown in the presence of arabinose, lacI is expressed. The LacI protein binds to the $P_{trc}$ promoter on pYA4088, preventing pspA expression. Once the strain invades and colonizes host tissues, where arabinose is not available, LacI is no longer synthesized and pspA is expressed (FIG. 9). Further, we checked adaptive immunity induced by χ9853 ($\Delta P_{rfc174}$), χ9885 (Δrfc-48) and their parent strain χ9241 containing pYA4088. Level of IgG against PspA were significantly higher in mice immunized with either delayed attenuation mutant χ9853 ($\Delta P_{rfc174}$) or deletion mutant χ9885 (Δrfc) compared with parent χ9241 during the first month following immunization (FIG. 11A). After the boost at day 28, the levels of all the strains were similar. The level of IgG against *Salmonella* LPS were significantly lower in mice immunized with either χ9853 ($\Delta P_{rfc174}$) or χ9885 (Δrfc) than that induced by parent strain χ9241 (Rfc$^+$) during all time points measured. A mixed Th1/Th2 IgG isotype is desirable in pneumococcal vaccines. This development has been shown to prevent carriage of *S. pneumonia* in the lungs and ear mucosa, hence protecting against pneumonia and otitis media (70). χ9853 ($\Delta P_{rfc174}$), χ9885 (Δrfc-48) and parent χ9241 induced a similar level of IgG2a in a mixed Th1/Th2 IgG isotype, but χ9853 ($\Delta P_{rfc174}$) induced much higher IgG1 isotype than χ9885 (Δrfc-48) and χ9241 (FIG. 12).

Cytokines play important roles in the development, function and control of the cells differentiation of T-cell, B-cell and antigen presenting cell such as macrophage and dendritic cell, which contribute to cleaning the *Salmonella* from mice and switching innate immunity to adaptive immunity (8, 32, 37). All the immunized mice produced significant higher levels of cytokine concentrations (Th1-like cytokines and Th2-like cytokines) compared with the BSG immunized group (Table 5). It is interesting that χ9885 (Δrfc-48) induced higher cytokines than other two vaccine strains, but it did not induce higher antibodies titer than χ9241 and χ9853, however χ9853 induce less Th2-like cytokines (IL-4, IL-5, IL-10, IL-13) production than χ9241 and χ9885, but χ9853 elicited a higher Th2 immune response (IgG1 isotype) (Table 5 and FIG. 12). Our data indicated that the cytokines bridge innate immunity and adaptive immunity, but much cytokines did not contribute to inducing more adaptive immunity, but probably contribute to protection against challenge by pathogens (FIG. 13), because the cytokines are essential to the establishment and maintenance of immunological memory (8), T-cell-dependent response which play roles in protection against virulence *S. pneumonia* challenge (33). The cytokine concentrations of BSG group are different from other report, especially, the TNF-a and IL-12 in our assay are much higher than that other researcher got (29).

Figure 13:
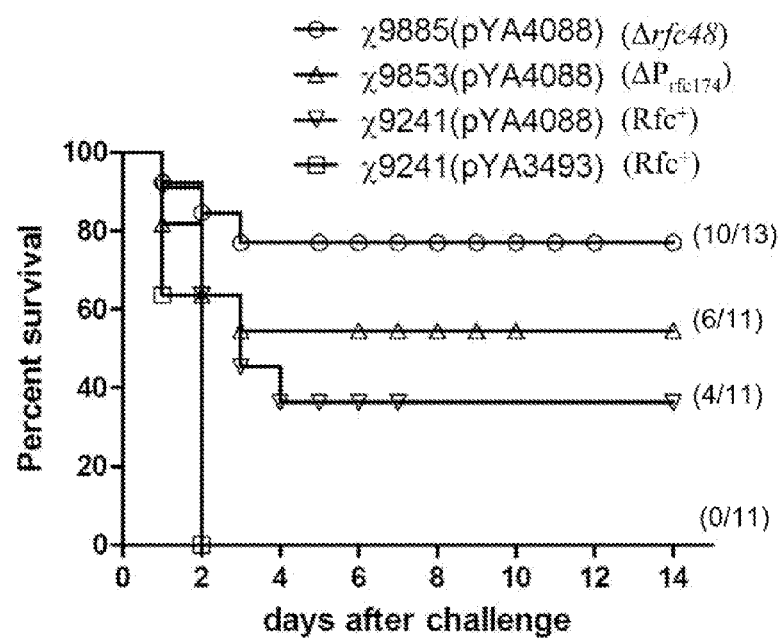

When challenged i.p. with virulent *S. pneumonia*, all groups immunized with strains expressing pspA were protected (FIG. 13). The strains χ9853(pYA4088) and χ9885 (pYA4088) provided significantly greater protection than immunization with parent strain χ9241(pYA4088). It is interesting that χ9885(pYA4088) provided higher protection than χ9853(pYA4088) even though they don't have significant difference. The most probability is that χ9885(pYA4088) can colonize the lymphoid tissues (spleen and liver), and last a long time (at least 8 days) (FIG. 10), and χ9885(pYA4088) can induce the higher cytokines than χ9853 and χ9241 (pYA4088) (Table 5), and χ9885(pYA4088) induced the same level IgG1 and IgG2a isotypes as χ9241(pYA4088) (FIGS. 11 and 12). It has been suggested in the literature that down-regulation of immune-dominant antigens will enhance the immunogenicity of conserved antigens (26, 42). This might allow us to produce *Salmonella* vaccine strains capable of providing broad protection against a variety of enteric pathogens. The delayed attenuation mutant χ9853 ($\Delta P_{rfc174}$) reacted much more vigorously against *Shigella flexneri*, *E. coli* and *S. Enteriditis* bacteria and OMPS, and slightly more against *S. Typhimurium* and *Yersinia. pestis* than χ9885 (Δrfc-48). In our laboratory, we have developed three mutations (ΔgalE, Δpmi, and $\Delta P_{rfaH178}$) to eliminate the immune-dominant antigen of RASV (24, 26, 49, 59), The inclusion of these three mutations and $\Delta P_{rfc174}$ in vaccine strains should minimize induction of immune responses to the B group-specific O-antigen and maximize induction of antibodies to the conserved LPS core antigen and heterologous antigens from other pathogens. This expectation will be investigated in a future study.

In summary, we have shown that $\Delta P_{rfc174}$ mutations can be combined with other attenuating mutations to produce a RASV capable of delivering a heterologous antigen to induce protective immunity. While all three strains producing PspA were capable of protecting mice against *S. pneumoniae* challenge, the delayed regulated mutant χ9853 (ΔP$_{rfc174}$), in combination with ΔpabA ΔpabB mutations was superior to a ΔpabA ΔpabB Δrfc strain in colonizing lymphoid tissues, eliciting serum antibodies to a heterologous antigen after immunization, and inducing antibodies that were cross-reactive with other enteric pathogens.

Example 3

Regulated O Antigen Expression in Human Host-Restricted Serovars *Salmonella enterica* Serovar *Typhi* and *Salmonella enterica* Serovar *Paratyphi* A

Figure 15:
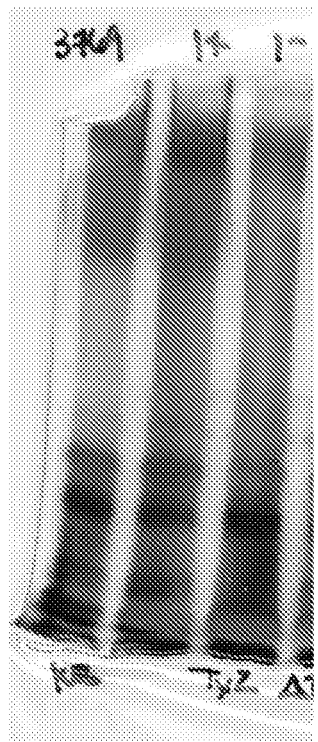
FIG. 15. Arabinose regulation of rfc in S. Typhi. Lipopolysaccharide (LPS) phenotypes of wild-type S. Typhi strains χ3769 and ISP1820 and the indicated derivatives. LPS from different strains grown in nutrient broth with/without 0.2% arabinose (A and B) were silver stained after separation by 12% SDS-PAGE.
Figure 15:
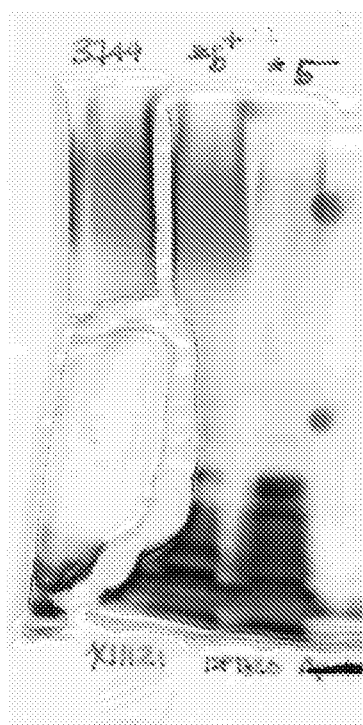
Figure 16:
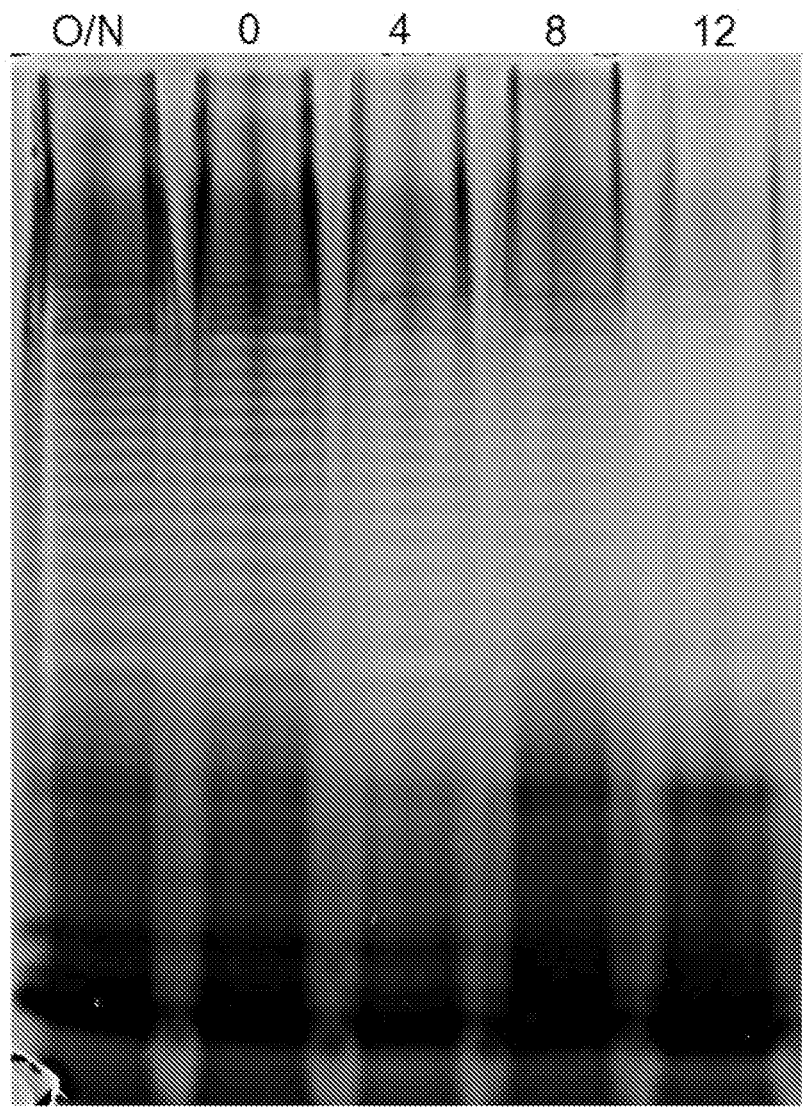
FIG. 16. Loss of O antigen in the absence of arabinose in regulated rfc S. Typhi strain χ11120. S. Typhi strain χ11120 was grown in nutrient broth with 0.1% arabinose overnight at 37° C. Cells were then washed 3× in BSG (buffered saline with gelatin) and grown in nutrient broth with no arabinose for 12 generations. Logarithmic growth was maintained by 2-fold dilution in NB each time the culture $OD_{600}$ reached 0.6. Gel samples were normalized to the total amount of protein/ml. O/N, the overnight culture grown in NB with arabinose. The numbers above each lane indicates the number of generations the cells had grown in the absence of arabinose.

*S. Typhi* is frequently used for construction of vaccines for human use. We introduced the ΔP$_{rfc174}$::TT araC P$_{BAD}$ rfc mutation into *S. Typhi* strains Ty2 and ISP1820 to yield strains χ11120 and χ11121. The mutant strains exhibit arabinose-dependent O antigen synthesis (FIG. 15), indicating that this mutation functions in *S. Typhi*. When χ11120 was grown in nutrient broth containing arabinose and then transferred to nutrient broth without arabinose, O antigen was lost gradually over time, with nearly complete loss of O antigen by 12 generations (FIG. 16).

Figure 17:
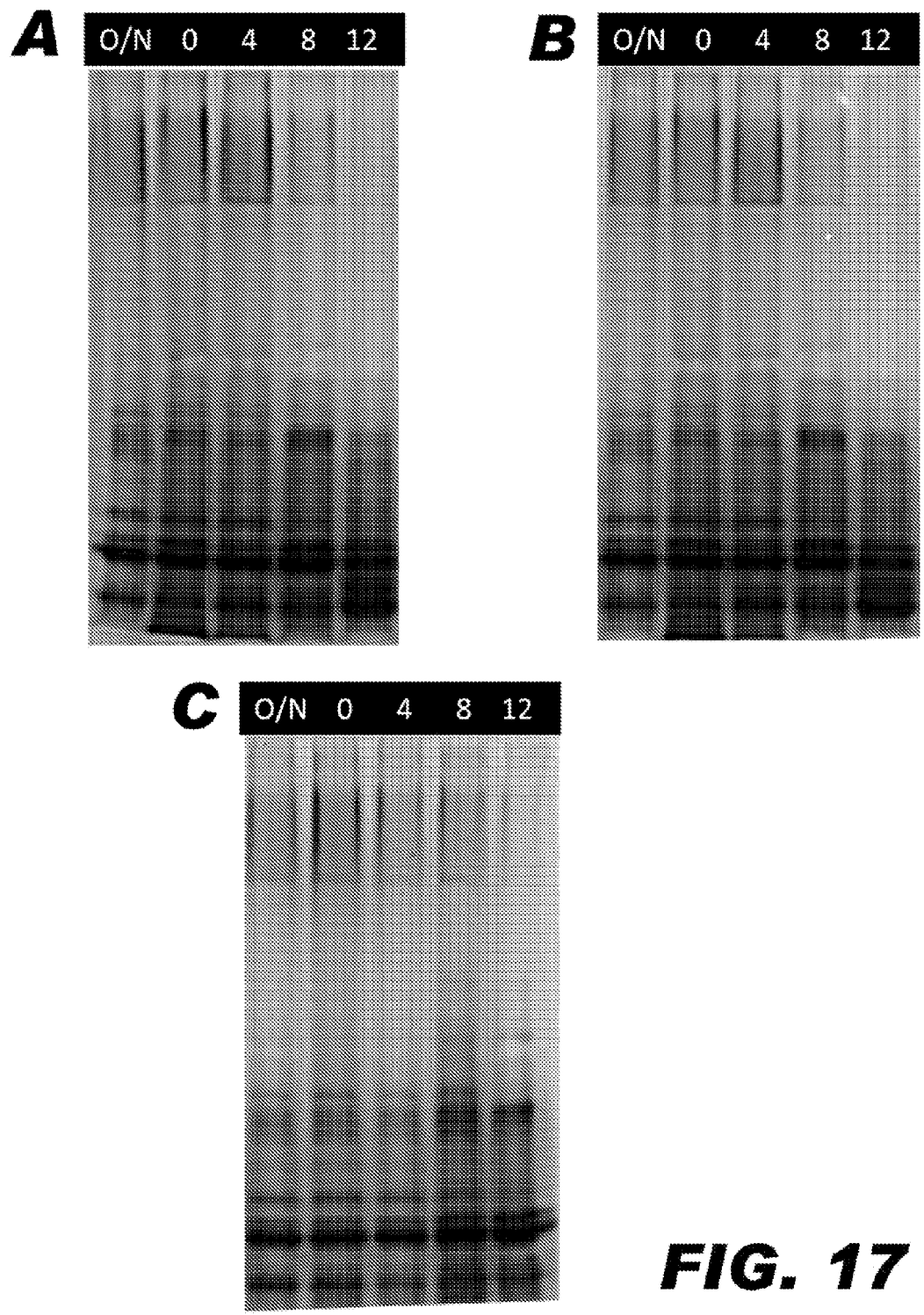
FIG. 17. Arabinose and mannose regulation of O antigen synthesis in S. Typhi strains carrying both regulated rfc and Δpmi mutations. S. Typhi χ11170 (Δpmi-2426 $\Delta P_{rfc174}$::TT araC $P_{BAD}$ rfc) was grown in NB with 0.1% mannose and 0.1% arabinose overnight at 37° C. Strains were then washed 3× in BSG and grown in NB with no sugar, 0.1% mannose only or 0.1% arabinose only for 12 generations. Logarithmic growth was maintained by 2-fold dilution in NB each time the culture $OD_{600}$ reached 0.6. Gel samples were normalized to the total amount of protein/ml. O/N, overnight culture grown in the presence of both sugars. The numbers above each lane indicates the number of generations the cells had grown under the indicated medium.

Another embodiment of this invention is to utilize arabinose-regulated O antigen synthesis in conjunction with another mutation that results in regulation of O antigen synthesis that is dependent upon a different sugar. We constructed *S. Typhi* strain χ11170 that carries the Δpmi-2426 ΔP$_{rfc174}$::TT araC P$_{BAD}$ rfc mutations. Thus, O antigen synthesis depends upon the presence of both mannose and arabinose. Strain χ11170 was grown in nutrient broth containing mannose and arabinose. The culture was then diluted into nutrient broth containing no sugar, mannose only or arabinose only and grown for 12 generations. O antigen was gradually lost over time under all three conditions (FIG. 17). This result demonstrates that both sugars are required for complete O antigen synthesis.

Figure 18:
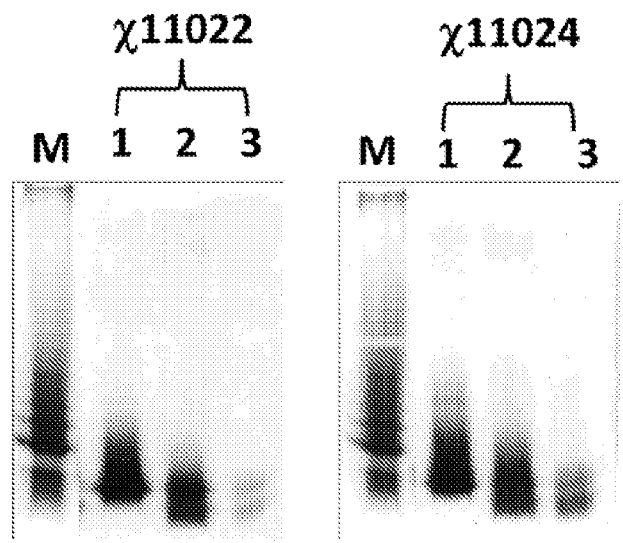
FIG. 18. Arabinose regulation of rfc in S. Paratyphi A. Lipopolysaccharide (LPS) phenotypes of wild-type S. Typhimurium UK-1 χ3761 and the indicated isogenic derivatives. LPS from different mutant strains grown in Nutrient Broth with/without 0.1% arabinose were silver stained after separation by 12% SDS-PAGE.

The ΔP$_{rfc174}$::TT araC P$_{BAD}$ rfc mutation was introduced into attenuated *S. Paratyphi* A strains derived from wild-type strain χ8387 that carry a number of attenuating mutations, including Δpmi-2426. The strains, χ11022 and χ11024, were grown overnight in Purple broth containing either arabinose, mannose or both sugars. Analysis of the LPS from these cultures shows that both sugars are required for complete O antigen synthesis (FIG. 18).

Example 4

Regulated O Antigen Expression in Avian Host-Restricted Serovar *Salmonella enterica* Serovar *Gallinarum*

Figure 19:
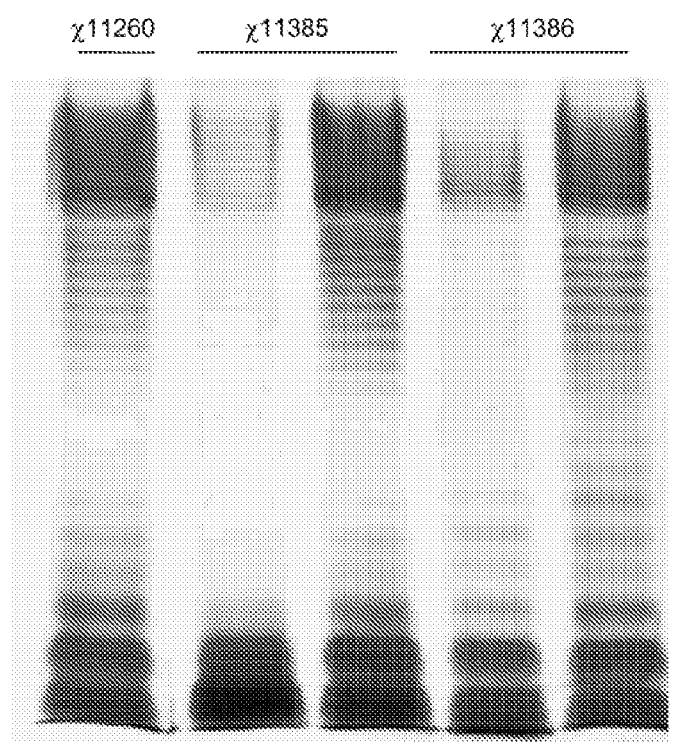
FIG. 19. Arabinose regulation of 0 antigen synthesis in S. Gallinarum strains carrying regulated rfaH or rfc mutations. LPS phenotypes of wild-type S. Gallinarum strain χ11260 and the indicated isogenic derivatives. Cells were grown overnight in Purple broth with/without 0.05% arabinose.

*S. Gallinarum* is a poultry pathogen that causes fowl typhoid (74). We constructed strains χ11385 (ΔP$_{rfc174}$::TT araC P$_{BAD}$ rfc) and χ11386 (ΔP$_{rfaH178}$TT araC P$_{BAD}$ rfaH). These strains were grown overnight in Purple broth with/without arabinose. Analysis of the LPS from these cultures demonstrates that both strains exhibit arabinose-dependent O synthesis (FIG. 19).

TABLE 1

Strains and plasmids used in this work

| Strain or plasmid | Description | Source or reference |
|---|---|---|
| *S. Typhimurium* | | |
| χ3761 | Wild type, UK-1 | (16) |
| χ9430 | χ3761 ΔpagL7::pYA4284 | Lab stock |
| χ9241 | ΔpabA1516 ΔpabB232 ΔasdA16 ΔaraBAD23 ΔrelA198::araC P$_{BAD}$ lacI TT | (51) |
| χ9660 | ΔP$_{rfaH176}$TT araC P$_{BAD}$ rfaH TT | χ3761 |
| χ9734 | ΔP$_{rfaH177}$TT araC P$_{BAD}$ rfaH TT | χ3761 |
| χ9735 | ΔP$_{rfaH178}$TT araC P$_{BAD}$ rfaH TT | χ3761 |
| χ9945 | ΔrfaH49 | χ3761 |
| χ9659 | ΔP$_{rfc173}$TT araC P$_{BAD}$ rfc | This study |
| χ9736 | ΔP$_{rfc174}$TT araC P$_{BAD}$ rfc | This study |
| χ9737 | ΔP$_{rfc175}$TT araC P$_{BAD}$ rfc | This study |
| χ9944 | Δrfc48 | This study |
| χ9884 | ΔrfaH49 | χ9241 |
| χ9852 | ΔP$_{rfaH178}$TT araC P$_{BAD}$ rfaH TT | χ9241 |
| χ9885 | ΔpabA1516 ΔpabB232 ΔasdA16 ΔaraBAD23 ΔrelA198::araC P$_{BAD}$ lacI TT Δrfc48 | This study |
| χ9853 | ΔpabA1516 ΔpabB232 ΔasdA16 ΔaraBAD23 ΔrelA198::araC P$_{BAD}$ lacI TT ΔP$_{rfc174}$TT araC P$_{BAD}$ rfc | This study |
| χ9761 | Δ(galE-uvrB)-1005 ΔmsbB48 ΔfliC2426 ΔpefA1225 ΔfimA2119 ΔfimH1019 ΔagfBAC811 | Lab stock |
| *S. Typhi* | | |
| χ3769 | Wild type Ty2 | (73) |
| ISP1820 | Wild type | (74) |
| χ11120 | Ty2 ΔP$_{rfc174}$::TT araC P$_{BAD}$ rfc | This study |
| χ11121 | ISP1820 ΔP$_{rfc174}$::TT araC P$_{BAD}$ rfc | This study |
| χ11170 | Ty2 Δpmi-2426 ΔP$_{rfc174}$::TT araC P$_{BAD}$ rfc | This study |
| *S. Paratyphi* A | | |
| χ8387 | Wild type *S. Paratyphi* A | Lab stock |
| χ11022 | ΔP$_{crp527}$::TT araC P$_{BAD}$ crp ΔP$_{fur81}$::TT araC P$_{BAD}$ fur Δpmi-2426 Δ(gmd-fcl)-26 ΔagfBAC811 ΔrelA198::araC P$_{BAD}$ lacI TT ΔsopB1925 ΔaraE25 Δ(araC P$_{BAD}$)-5::P22 P$_R$ araBAD ΔasdA27::TT araC P$_{BAD}$ c2 ΔP$_{rfc174}$ TT araC P$_{BAD}$ rfc | This study |

TABLE 1-continued

Strains and plasmids used in this work

| Strain or plasmid | Description | Source or reference |
|---|---|---|
| χ11024 | ΔP$_{crpS27}$::TT araC P$_{BAD}$ crp ΔP$_{fur81}$::TT araC P$_{BAD}$ fur Δpmi-2426 Δ(gmd-fcl)-26 ΔagfBAC811 ΔrelA198::araC P$_{BAD}$ lacI TT ΔsopB1925 ΔaraE25 Δ(araC P$_{BAD}$)-5::P22 P$_R$ araBAD ΔasdA27::TT araC P$_{BAD}$ c2 ΔP$_{rfc174}$ TT araC P$_{BAD}$ rfc Δ(yshA-yihW)-207 | This study |
| *S. Gallinarum* | | |
| χ11260 | Wild type *S. Gallinarum* 287/91 | (75) |
| χ11385 | ΔP$_{rfc174}$::TT araC P$_{BAD}$ rfc | χ11260 |
| χ11386 | ΔP$_{rfaH178}$TT araC P$_{BAD}$ rfaH TT | χ11260 |
| *E. coli* | | |
| χ7232 | endA1 hsdR17 (r$_K$−, m$_k$+) glnV44 thi-1 recA1 gyrA relA1 Δ(lacZYA-argF)U169 λpir deoR (φ80dlac Δ(lacZ)M15) | (34) |
| χ7213 | thi-1 thr-1 leuB6 glnV44 fhuA21 lacY1 recA1 RP4-2-Tc::Mu[λ pir] ΔasdA4 Δ(zhf-2::Tn10) | (34) |
| *S. pneumoniae* WU2 | Wild-type virulent, encapsulated type 3 | (5) |
| pYA3700 | TT araC P$_{BAD}$ cassette plasmid; Ap$^r$ | (46) |
| pRE112 | sacB mobRP4 R6K ori Cm$^R$ | (14) |
| pYA4284 | pRE112, ΔpagL7 | Lab stock |
| pYA4718 | ΔrfaH49 | pRE112 |
| pYA4721 | ΔP$_{rfaH176}$ ctcgag AGGA gtcattATG | pRE112 |
| pYA4301 | ΔP$_{rfaH177}$ ctcgag AAGA gtcattATG | pRE112 |
| pYA4304 | ΔP$_{rfaH178}$ ctcgag AAGA gtcattGTG | pRE112 |
| pYA4717 | Constructed for rfc48 deletion | This study |
| pYA4297 | Constructed for rfc173 promoter deletion and P$_{BAD}$ promoter insertion ctcgag AGGAgtcattATG | This study |
| pYA4298 | rfc174 actcgag AGGA gtcattGTG | This study |
| pYA4299 | rfc175 ctcgag GAGG gtcattGTG | This study |
| pYA3493 | Plasmid Asd$^+$; pBRori β-lactamase signal sequence-based periplasmic secretion plasmid | (20) |
| pYA4088 | 852 bp DNA encoding the α-helical region of PspA from aa 3-285 in pYA3493 | (51) |

TABLE 2

Primers used in this work

| Primer name | Sequence 5'-3' |
|---|---|
| RfaH1-FXmaI-pstI | ACTGCCTGCAGCCCGGGCTTAAACTGCGGCAGCTTGTC |
| RfaH1-RPstI | ACTGCCTGCAGCTTCATCCTTTAAGCCGTATC |
| RfaH2-FXhoI | ATGCACTCGAGAGGAGTCATTATGCAATCCTGGTATT |
| RfaH2-RkpnI | CGACGGTACCGGTTGTATTCTGAACGATCGC |
| RfaH2-1 | ATGCACTCGAGAAGAGTCATTATGCAATCCTGGTATT |
| RfaH2-2 | ATGCACTCGAGAAGAGTCATTGTGCAATCCTGGTATT |
| RfaH-1F | ACTGGGTACCCCATCGCCACGCGTTTTGGC |
| RfaH-1R | TGAACGATCGCCTGCAGGAATGACTCTTATCCGCTTG |
| RfaH-2F | AGTCATTCCTGCAGGCGATCGTTCAGAATACAACCT |
| RfaH-2R | ATCTCCCGGGTTATGCACTGCCGGGACGCG |
| T4TT-R | ATCACAATTCTAGGATAGAAT |
| Rfc1-FXmaI-PstI | ACTGCCTGCAGCCCGGGTCTTTCTGTTCTACAGAACC |
| Rfc1-RPstI | ACTGCCTGCAGAGATTCATCATGAGGTTCCC |
| Rfc2-FXhoI | ATGCACTCGAGAGGACTCTATATGCTTATAATTTC |
| Rfc2-kpnI | ACGGAGGTACCCTCTCTGAACTCCATCAACAC |
| Rfc2-1 | ATGCACTCGAGAGGACTCTATGTGCTTATAATTTC |
| Rfc2-2 | ATGCACTCGAGAGGCTCTATGTGCTTATAATTTC |
| T4TT-R | ATCACAATTCTAGGATAGAAT |
| Rfc-1F | CTGCCTGCAGAAGTATGTCGCGGCACGATG |
| Rfc-1R | ATAACTTACCTGCAGGATAGAGCCTTTAGAAAAAATG |

TABLE 2-continued

Primers used in this work

| Primer name | Sequence 5'-3' |
|---|---|
| Rfc-2F | GGCTCTATCCTGCAGGTAAGTTATACGGCGGC AATGC |
| Rfc-2R | ATCTCCCGGGGTTCGTTTAAACCTGTTTCAC |

TABLE 3

Minimum inhibitory concentrations (MIC) of antibiotic substances, swarming motility, transduction efficiency and virulence of S. Typhimurium strain χ3761 and its rfaH mutant derivatives.

| Strain | 0.1% arabinose | P22 transductants* | MIC DOC** (mg/ml) | MIC Polymyxin B (μg/ml) | Swarming motility (mm) | Oral LD$_{50}$ (CFU) |
|---|---|---|---|---|---|---|
| χ9660 ($\Delta P_{rfaH176}$) | − | 305 | 3.2 | 0.25 | 14.5 | ND$^a$ |
|  | + | 3270 | 6.25 | 0.60 | 21.3 | ND |
| χ9734 ($\Delta P_{rfaH177}$) | − | 266 | <1.6 | <0.12 | 12.2 | ND |
|  | + | 3980 | 3.2 | 1.18 | 20.2 | $1.0 \times 10^6$ |
| χ9735 ($\Delta P_{rfaH178}$) | − | 339 | 1.6 | <0.12 | 8.0 | ND |
|  | + | 4340 | 6.25 | 0.60 | 18.1 | $1.0 \times 10^6$ |
| χ9445 (ΔrfaH49) | − | 88 | <1.6 | <0.12 | 3.0 | ND |
|  | + | ND | <1.6 | <0.12 | 3.0 | $>1.0 \times 10^8$ |
| χ3761 (RfaH$^+$) | − | 3180 | 6.25 | 0.25 | 18.3 | $1.0 \times 10^4$ |
|  | + | ND* | 6.25 | 0.60 | 21.0 | ND |

*The phage lysate used for transduction was grown on a chloramphenicol-resistant strain. Transduction was performed as described in the Materials and Methods section. The results reflect the number of chloramphenicol resistant colonies obtained after transduction.
**deoxycholate,
$^a$Not determined

TABLE 4

Minimum inhibitory concentrations (MIC) of antibiotic substances, swarming motility, transduction efficiency and virulence of S. Typhimurium strain χ3761 and its rfc mutant derivatives

| Strain | 0.1% arabinose | MIC DOC** Bile (mg/ml) | MIC Polymyxin B (ug/ml) | LB with 0.3% Agar | P22 transductants* | LD$_{50}$ (CFU) |
|---|---|---|---|---|---|---|
| χ9659 ($\Delta P_{rfc173}$) | − | 2.5 | 0.245 | 1.55 | 445 ± 35 | ND$^a$ |
|  | + | 10 | 0.59 | 2.5 | 2190 ± 190 | $5.0 \times 10^5$ |
| χ9736 ($\Delta P_{rfc174}$) | − | 2.5 | 0.123 | 1.7 | 280 ± 24 | $>1.0 \times 10^9$ |
|  | + | 10 | 0.59 | 2.7 | 2285 ± 165 | $>1.0 \times 10^9$ |
| χ9737 ($\Delta P_{rfc175}$) | − | 2.5 | 0.123 | 1.7 | 90 ± 18 | ND$^a$ |
|  | + | 5 | 0.59 | 2.7 | 3910 ± 490 |  |
| χ9944 (Δrfc48) | − | 2.5 | 0.123 | 1.5 | 0 | $>1.0 \times 10^9$ |
|  | + | 2.5 | 0.123 | 2.1 | 0 | $>1.0 \times 10^9$ |
| χ3761 (rfc$^+$) | − | 10 | 0.245 | 1.8 | 3180 ± 260 | $1.0 \times 10^4$ |
|  | + | 10 | 0.59 | 2.1 |  |  |

*The phage lysate used for transduction was grown on a chloramphenicol-resistant strain. Transduction was performed as described in the Materials and Methods section. The results reflect the number of chloramphenicol resistant colonies obtained after transduction.
**deoxycholate,
$^a$Not determined

TABLE 5

Cytokines assay in sera from immunized mice at 7 days postinoculation.

| Mice group | Cytokines concentration in sera, pg/ml | | | | | | | | |
|---|---|---|---|---|---|---|---|---|---|
|  | IL-2 | IL-4 | IL-5 | IL-10 | IL-12(p40) | IL-12(p70) | IL-13 | TNF-α | IFN-γ |
| χ9885(pYA4088) | 51.95 | 4.24 | 10.01 | 31.58 | 248.98 | 17.37 | 440.94 | 848.48 | 23.79 |
| χ9853(pYA4088) | 46.97 | 3.86 | 8.3 | 20.19 | 306.73 | 23.57 | 332.39 | 668.14 | 14.85 |
| χ9241(pYA4088) | 41.94 | 3.98 | 8.3 | 27.15 | 319.56 | 14.54 | 430.16 | 673.9 | 27.72 |
| χ9241(pYA3493) | 50.11 | 4.24 | 10.13 | 26.75 | 439.14 | 15.52 | 548.05 | 619.17 | 30.97 |
| BSG | 5.22 | 1.50 | 2.54 | 5.72 | 168.35 | 1.53 | 47.88 | 202.33 | 5.72 |

The number is the mean of two assays. All the groups have significant difference compared with BSG control (P < 0.01).

REFERENCES

1. Artsimovitch, I., and R. Landick. 2002. The transcriptional regulator RfaH stimulates RNA chain synthesis after recruitment to elongation complexes by the exposed non-template DNA strand. Cell 110:801-801.
2. Atkins, H. S., M. Morton, K. F. Griffin, M. G. M. Stokes, J. P. Nataro, and R. W. Titball. 2006. Recombinant *Salmonella* vaccines for biodefence. Vaccine 24:2710-2717.
3. Bailey, M. J. A., C. Hughes, and V. Koronakis. 1997. RfaH and the ops element, components of a novel system controlling bacterial transcription elongation. Mol. Microbiol. 26:845-851.
4. Bertani, G. 1951. Studies on lysogenesis I.: The mode of phage liberation by lysogenic *Escherichia coli*. J. Bacteriol. 62:293-300.
5. Briles, D. E., J. D. King, M. A. Gray, L. S. McDaniel, E. Swiatlo, and K. A. Benton. 1996. PspA, a protection-eliciting pneumococcal protein: Immunogenicity of isolated native PspA in mice. Vaccine 14:858-867.
6. Brown, J. S., T. Hussell, S. M. Gilliland, D. W. Holden, J. C. Paton, M. R. Ehrenstein, M. J. Walport, and M. Botto. 2002. The classical pathway is the dominant complement pathway required for innate immunity to *Streptococcus pneumoniae* infection in mice. Proc. Natl. Acad. Sci. U.S.A. 99:16969-16974.
7. Cardenas, L., and J. D. Clements. 1992. Oral immunization using live attenuated *Salmonella* spp as carriers of foreign antigens. Clin. Microbiol. Rev. 5:328-342.
8. Chabalgoity, J. A., A. Baz, A. Rial, and S. Grille. 2007. The relevance of cytokines for development of protective immunity and rational design of vaccines. Cytokine Growth Factor Rev. 18:195-207.
9. Chatfield, S. N., M. Roberts, G. Dougan, C. Hormaeche, and C. M. A. Khan. 1995. The development of oral vaccines against parasitic diseases utilizing live attenuated *Salmonella*. Parasitology 110:S17-S24.
10. Cheminay, C., and M. Hensel. 2008. Rational design of *Salmonella* recombinant vaccines. Int. J. Med. Microbiol. 298:87-98.
11. Collins, L. V., S. Attridge, and J. Hackett. 1991. Mutations at rfc or pmi attenuate *Salmonella typhimurium* virulence for mice. Infect. Immun. 59:1079-1085.
12. Curtiss III, R. 2002. Bacterial infectious disease control by vaccine development. J. Clin. Invest. 110:1061-1066.
13. Curtiss III, R., S.-Y. Wanda, B. M. Gunn, X. Zhang, S. A. Tinge, V. Ananthnarayan, H. Mo, S. Wang, and W. Kong. 2009. *Salmonella enterica* serovar *Typhimurium* strains with regulated delayed attenuation in vivo. Infect. Immun. 77:1071-1082.
14. Curtiss III, R., X. Zhang., S. Y. Wanda., HoYoung Kang, V. Konjufca., Y. Li., B. Gunn., S. Wang., G. Scarpellini., Lee In Soo. 2007. Induction of host immune responses using *Salmonella*-vectored vaccines. Virulence mechanisms of bacterial pathogens, 4th ed. ASM Press, Washington, D.C.: 297-313.
15. Curtiss, R., and S. M. Kelly. 1987. *Salmonella typhimurium* deletion mutants lacking adenylate-cyclase and cyclic-amp receptor protein are avirulent and immunogenic. Infect. Immun. 55:3035-3043.
16. Edwards, R. A., L. H. Keller, and D. M. Schifferli. 1998. Improved allelic exchange vectors and their use to analyze 987P fimbria gene expression. Gene 207:149-157.
17. Frirdich, E., and C. Whitfield. 2005. Lipopolysaccharide inner core oligosaccharide structure and outer membrane stability in human pathogens belonging to the Enterobacteriaceae. J. Endoxtin Res. 11:133-144.
18. Germanie. R, and E. Furer. 1971. Immunity in experimental salmonellosis. 2. basis for avirulence and protective capacity of galE mutants of *Salmonella typhimurium*. Infect. Immun. 4:663-&.
19. Hassan, J. O., and R. Curtiss. 1990. Control of colonization by virulent *Salmonella Typhimurium* by oral immunization of chickens with avirulent delta-Cya delta-Crp *Salmonella Typhimurium*. Res. Microbiol. 141:839-850.
20. Hitchcock, P. J., and T. M. Brown. 1983. Morphological heterogeneity among *Salmonella* lipopolysaccharide chemotypes in silver stained polyacrylamide gels. J. Bacteriol. 154:269-277.
21. Hoare, A., M. Bittner, J. Carter, S. Alvarez, M. Zaldivar, D. Bravo, M. A. Valvano, and I. Contreras. 2006. The outer core lipopolysaccharide of *Salmonella enterica* Serovar *typhi* is required for bacterial entry into epithelial cells. Infect. Immun. 74:1555-1564.
22. Hone, D., R. Morona, S. Attridge, and J. Hackett. 1987. Contruction of defined galE mutants of *Salmonella* for use as vaccines. J. Infect. Dis. 156:167-174.
23. Hone, D. M., S. R. Attridge, B. Forrest, R. Morona, D. Daniels, J. T. Labrooy, R. C. A. Bartholomeusz, D. J. C. Shearman, and J. Hackett. 1988. A Gale-Via (Vi-Antigen-Negative) Mutant of *Salmonella-Typhi* Ty2 Retains Virulence in Humans. Infect. Immun. 56:1326-1333.
24. Hone, D. M., S. R. Attridge, B. Forrest, R. Morona, D. Daniels, J. T. Labrooy, R. C. A. Bartholomeusz, D. J. C. Shearman, and J. Hackett. 1988. A galE-via (Vi-antigen-negative) mutant of *Salmonella typhi* Ty2 retains virulence in humans. Infect. Immun. 56:1326-1333.
25. Kang, H. Y., J. Srinivasan, and R. Curtiss III. 2002. Immune responses to recombinant pneumococcal PspA antigen delivered by live attenuated *Salmonella enterica* serovar *Typhimurium* vaccine. Infect. Immun. 70:1739-1749.
26. Kong, Q., Q. Liu, K. L. Roland, and R. Curtiss, III. 2009. Regulated delayed expression of rfaH in an attenuated *Salmonella enterica* Serovar *Typhimurium* vaccine enhances immunogenicity of outer membrane proteins and a heterologous antigen. Infect. Immun. 77:5572-5582.
27. Kong, W., S. Y. Wanda, X. Zhang, W. Bollen, S. A. Tinge, K. L. Roland, and R. Curtiss. 2008. Regulated programmed lysis of recombinant *Salmonella* in host tissues to release protective antigens and confer biological containment. Proc. Natl. Acad. Sci. U.S.A. 105:9361-9366.
28. Kwon, Y. M., M. M. Cox, and L. N. Calhoun. 2007. *Salmonella*-based vaccines for infectious diseases. Expert Rev. Vaccines 6:147-152.
29. Li, Y., S. Wang, G. Scarpellini, B. Gunn, W. Xin, S. Y. Wanda, K. L. Roland, and R. Curtiss III. 2009. Evaluation of new generation *Salmonella enterica* serovar *Typhimurium* vaccines with regulated delayed attenuation to induce immune responses against PspA. Proc. Natl. Acad. Sci. U.S.A. 106:593-598.
30. Li, Y., S. Wang, W. Xin, G. Scarpellini, Z. Shi, B. Gunn, K. L. Roland, and R. Curtiss III. 2008. A sopB deletion mutation enhances the immunogenicity and protective efficacy of a heterologous antigen delivered by live attenuated *Salmonella enterica* vaccines. Infect. Immun. 76:5238-5246.
31. Lindberg, A. A., and C. G. Hellerqvist. 1980. Rough mutants of *Salmonella typhimurium*—Immunochemical and structural analysis of lipopolysaccharides from rfaH mutants. J. Gen. Microbiol. 116:25-32.
32. Maggini, J., S. Raiden, G. Salamone, A. Trevani, and J. Geffner. 2009. Regulation of neutrophil apoptosis by cytokines, pathogens and environmental stressors. Front. Biosci. 14:2372-2385.

33. Malley, R., K. Trzcinski, A. Srivastava, C. M. Thompson, P. W. Anderson, and M. Lipsitch. 2005. CD4(+) T cells mediate antibody-independent acquired immunity to pneumococcal colonization. Proc. Natl. Acad. Sci. U.S.A. 102:4848-4853.
34. McDaniel, L. S., J. S. Sheffield, P. Delucchi, and D. E. Briles. 1991. PspA, a surface protein of *Streptococcus pneumoniae*, is capable of eliciting protection against pneumococci of more than one capsular type. Infect. Immun. 59:222-228.
35. Medina, E., and C. A. Guzman. 2001. Use of live bacterial vaccine vectors for antigen delivery: potential and limitations. Vaccine 19:1573-1580.
36. Morgan, E., J. D. Campbell, S. C. Rowe, J. Bispham, M. P. Stevens, A. J. Bowen, P. A. Barrow, D. J. Maskell, and T. S. Wallis. 2004. Identification of host-specific colonization factors of *Salmonella enterica* serovar *Typhimurium*. Mol. Microbiol. 54:994-1010.
37. Murtaugh, M. P., and D. L. Foss. 2002. Inflammatory cytokines and antigen presenting cell activation. Vet. Immunol. Immunopathol. 87:109-121.
38. Nagy, G., V. Damino, U. Dobrindt, M. Pallen, R. Chaudhuri, L. Emody, J. C. Hinton, and J. Hacker. 2006. Down-regulation of key virulence factors makes the *Salmonella enterica* serovar *Typhimurium* rfaH mutant a promising live-attenuated vaccine candidate. Infect. Immun. 74:5914-5925.
39. Nagy, G., U. Dobrindt, J. Hacker, and L. Emody. 2004. Oral immunization with an rfaH mutant elicits protection against salmonellosis in mice. Infect. Immun. 72:4297-4301.
40. Nagy, G., L. Emody, and T. Pal. 2008. Strategies for the development of vaccines conferring broad-spectrum protection. Int. J. Med. Microbiol. 298:379-395.
41. Nagy, G., and T. Pal. 2008. Lipopolysaccharide: a tool and target in enterobacterial vaccine development. Biol. Chem. 389:513-520.
42. Nagy, G., T. Palkovics, A. Otto, H. Kusch, B. Kocsis, U. Dobrindt, S. Engelmann, M. Hecker, L. Emody, T. Pal, and J. Hacker. 2008. "Gently rough": The vaccine potential of a *Salmonella enterica* regulatory lipopolysaccharide mutant. J. Infect. Dis. 198:1699-1706.
43. Nakayama, K., S. M. Kelly, and R. Curtiss III. 1988. Construction of an Asd⁺ expression-cloning vector: stable maintenance and high level expression of cloned genes in a *Salmonella* vaccine strain. Nat. Bio-technol. 6:693-697.
44. Nayak, A. R., S. A. Tinge, R. C. Tart, L. S. McDaniel, D. E. Briles, and R. Curtiss III. 1998. A live recombinant avirulent oral *Salmonella* vaccine expressing pneumococcal surface protein A induces protective responses against *Streptococcus pneumoniae*. Infect. Immun. 66:3744-3751.
45. Neidhardt, F. C., P. L. Bloch, and D. F. Smith. 1974. Culture medium for enterobacteria. J. Bacteriol. 119:736-747.
46. Nevola, J. J., D. C. Laux, and P. S. Cohen. 1987. In vivo colonization of the mouse large intestine and in vitro penetration of intestinal mucus by an avirulent smooth strain of *Salmonella typhimurium* and its lipopolysaccharide-deficient mutant. Infect. Immun. 55:2884-2890.
47. Nevola, J. J., B. A. Stocker, D. C. Laux, and P. S. Cohen. 1985. Colonization of the mouse intestine by an avirulent *Salmonella typhimurium* strain and its lipopolysaccharide-defective mutants. Infect. Immun. 50:152-159.
48. Raetz, C. R., and C. Whitfield. 2002. Lipopolysaccharide endotoxins. Annu. Rev. Biochem. 71:635-700.
49. Rojas, G., S. Saldias, M. Bittner, M. Zaldivar, and I. Contreras. 2001. The rfaH gene, which affects lipopolysaccharide synthesis in *Salmonella enterica* serovar *Typhi*, is differentially expressed during the bacterial growth phase. FEMS Microbiol. Lett. 204:123-128.
50. Roland, K., R. Curtiss III, and D. Sizemore. 1999. Construction and evaluation of a delta cya delta crp *Salmonella typhimurium* strain expressing avian pathogenic *Escherichia coli* O78 LPS as a vaccine to prevent airsacculitis in chickens. Avian Dis. 43:429-441.
51. Sambandamurthy, V. K., and W. R. Jacobs. 2005. Live attenuated mutants of *Mycobacterium tuberculosis* as candidate vaccines against tuberculosis. Microbes Infect. 7:955-961.
52. Sambrook, J., E. F. Fritsch, and T. Maniatis. 1989. Molecular cloning: a laboratory manual, 2nd ed. Cold Spring Harbor Laboratory Press, Cold Spring Harbor, N.Y.
53. Samuel, G., and P. Reeves. 2003. Biosynthesis of O-antigens: genes and pathways involved in nucleotide sugar precursor synthesis and O-antigen assembly. Carbohydr. Res. 338:2503-2519.
54. Sanderson, K. E., and B. A. D. Stocker. 1981. Gene rfaH, which affects lipopolysaccharide core structure in *Salmonella typhimurium*, is required also for expression of F-factor functions. J. Bacteriol. 146:535-541.
55. Santangelo, T. J., and J. W. Roberts. 2002. RfaH, a bacterial transcription antiterminator. Mol. Cell 9:698-700.
56. Schmieger, H. 1972. Phage P22 mutants with increased or decreased transduction abilities. Mol. Gen. Genet. 119:75-&.
57. Shaio, M. F., and H. Rowland. 1985. Bactericidal and opsonizing effects of normal serum on mutant strains of *Salmonella typhimurium*. Infect. Immun. 49:647-653.
58. Singh, S. P., Y. U. Williams, P. E. Klebba, P. Macchia, and S. Miller. 2000. Immune recognition of porin and lipopolysaccharide epitopes of *Salmonella typhimurium* in mice. Microb. Pathog. 28:157-167.
59. Stevenson, G., and P. A. Manning. 1985. Galactose epimeraseless (GalE) mutant G30 of *Salmonella typhimurium* is a good potential live oral vaccine carrier for fimbrial antigens. FEMS Microbiol. Lett. 28:317-321.
60. Stocker, B. A. D., and P. H. Makela. 1986. Genetic determination of bacterial virulence, with special reference to *Salmonella*. Curr. Top. Microbiol. Immunol. 124:149-172.
61. Stocker, B. A. D., and P. H. Makela. 1978. Genetics of (Gram-Negative) bacterial surface. P. Roy. Soc. Lond. B. Bio. 202:5-30.
62. Stocker, B. A. D., B. M. Males, and W. Takano. 1980. *Salmonella typhimurium* mutants of rfaH-phenotype, genetics and antibiotic sensitivities. J. Gen. Microbiol. 116:17-24.
63. Sun, W., S. Wang, and R. Curtiss III. 2008. Highly efficient method for introducing successive multiple scarless gene deletions and markerless gene insertions into the *Yersinia pestis* chromosome. Appl. Environ. Microbiol. 74:4241-4245.
64. Toguchi, A., M. Siano, M. Burkart, and R. M. Harshey. 2000. Genetics of swarming motility in *Salmonella enterica* serovar *Typhimurium*: critical role for lipopolysaccharide. J. Bacteriol. 182:6308-6321.
65. Tran, A. X., C. Whitfield, and S. Moselio. 2009. Lipopolysaccharides (Endotoxins), p. 513-528. Encyclopedia of Microbiology. Academic Press, Oxford.
66. Valentine, P. J., B. P. Devore, and F. Heffron. 1998. Identification of three highly attenuated *Salmonella typhimurium* mutants that are more immunogenic and protective in mice than a prototypical aroA mutant. Infect. Immun. 66:3378-3383.

67. Whitfield, C. 1995. Biosynthesis of Lipopolysaccharide O-Antigens. Trends Microbiol. 3:178-185.
68. Whitfield, C., N. Kaniuk, and E. Frirdich. 2003. Molecular insights into the assembly and diversity of the outer core oligosaccharide in lipopolysaccharides from *Escherichia coli* and *Salmonella*. J. Endoxtin Res. 9:244-249.
69. Wiegand, I., K. Hilpert, and R. E. W. Hancock. 2008. Agar and broth dilution methods to determine the minimal inhibitory concentration (MIC) of antimicrobial substances. Nat. Protocols 3:163-175.
70. Wu, H. Y., M. H. Nahm, Y. Guo, M. W. Russell, and D. E. Briles. 1997. Intranasal immunization of mice with PspA (Pneumococcal surface protein A) can prevent intranasal carriage, pulmonary infection, and sepsis with *Streptococcus pneumoniae*. J. Infect. Dis. 175:839-846.
71. Xin, W., S. Y. Wanda, Y. Li, S. Wang, H. Mo, and R. Curtiss III. 2008. Analysis of type II secretion of recombinant pneumococcal PspA and PspC in a *Salmonella enterica* serovar *Typhimurium* vaccine with regulated delayed antigen synthesis. Infect. Immun. 76:3241-3254.
72. Shivaprasad, H. L. 2000. Fowl typhoid and pullorum disease. Revue scientifique et technique (International Office of Epizootics) 19:405-424.
73. Felix, A. 1951. The pathogenic and immunogenic activities of *Salmonella typhi* in relation to its antigenic constituents. The Journal of Hygiene 49(1):92-110.
74. Hone, D. M. 1991. Construction of genetically defined double aro mutants of *Salmonella typhi*. Vaccine 9(11) 810-6.
75. Thompson, N. R. 20008. Comparative genome analysis of *Salmonella Enteritidis* PT4 and *Salmonella Gallinarum* 287/91 provides insights into evolutionary and host adaptation pathways. Genome Research 10:1624-37.

What is claimed is:

1. A recombinant bacterium, the bacterium comprising a first chromosomally integrated nucleic acid sequence encoding rfaH operably linked to a regulatable promoter and a second chromosomally integrated nucleic acid sequence encoding rfc operably linked to a regulatable promoter.

2. The bacterium of claim 1, wherein the bacterium further comprises at least one nucleic acid sequence encoding at least one exogenous antigen.

3. A vaccine, the vaccine comprising a recombinant bacterium of claim 1.

4. The recombinant bacterium of claim 1, wherein the bacterium is derived from a *Salmonella enterica* serovar selected from the group consisting of *Typhimurium, Typhi, Paratyphi, Gallinarum, Enteritidis, Choleraesius, Arizonae,* and *Dublin*.

5. The bacterium of claim 1, wherein transcription of rfaH and rfc occurs during in vitro growth but not during growth of the bacterium in an animal or human host.

6. The bacterium of claim 1, wherein the regulatable promoter is sensitive to a chemical difference between in vitro growth and growth in an animal or human host.

7. The bacterium of claim 6, wherein the chemical is a sugar selected from the group consisting of arabinose, maltose, rhamnose, xylose, and a combination thereof.

8. The bacterium of claim 1, wherein the bacterium further comprises a mutation selected from the group consisting of $\Delta P_{rfaH176}$::TTaraCP$_{BAD}$ rfaH, $\Delta Pr_{rfaH177}$::TTaraCP$_{BAD}$ rfaH, and $\Delta Pr_{rfaH178}$::TTaraCP$_{BAD}$ rfaH.

9. The bacterium of claim 1, wherein the bacterium further comprises a mutation selected from the group consisting of $\Delta P_{rfc173}$::TTaraCP$_{BAD}$ rfc, $\Delta P_{rfc174}$::TTaraCP$_{BAD}$ rfc, and $\Delta P_{rfc175}$::TTaraCP$_{BAD}$ rfc.

10. The bacterium of claim 2, wherein the at least one exogenous antigen is selected from the group consisting of:
(i) an *E. coli* antigen selected from the group consisting of salmochelin, aerobactin, the sit operon nucleic acid product, the fimbriae encoded by the yagZ fimbrial operon, other fimbriae encoded by other nucleic acids, the tsh nucleic acid product, the iss nucleic acid product, and the non-toxic cell binding domain of the LT toxin (LT-B);
(ii) a *Yersinia* antigen selected from the group consisting of the V antigen and the psn nucleic acid product;
(iii) a *Shigella* antigen selected from the group consisting of IpaD and aerobactin;
(iv) a *C. jejuni* antigen selected from the group consisting of PilA and CjaA; and
(v) a *C. perfringens* antigen selected from the group consisting of α-toxin and NetB.

* * * * *